(12) United States Patent
Gross et al.

(10) Patent No.: US 11,147,955 B2
(45) Date of Patent: Oct. 19, 2021

(54) REGULATOR DEVICE FOR DRUG PATCH

(71) Applicant: ALMA THERAPEUTICS LTD., Petach-Tikva (IL)

(72) Inventors: Yossi Gross, Moshav Mazor (IL); Oz Cabiri, Hod-HaSharon (IL); Ran Hezkiahu, Herzlia (IL)

(73) Assignee: Alma Therapeutics Ltd., Petach Tikva (IL)

( * ) Notice: Subject to any disclaimer, the term of this patent is extended or adjusted under 35 U.S.C. 154(b) by 641 days.

(21) Appl. No.: 15/551,522

(22) PCT Filed: Feb. 18, 2016

(86) PCT No.: PCT/IL2016/050196
§ 371 (c)(1),
(2) Date: Aug. 16, 2017

(87) PCT Pub. No.: WO2016/132368
PCT Pub. Date: Aug. 25, 2016

(65) Prior Publication Data
US 2018/0036523 A1 Feb. 8, 2018

Related U.S. Application Data

(63) Continuation-in-part of application No. 14/624,721, filed on Feb. 18, 2015, now Pat. No. 10,004,887.

(51) Int. Cl.
*A61M 37/00* (2006.01)
*A61K 9/70* (2006.01)

(52) U.S. Cl.
CPC ....... *A61M 37/0015* (2013.01); *A61K 9/7023* (2013.01); *A61M 2205/3303* (2013.01);
(Continued)

(58) Field of Classification Search
CPC ............ A61K 9/7023; A61M 37/0015; A61M 2205/3303; A61M 2205/3569; A61M 2205/50
(Continued)

(56) References Cited

U.S. PATENT DOCUMENTS 5,190,558 A    3/1993  Ito
5,498,235 A    3/1996  Flower
(Continued)

FOREIGN PATENT DOCUMENTS

EP    0848937 A2    6/1998
GB    2448493 A    10/2008
(Continued)

OTHER PUBLICATIONS

Harapanhalli "Scientific and Regulatory Challenges of Transdermal Drug Delivery Systems (TDDS) and Relevance of Quality-by-Design (QbD) Approach to Their Development", Presented to the Advisory Committee for Pharmaceutical Science and Clinical Pharmacology, FDA, U.S, Food and Drug Administration, Silver Spring, MD, USA, Aug. 5, 2009, p. 1-38, Aug. 2009.
(Continued)

*Primary Examiner* — Phillip A Gray
(74) *Attorney, Agent, or Firm* — Dekel Patent Ltd.; David Klein

(57) ABSTRACT

Embodiments are disclosed of a method of controlling timing and/or dosage of a transdermal drug patch. For example, a control device operative to move the patch to one or more of a plurality of operational relationships with a skin of a patient, including being fully engaged with the skin, partially engaged with the skin, and disengaged with the skin. The device may include a roller that peels a patch on and off the skin. Optionally a convention patch is used. In some embodiments a patch and/or an adaptor has a mobile
(Continued)

zone and an immobile zone. In some embodiments, an active surface of the patch fully contacts the skin in an engaged state. For example the patch may be attached to the device on a passive portion thereof.

18 Claims, 33 Drawing Sheets

(52) U.S. Cl.
CPC . *A61M 2205/3569* (2013.01); *A61M 2205/50* (2013.01); *A61M 2205/502* (2013.01); *A61M 2209/088* (2013.01)

(58) Field of Classification Search
USPC ....................................................... 604/890.1
See application file for complete search history.

(56) References Cited

U.S. PATENT DOCUMENTS

| | | | |
|---|---|---|---|
| 6,589,202 B1* | 7/2003 | Powell | A61B 10/0045 604/27 |
| 2003/0065294 A1 | 4/2003 | Pickup et al. | |
| 2004/0087992 A1 | 5/2004 | Gartstein et al. | |
| 2007/0161964 A1 | 7/2007 | Yuzhakov | |
| 2008/0208146 A1 | 8/2008 | Brandwein et al. | |
| 2008/0220092 A1 | 9/2008 | Dipierro et al. | |
| 2010/0042050 A1* | 2/2010 | Chowdhury | A61M 37/0015 604/173 |
| 2010/0129013 A1* | 5/2010 | Schroeder | F16C 29/005 384/45 |
| 2010/0256568 A1 | 10/2010 | Frederickson et al. | |
| 2012/0302942 A1 | 11/2012 | Dipierro et al. | |
| 2013/0144261 A1 | 6/2013 | Chowdhury | |
| 2014/0200525 A1 | 7/2014 | Dipierro | |
| 2014/0207047 A1 | 7/2014 | Dipierro et al. | |
| 2014/0207048 A1 | 7/2014 | Dipierro et al. | |
| 2014/0323423 A1 | 10/2014 | Dipierro et al. | |
| 2016/0038434 A1 | 2/2016 | Schaller et al. | |

FOREIGN PATENT DOCUMENTS

| | | |
|---|---|---|
| WO | 2014203910 A1 | 12/2014 |
| WO | 2016132368 A1 | 8/2016 |

OTHER PUBLICATIONS

Sadrien "Challenges in the Development of Transdermal Drug Delivery Systems", Presented to the Advisory Committee for Pharmaceutical Scinece and Clinical Pharmacology, FDA, U.S. Food and Drug Administration, Silver Spring, MD, USA, Aug. 5, 2009, p. 1-17, Aug. 2009.

* cited by examiner

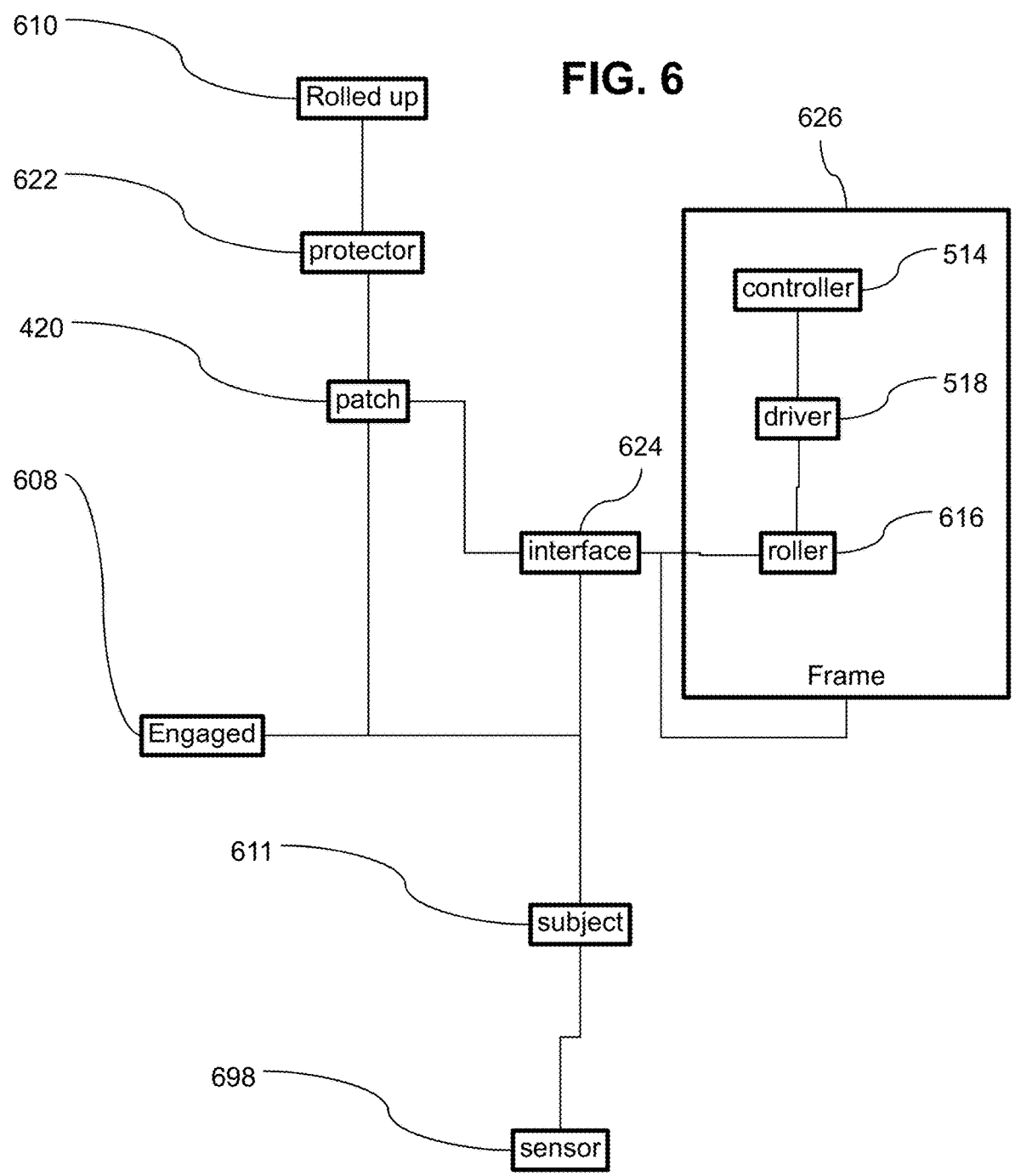

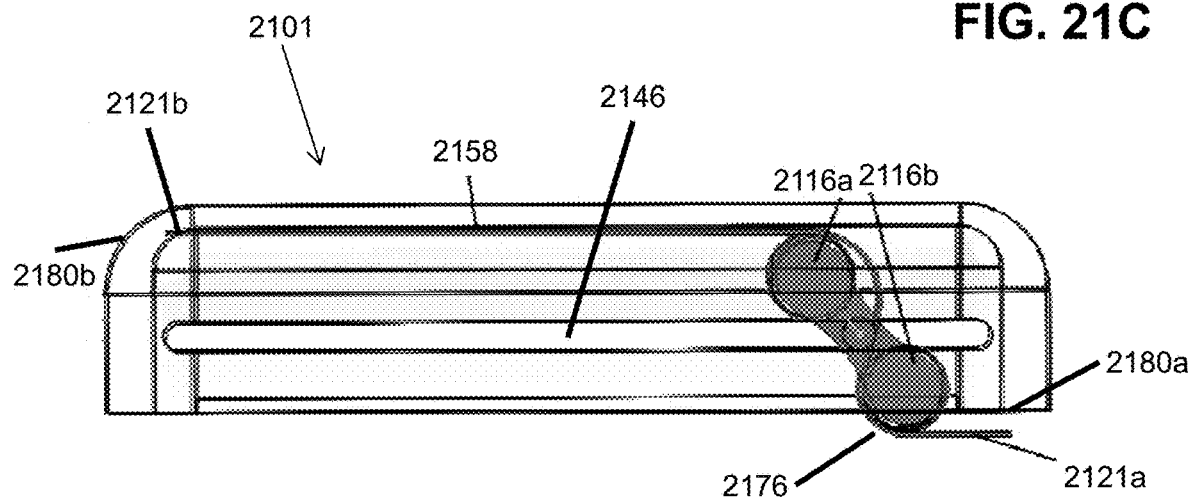
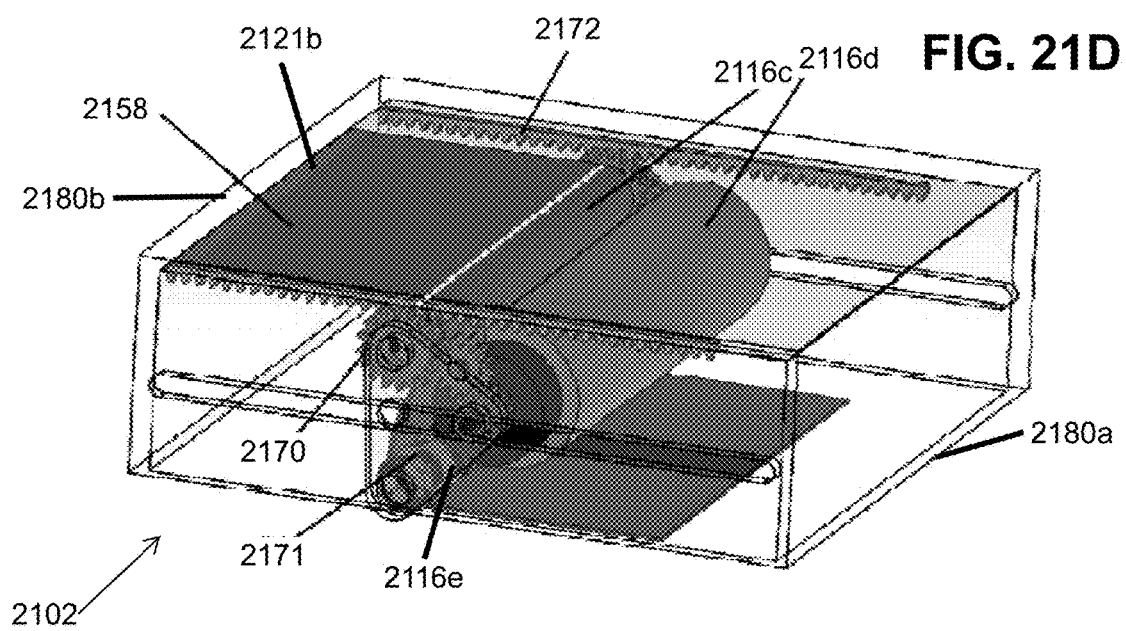

REGULATOR DEVICE FOR DRUG PATCH

RELATED APPLICATIONS

This application is a National Phase of PCT Patent Application No. PCT/IL2016/050196 having International filing date of Feb. 18, 2016, which is a Continuation In Part of U.S. patent application Ser. No. 14/624,721 filed Feb. 18, 2015.

The contents of the above applications are all incorporated by reference as if fully set forth herein in their entirety.

FIELD AND BACKGROUND OF THE INVENTION

The present invention, in some embodiments thereof, relates to a system to control transdermal delivery and, more particularly, but not exclusively, to a system to control timing, rate and/or dosage of transdermal delivery from a conventional drug patch and/or a customized drug patch.

U.S. Patent Publication No. 2014/0323423 discloses "systems and methods for longevity, anti-aging, fatigue management, obesity, weight loss, weight management, delivery of nutraceuticals, and treating hyperglycemia, Alzheimer's disease, sleep disorders, Parkinson's disease, Attention Deficit Disorder and nicotine addiction involve synchronizing and tailoring the administration of nutraceuticals, medications and other substances (for example, stimulants) in accordance with the body's natural circadian rhythms, meal times and other factors. Improved control of blood glucose levels, extended alertness, and weight control, and counteracting of disease symptoms when they are at their worst are possible. An automated, pre-programmable transdermal administration system is used to provide pulsed doses of medications, pharmaceuticals, hormones, neuropeptides, anorexigens, pro-drugs, stimulants, plant extracts, botanicals, nutraceuticals, cosmeceuticals, phytochemicals, phytonutrients, enzymes, antioxidants, essential oils, fatty acids, minerals, vitamins, amino acids, coenzymes, or other physiological active ingredient or precursor. The system can utilize a pump, pressurized reservoir, a system for removing depleted carrier solution, or other modulated dispensing actuator, in conjunction with porous membranes or microfabricated structures."

U.S. Patent Publication No. 2014/0207048 discloses "establishing a bio-synchronous treatment protocol that incorporates individual temporal and innate biological characteristics into a pharmacological treatment plan. The bio-synchronous treatment protocol is thereafter initiated using bioactive agent delivery device. Bio-synchronous drug delivery includes continual collection of patient data such as physical, psychological, temporal and environmental characteristics. This data is analyzed so to not only determine an initial treatment protocol but to also determining whether modification to the ongoing bio-synchronous treatment protocol is required. And, responsive to determining a modification is required the system modifies the bio-synchronous treatment protocol and use of delivery device. These modifications and treatment protocols can include reactive and proactive psychological support supplied to the patient in a variety of formats."

U.S. Patent Publication No. 2014/0207047 discloses "a bioactive agent delivery device having a plurality of reservoirs wherein each reservoir houses a solvent provides a means for separable and segregated delivery of bioactive agent(s) to a patient. The device can include a plurality of absorbent materials wherein each absorbent material is pretreated with a bioactive agent and a delivery mechanism operable to deliver to any of the plurality of absorbent materials a controlled portion of solvent from any of a plurality of reservoirs. A diffusion layer interposed between the absorbent materials and an epidermis transfers the bioactive agent from the absorbent materials to the epidermis for delivery of the bioactive agent."

U.S. Patent Publication No. 2014/0200525 discloses "systems and methods for synchronizing the administration of compounds with the human body's natural circadian rhythms and addiction rhythms to counteract symptoms when they are likely to be at their worst by using an automated and pre programmable transdermal or other drug administration system."

Additional background art includes U.S. Patent Publication No. 2012/0302942 U.S. Patent Publication No. 2008/0220092.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to an aspect of some embodiments of the invention, there is provided a regulator for a transdermal drug administration to a subject comprising: an connector for attachment to a transdermal drug patch; and an actuator mechanically manipulating the transdermal patch with respect to a skin of the subject for at least one action including distancing an active surface of the patch from a skin of the subject and/or contacting the active surface to the skin.

According to some embodiments of the invention, the patch includes a conventional transdermal drug patch configured for administering a drug according to a predetermined dosage schedule.

According to some embodiments of the invention, the patch includes an active surface and a non-active zone and the connector is configured to attach to the patch on the non-active zone.

According to some embodiments of the invention, and active portion of the patch is uncompromised by the regulator.

According to some embodiments of the invention, the regulator further comprises: a controller operationally connected to the actuator to control the manipulating to perform the distancing at a time predetermined before attachment of the patch to the subject.

According to an aspect of some embodiments of the invention, there is provided a regulator for a transdermal drug administration to a subject comprising: an attachment surface configured for attachment to the skin of the subject; a connector for attachment to a transdermal drug patch; and an actuator for moving the connector with respect to the attachment surface.

According to some embodiments of the invention, the actuator is configured to perform at least on function selected from the group consisting of fully engaging the patch to the skin, partially engaging the patch to the skin and disengaging the patch from the skin.

According to some embodiments of the invention, the regulator further comprises: a guide directing a separation line between the patch and the skin.

According to some embodiments of the invention, the actuator includes a puller for peeling the patch from the skin.

According to some embodiments of the invention, the patch includes a conventional transdermal drug patch configured for administering a drug according to a predetermined dosage schedule.

According to some embodiments of the invention, the fully engaging includes positioning an active surface of patch fully contact skin according to the regulation of the patch without the regulator.

According to some embodiments of the invention, and active portion of the patch is uncompromised by the regulator.

According to some embodiments of the invention, the patch includes an active surface and a non-active zone and the connector is configured to attach to the patch on the non-active zone.

According to some embodiments of the invention, the regulator further comprises: a repository for storing a portion of the patch in an unengaged state.

According to some embodiments of the invention, the regulator further comprises: a roller and wherein the repository includes a roll of the patch wrapped around the roller.

According to some embodiments of the invention, the regulator further comprises: a protector located between layers of the patch wrapped on the roller.

According to some embodiments of the invention, the protector includes a dorsal surface of the patch.

According to some embodiments of the invention, the patch includes conventional transdermal drug patch configured for administering a drug according to a predetermined dosage schedule and an adapter configured to attach to dorsal face conventional patch and including the protector.

According to some embodiments of the invention, the roller includes the actuator.

According to some embodiments of the invention, the regulator further comprises a synchronizer to synchronize rate of rotation of the roller with rate of at least one of the fully engaging and the disengaging.

According to some embodiments of the invention, the roller rotates and moves linearly with respect the attachment surface.

According to some embodiments of the invention, the regulator further comprises: an alignment device for aligning the patch to the device when mounting the patch to the device.

According to some embodiments of the invention, the regulator further comprises: a non-reactive protector cover for an active surface of the patch during the storing.

According to some embodiments of the invention, when the patch is wrapped around the roller, the active surface contacts the non-reactive surface.

According to some embodiments of the invention, the non reactive surface comprises Polyethylene.

According to an aspect of some embodiments of the invention, there is provided a regulator for a transdermal drug administration to a subject comprising: a ventral contact surface configured to attach to a dorsal surface of a transdermal patch when the device is place onto the patch and an actuator mechanically manipulating the transdermal patch.

According to an aspect of some embodiments of the invention, there is provided a regulator for a transdermal drug administration to a subject comprising: a connector for attachment to a transdermal drug patch; and an actuator configured to peel the patch from a skin of a subject.

According to some embodiments of the invention, the actuator is configured to pull the patch at an angle between 70 to 110 degreed of the skin surface.

According to an aspect of some embodiments of the invention, there is provided a regulator for a transdermal drug administration to a subject comprising: a connector for attachment to a transdermal drug patch; and a roller to store the patch.

According to an aspect of some embodiments of the invention, there is provided a regulator for a transdermal drug administration to a subject comprising: a connector for attachment to a transdermal drug patch; and a flat support to guide the patch near a separation line.

According to an aspect of some embodiments of the invention, there is provided a method of transdermal drug administration to a subject comprising: supplying a transdermal drug patch certified to administer a drug to a fixed cumulative dosage and a patch controller device; administering the drug to the subject with the drug patch; interrupting the administering automatically by the patch controller device before administration of 80% of the fixed dosage.

According to some embodiments of the invention, the method further comprises: restarting the administering at least 20 minutes after the interrupting.

According to some embodiments of the invention, the interrupting includes reducing a rate of the administering by at least 50% over a period of less than 30 minutes.

According to some embodiments of the invention, the interrupting includes reducing an area of contact of an active zone of the patch and a skin of the subject by at least 50%.

According to some embodiments of the invention, the interrupting peeling a portion of the patch off a skin of the subject.

According to some embodiments of the invention, a separation line of the peeling is a line of contact of a roller.

According to some embodiments of the invention, the method further comprises: storing at least a portion of the patch rolled around on a roller.

According to some embodiments of the invention, the method further comprises: storing at least a portion overlying a second portion of the patch.

According to some embodiments of the invention, the method further includes: positioning a liner between the at least a portion and the second portion.

According to some embodiments of the invention, the method further comprises: attaching the control device to the subject.

According to some embodiments of the invention, the method further comprises: programming the control device to perform the interrupting at a predetermined time.

According to some embodiments of the invention, the programming is prior to the administering.

According to some embodiments of the invention, the method further comprises: sensing an event and wherein the interrupting is in response to an event.

According to some embodiments of the invention, the event is a reaction to of the subject to the drug.

According to some embodiments of the invention, the method further comprises: commanding the control device to perform the interrupting.

According to some embodiments of the invention, the commanding includes transmitting a wireless signal to the control device.

According to some embodiments of the invention, the method further comprises: initiating a new administering of a second drug automatically after the administrating.

According to some embodiments of the invention, the initiating a new administering is after the interrupting.

According to some embodiments of the invention, the initiating a new administering includes exposing a new zone of the patch to a skin of the subject.

According to an aspect of some embodiments of the invention, there is provided a method of transdermal drug administration to a subject comprising: supplying a transdermal drug patch certified for administering a drug to a fixed cumulative dosage connected to a control device; attaching the transdermal patch to the subject without initiating administration of the drug; and automatically initiating the administering of the drug by the control device at least 20 minutes after the attaching.

According to some embodiments of the invention, the attaching includes placing an active region of the patch in direct contact with a skin of the subject.

According to some embodiments of the invention, the initiating includes placing at least half the surface of an active region of the patch in direct contact with a skin of the subject.

According to some embodiments of the invention, after the initiating, the patch releases the drug according to a fixed dosage schedule certified for the patch.

According to some embodiments of the invention, the method further comprises: interrupting the administering after the initiating automatically by the patch controller device before administration of 80% of the fixed dosage.

According to some embodiments of the invention, the interrupting includes reducing a rate of the administering by at least 50% over a period of less than 30 minutes.

According to some embodiments of the invention, the interrupting includes reducing an area of contact of an active zone of the patch and a skin of the subject by at least 50%.

According to some embodiments of the invention, the initiating includes rolling an active zone of the patch onto a skin of the subject.

According to some embodiments of the invention, the method further comprises: storing at least a portion of the patch rolled around on a roller.

According to some embodiments of the invention, the attaching is by means of an adhesive.

According to some embodiments of the invention, the method further comprises: programming the control device to perform the initiating at a predetermined time.

According to some embodiments of the invention, the method further comprises: commanding the control device to perform the initiating.

According to some embodiments of the invention, the commanding includes transmitting a wireless signal to the control device.

According to some embodiments of the invention, the method further comprises: sensing an event and wherein the initiating is in response to the sensing.

According to some embodiments of the invention, the programming is prior to the attaching.

According to some embodiments of the invention, the event is a medical condition requiring treatment by the drug.

According to an aspect of some embodiments of the invention, there is provided a method of transdermal drug administration to a subject comprising: supplying a transdermal drug patch certified for administering a drug to according to a fixed dosage schedule connected to a control device; attaching the transdermal patch to the subject with the control device; and administering the drug with the drug patch to the subject at a modified rate schedule having a dosage rate less than a dosage rate the fixed dosage schedule.

According to some embodiments of the invention, the method further comprises: contacting between 20 to 80% of an active aria of the patch to a skin of a subject.

According to some embodiments of the invention, the method further comprises: increasing the modified rate schedule in response to an event.

According to some embodiments of the invention, the increasing the modified rate schedule is by increasing an area of contact between an active zone of the patch and a skin of the subject.

According to some embodiments of the invention, the method further comprises: decreasing the modified rate schedule in response to an event.

According to some embodiments of the invention, the decreasing the modified rate schedule is by decreasing an area of contact between an active zone of the patch and a skin of the subject.

According to an aspect of some embodiments of the invention, there is provided a method of transdermal drug administration to a subject comprising: supplying a transdermal drug patch having an active zone for administering the drug, the patch loaded into a patch control device; attaching the patch control device to the subject with the active zone of the patch at least partially disengaged from the subject; engaging a disengaged portion of the active zone to the subject with the device at least 20 minutes after the attaching.

According to some embodiments of the invention, in the partially disengaged state at least a portion of the active zone is distanced at least 1 mm from a skin of the subject and wherein the engaging includes moving the portion to contact with the skin.

According to some embodiments of the invention, after the engaging, the patch releases the drug according to a fixed dosage schedule certified for the patch.

According to some embodiments of the invention, the method further comprises: disengaging a portion of the active zone after the engaging automatically by the patch controller device.

According to some embodiments of the invention, the engaging includes rolling an active zone of the patch onto a skin of the subject.

According to some embodiments of the invention, the method further comprises: storing at least a portion of the patch rolled around on a roller.

According to some embodiments of the invention, the attaching is by means of an adhesive.

According to some embodiments of the invention, the method further comprises: programming the control device to perform the engaging at a predetermined time.

According to some embodiments of the invention, the method further comprises: commanding the control device to perform the engaging.

According to some embodiments of the invention, the method further comprises: sensing an event and wherein the engaging is in response to the sensing.

According to an aspect of some embodiments of the invention, there is provided a method of transdermal drug administration to a subject comprising: supplying a transdermal drug patch having an active zone for administering the drug at least partially engaged to the subject and a patch control device, the patch certified for administering a drug to the subject over a prescribed time period; disengaging the active zone from the subject with the device after less than 80% of the time period.

According to some embodiments of the invention, in the partially engaged state at least a portion of the active zone is in contact with a skin of the subject and wherein the disengaging includes distancing the active zone to at least 1 mm from the skin.

According to some embodiments of the invention, the method further comprises: reengaging the active zone at least 20 minutes after the disengaging.

According to some embodiments of the invention, the disengaging includes reducing an area of contact of the active zone of the patch and a skin of the subject by at least 50%.

According to some embodiments of the invention, the disengaging includes peeling a portion of the patch off a skin of the subject.

According to some embodiments of the invention, a separation line of the peeling is a line of contact of a roller.

According to some embodiments of the invention, the method further comprises: storing at least a portion of the patch rolled around a roller.

According to some embodiments of the invention, the method further comprises: storing at least a portion overlying a second portion of the patch.

According to some embodiments of the invention, the method further comprises: positioning a liner between the at least a portion and the second portion.

According to some embodiments of the invention, the method further comprises: programming the control device to perform the disengaging at a predetermined time.

According to some embodiments of the invention, the programming is prior to the supplying.

According to some embodiments of the invention, the method further comprises: sensing an event and wherein the disengaging is in response to the sensing.

According to some embodiments of the invention, the event is a reaction to of the subject to the drug.

According to some embodiments of the invention, the method further comprises: commanding the control device to perform the disengaging.

According to some embodiments of the invention, the commanding includes transmitting a wireless signal to the control device.

According to an aspect of some embodiments of the invention, there is provided a method for loading a transdermal drug administration control device comprising: supply transdermal drug administration patch with an active surface configured to administer the drug to a skin of a subject and approved for administering a dosage according to a fixed schedule; attaching a passive portion of the patch not on the active surface to an adapter; and connecting the adaptor to the device.

According to some embodiments of the invention, the passive portion of the adapter includes an edge, the method further comprising: inserting the edge into a slit in the device.

According to some embodiments of the invention, the attaching to a ventral face of the adapter a dorsal face of the adapter is connected to the device.

According to some embodiments of the invention, the method further comprises: adhering the dorsal face of the adapter to the device.

According to some embodiments of the invention, the device includes a roller and wherein the attaching is to the roller.

According to some embodiments of the invention, the method further comprises rolling the adapter onto the roller.

According to some embodiments of the invention, the adaptor includes a continuous belt connected by rollers to the device.

According to some embodiments of the invention, the method further comprises rolling the belt until the active surface is covered by the device.

According to some embodiments of the invention, the adapter includes a mobile portion and a stationary portion and wherein the attaching to the mobile portion and wherein the control device includes an applicator that moves with respect to a frame, the method further comprising: linking the mobile portion to the applicator and attaching the stationary portion to the frame.

According to some embodiments of the invention, the patch includes a mobile portion comprising a strip and wherein the attaching to the mobile portion and wherein the control device includes an applicator that moves with respect to a frame, the method further comprising: connecting a first location on the strip to a first point on the frame and connecting a second location on the strip to a second point on the frame and wherein a distance between the first point and the second point is less than the length of the strip between the first location and the second location and linking a the strip to the applicator between the first location and the second location.

According to some embodiments of the invention, the connecting includes connecting a leading edge of a mobile portion of the adapter to a roller of the device.

According to some embodiments of the invention, the method further comprises lay out the adapter onto a supporting media and wherein the connecting is while the adapter is lying on the media.

According to some embodiments of the invention, the supporting media includes a skin of a subject and wherein the active surface is placed directly against the skin.

According to some embodiments of the invention, the supporting media includes an alignment device, the method further comprising: fitting the adapter to the alignment device in a fixed orientation and fitting the adapter device to the alignment device in a fixed orientation.

According to some embodiments of the invention, the method further comprises: rolling up the adapter onto roller in disengaged state and attach device to skin in disengaged state.

According to some embodiments of the invention, the method further comprising: placing the control device with the adapter onto a skin of a subject in engaged state.

According to some embodiments of the invention, the supporting media includes an alignment device, the method further comprising: guide the control device with the alignment device into attachment with the adapter.

According to an aspect of some embodiments of the invention, there is provided a transdermal drug patch comprising: an active surface on a ventral face thereof, the active surface configured to administer the drug to a skin of a subject; and a portion of the not included the active surface configured for connecting to a patch control device.

According to some embodiments of the invention, the patch further comprises: a mobile strip including the active surface.

According to some embodiments of the invention, the mobile strip includes a connector on a free end portion thereof.

According to some embodiments of the invention, the free end portion is surrounded on three sides by a discontinuity.

According to some embodiments of the invention, the patch further comprises: a stationary portion a least partially surrounding the strip on at least two sides thereof.

According to some embodiments of the invention, the stationary portion is separated from the strip along a portion of at least on edge thereof by the discontinuity.

According to some embodiments of the invention, the stationary portion includes an adhesive on a dorsal face configured for adhering to the device.

According to some embodiments of the invention, the stationary portion includes an adhesive on a ventral face configured for adhering to skin.

According to some embodiments of the invention, the connector includes an adhesive on a dorsal face of the free end portion.

According to some embodiments of the invention, an end of the strip is connected to a stationary portion of the patch.

According to some embodiments of the invention, an end of the strip opposite the free end is connected to a stationary portion of the patch.

According to some embodiments of the invention, the strip includes a non-reactive covering on a dorsal face thereof.

According to an aspect of some embodiments of the invention, there is provided a system including a patch and an alignment device fitting the patch and the patch control device in a specific orientation for mounting the patch to the control device.

According to some embodiments of the invention, the alignment device includes a blister package containing the patch.

According to an aspect of some embodiments of the invention, there is provided an adaptor for a transdermal drug patch comprising: an attachment surface configured to attach to a dorsal face of a transdermal drug patch; and a portion of the adaptor not included the attachment surface configured for connecting to a transdermal patch control device a mobile strip including the attachment surface.

According to some embodiments of the invention, the mobile strip includes a connector on a free end portion thereof.

According to some embodiments of the invention, the free end portion is surrounded on three sides by a discontinuity.

According to some embodiments of the invention, the adaptor further comprises: a stationary portion a least partially surrounding the strip on at least two sides thereof.

According to some embodiments of the invention, the stationary portion is separated from the strip along a portion of at least on edge thereof by the discontinuity.

According to some embodiments of the invention, the stationary portion includes an adhesive on a dorsal face configured for adhering to the device.

According to some embodiments of the invention, the stationary portion includes an adhesive on a ventral face configured for adhering to skin.

According to some embodiments of the invention, the connector includes an adhesive on a dorsal face of the free end portion.

According to some embodiments of the invention, an end of the strip is connected to a stationary portion of the adaptor.

According to some embodiments of the invention, an end of the strip opposite the free end is connected to a stationary portion of the adaptor.

According to some embodiments of the invention, the strip includes a non-reactive covering on a dorsal face thereof.

According to an aspect of some embodiments of the invention, there is provided a system including an adaptor and an alignment device fitting the adaptor and the control device in a specific orientation for mounting the adaptor to the control device.

According to an aspect of some embodiments of the invention, there is provided a system including an adaptor and an alignment device fitting the adaptor and the transdermal patch in a specific orientation for mounting the adaptor to the transdermal patch.

According to some embodiments of the invention, the alignment device includes a blister package containing the adaptor.

According to some embodiments of the invention, the alignment device includes a blister package containing the transdermal patch.

According to some embodiments of the invention, the discontinuity is configured to allow movement of a point on the mobile region away from a point in the stationary region such that a minimum distance between the points may be at least 2 mm greater than a minimal distance between the points along a surface including the two points without stretching the patch.

According to an aspect of some embodiments of the invention, there is provided a method for loading a transdermal drug administration control device comprising: supply transdermal drug administration patch with an active surface configured to administer the drug to a skin of a subject; attach a passive portion of the patch not on the active surface to the device.

According to some embodiments of the invention, the passive portion of the patch includes an edge, the method further comprising: inserting the edge into a slit in the device.

According to some embodiments of the invention, the active portion of the patch is on a ventral face of the patch and the passive portion of the patch includes dorsal face of the patch.

According to some embodiments of the invention, the method further comprises: adhering the dorsal face of the patch to the device.

According to some embodiments of the invention, the device includes a roller and wherein the attaching is to the roller.

According to some embodiments of the invention, the method further comprises rolling the patch onto the roller.

According to some embodiments of the invention, the device includes a continuous belt and wherein the attaching is to the continuous belt.

According to some embodiments of the invention, the method further comprises rolling the belt until the active surface is covered by the device.

According to some embodiments of the invention, the patch includes a mobile portion and a stationary portion and wherein the control device includes an applicator that moves with respect to a frame, the method further comprising: linking the mobile portion to the applicator and attaching the stationary portion to the frame.

According to some embodiments of the invention, the patch includes a mobile portion comprising a strip and wherein the control device includes an applicator that moves with respect to a frame, the method further comprising: attaching a first location on the strip to a first point on the frame and attaching a second location on the strip to a second point on the frame and wherein a distance between the first point and the second point is less than the length of the strip between the first location and the second location and linking a the strip to the applicator between the first location and the second location.

According to some embodiments of the invention, the attaching includes attaching a leading edge of a mobile portion of the patch to a roller of the device.

According to some embodiments of the invention, the method further comprises lay out the patch onto a supporting media and wherein the attaching is while the patch is lying on the media.

According to some embodiments of the invention, the supporting media includes a skin of a subject and wherein the active surface is placed directly against the skin.

According to some embodiments of the invention, the supporting media includes an alignment device, the method further comprising: fitting the patch to the alignment device in a fixed orientation and fitting the control device to the alignment device in a fixed orientation.

According to some embodiments of the invention, the method further comprises: rolling up the patch onto roller in disengaged state and attach device to skin in disengaged state.

According to some embodiments of the invention, the method further comprises: placing the control device with the patch onto subject in an engaged state.

According to some embodiments of the invention, the supporting media includes an alignment device, the method further comprising: guide the control device with the alignment device into attachment with the patch.

According to an aspect of some embodiments of the invention, there is provided a control system for transdermal administration of a drug to a subject comprising: a flexible substrate; an active transdermal drug administration zone on a ventral surface of the substrate; a roller positioned to roll over a dorsal surface of the substrate, the substrate interposed between the roller and a skin of a subject.

According to some embodiments of the invention, the roller is positioned over a separation line dividing between an engaged portion of the substrate contacting the skin and a disengaged portion of the substrate distanced from the skin.

According to some embodiments of the invention, the system further comprises: a driver for moving the roller and a position of the separation line with respect to the active zone.

According to some embodiments of the invention, the disengaged portion is lifted off of the skin to at least partially wrap around the roller.

According to some embodiments of the invention, the disengaged portion of is wrapped around the roller.

According to some embodiments of the invention, the system further comprises a frame and wherein an end of the engaged portion is connected to a first location on the frame.

According to some embodiments of the invention, the system further comprises a frame including a track and wherein the roller moves along the track to between the first location and an opposite end of the frame.

According to some embodiments of the invention, the disengaged portion of is wrapped in at least two layers around the roller.

According to some embodiments of the invention, the roller includes a friction wheel and the frame includes a friction track and wherein the friction wheel rotates the roller as the roller rolls on the substrate to wind the substrate around the roller at a rate equal to a linear movement of the roller.

According to some embodiments of the invention, an end of the disengaged portion is attached to the roller.

According to some embodiments of the invention, an end of the disengaged portion is connected to the opposite end of the frame.

According to some embodiments of the invention, the substrate includes a continuous belt.

According to some embodiments of the invention, the active zone includes a regulatorily approved fixed dose patch having a dorsal side attached to a ventral side of the continuous belt.

According to some embodiments of the invention, the system further comprises: a driver operative to move the active zone to one or more of a plurality of operational relationships with a skin of a patient, the operational relationships including being in full contact with the skin, partial contact with the skin, and no contact with the skin.

According to some embodiments of the invention, the assembly further comprises a controller that controls the driver, the controller operative to control when and for how long the active zone is in one or more of the operational relationships with the skin.

According to some embodiments of the invention, the substrate further comprises a secondary zone without the drug.

According to some embodiments of the invention, the secondary zone comprises a stratum corneum resurfacing element.

According to some embodiments of the invention, the driver is operatively linked to move the substrate via a friction drive.

According to some embodiments of the invention, the driver is operatively linked to move the substrate via a gear drive.

According to some embodiments of the invention, the stratum corneum resurfacing element comprises an adhesive surface operative to attach to and peel a portion of stratum corneum.

According to some embodiments of the invention, the stratum corneum resurfacing element comprises a chemical operative to peel a portion of stratum corneum.

According to some embodiments of the invention, the stratum corneum resurfacing element comprises a microneedle array.

According to an aspect of some embodiments of the invention, there is provided a method for transdermal substance delivery comprising: using a driver to move a transdermal patch to one or more of a plurality of operational relationships with a skin of a patient, the operational relationships including being in full contact with the skin, partial contact with the skin, and no contact with the skin.

According to some embodiments of the invention, the method further comprises controlling when and for how long the patch is in one or more of the operational relationships with the skin.

According to some embodiments of the invention, the controlling is done with wireless or cellular communication.

According to some embodiments of the invention, the controlling is timed in accordance with circadian rhythms of the patient or circadian rhythms of a disease.

According to an aspect of some embodiments of the invention, there is provided an assembly comprising: a substrate including an active zone comprising a substance adapted for transdermal delivery; and a driver operative to switch the active zone to one or more of a plurality of operational relationships with a skin of a patient, the operational relationships including being in full engagement with the skin, partial engagement with the skin, and no engagement with the skin.

According to some embodiments of the invention, the assembly further comprises a controller that controls the driver, the controller operative to control when and for how long the active zone is in one or more of the operational relationships with the skin.

According to an aspect of some embodiments of the invention, there is provided a control system for transdermal administration of a drug to a subject comprising: an active transdermal drug administration zone; a ductile applicator substrate, having at least two states: an engaged state pressing the active zone against a skin of the subject a disengaged state.

According to some embodiments of the invention, the active zone is on a ventral face of the applicator.

According to some embodiments of the invention, in the disengaged state, the ventral face of the applicator curls dorsally away from the skin with respect to a contact zone between the applicator and the skin.

According to some embodiments of the invention, the control system further comprises: a frame with a contact surface shaped to contact the skin and wherein in the disengaged state the applicator holds the active zone retracted distally with respect to the contact zone and in the engaged state the applicator holds the active zone extended ventrally with respect to the disengaged state.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 6 is a block diagram illustrating further optional features of a device for controlling engagement of a drug patch in accordance with an embodiment of the current invention;

FIGS. 21A-21D illustrate a transdermal control device in accordance with an embodiment of the current invention;

DESCRIPTION OF SPECIFIC EMBODIMENTS OF THE INVENTION

Figure 1:
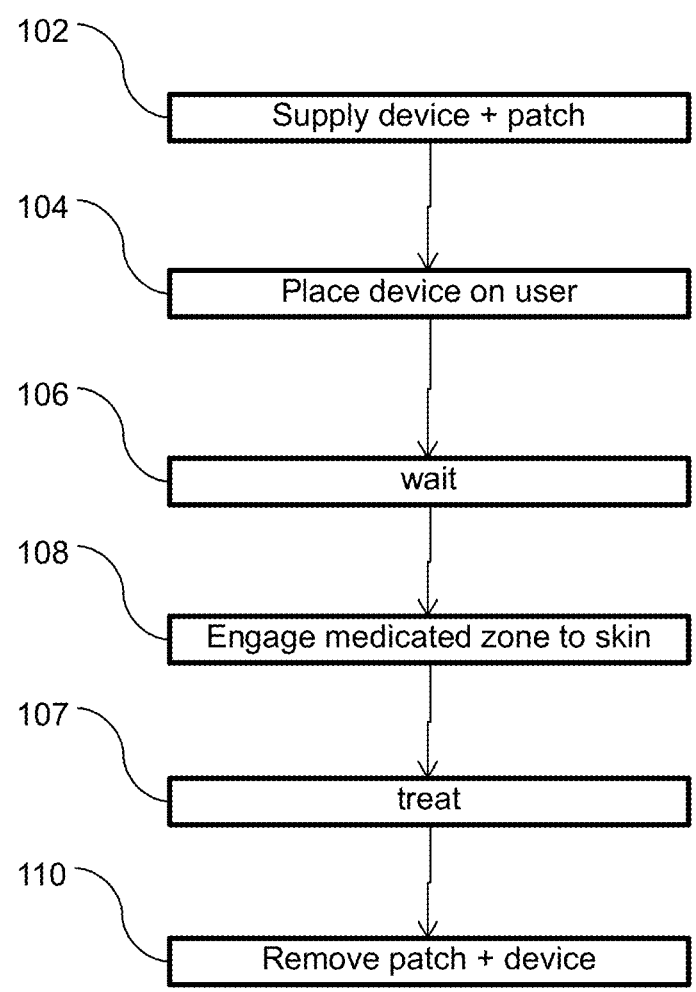
FIG. 1 is a flow chart illustrating a method of delayed engagement of a active surface of a medicine patch in accordance with some embodiments of the present invention.

The present invention, in some embodiments thereof, relates to a system to control transdermal delivery and, more particularly, but not exclusively, to a system to control timing, rate and/or dosage of transdermal delivery from a conventional drug patch and/or a customized drug patch.

Overview

An aspect of some embodiments of the current invention relates to an assembly for controlling timing and/or rate of transdermal delivery that optionally controls drug delivery from a conventional transdermal drug patch. Optionally the system may be used to automatically stop and/or slow delivery of a drug from a transdermal patch.

In some embodiments the device may control delivery from a convention patch approved by a regulatory agency (for example the U.S. Food and Drug Administration FDA and/or the European Commission CE) for a fixed and/or predetermined delivery rate schedule and/or dosage of a drug. For example, in some embodiments, a method and/or apparatus according to the current invention may facilitate use of the patch for delivery of a dose less than the approved dosage and/or at a delivery rate slower than the approved rate.

In some embodiments, delivery may be interrupted before the approved dose has been delivered. Optionally, interrupting delivery may include discontinuing delivery temporarily, discontinuing delivery permanently, and/or reducing a rate of delivery with respect to a predetermined and/or fixed rate schedule of a patch. For example, delivery may be automatically interrupted after less than 1% of the approved dose has been administered and/or after delivery of between 1 to 10% and/or between 10 to 30% and/or between 30 to 50% and/or between 50 to 70% and/or between 70 to 90% of the approved dosage. For example, interrupting delivery may include stopping delivery and/or reducing delivery to a rate less than 1% of an approved rate at a given time after application and/or less than 10% and/or between 10 to 30% and/or between 30 to 50% and/or between 50 to 70% and/or between 70 to 90%.

In some embodiments, interruption of delivery is made automatically, for example, without human supervision and/or intercession after applying of the drug patch. Optionally, delivery is made automatically according to preprogramming prior to and/or during use of the device Optionally, a conventional and/or fixed dose and/or regulatory approved patch may be used to administer a drug without any material intervening between the skin and an active surface of the patch and/or without modifying the drug delivery mechanism of the patch. For example, the conventional and/or fixed dose and/or regulatory approved patch may be used to administer a drug without requiring any regulatorily significant substance intervening between the patch and the skin and/or without compromising the approved drug delivery mechanism of the patch.

In some embodiments a dosage schedule and/or a schedule of patch engagement and/or disengagement, and/or control logic (e.g. in reaction to sensors) may be programmed into a device by a supplier of the device and/or a supplier of the drug, for example before distribution. Alternatively a device may be programmed by a medical professional and/or a personal aid and/or a pharmacist and/or the subject before use. Alternatively a device may be programmed by a medical professional and/or a personal aid and/or a pharmacist and/or the subject dynamically and/or during use.

An aspect of some embodiments of the current invention relates to initiating and/or increasing a rate of administering of a transdermal drug automatically. For example, administration may be initiated more than ½ hour and/or between ½ hour and 2 hours and/or between 2 hours and 8 hours and/or between 8 hours and 24 hours after human intercession or supervision (for example after the system has been placed on a subject). For example, administration may be initiated in response to an event and/or at a fixed time. For example, administration may be initiated while a subject is asleep and/or incapacitated. For example administration may be initiated without supervision and/or without the presence of a helper and/or medical aid.

In some embodiments transdermal drug administration may be automatically initiated from a conventional and/or fixed dosage and/or fixed rate schedule patch. For example, after automated initiation of delivery, transdermal delivery may occur from the patch in accordance to convention regulatory conditions. For example, there may be no regulatorily significant modification to the drug administering portion of the patch. For example, there may be no regulatorily significant intervening substance between the patch and the skin of the subject. Optionally initiation of drug delivery may include switching from no significant delivery to delivery of a significant quantity of the drug. For example, a significant quantity of a drug may include administration at a regulatorily approved rate from a convention drug patch and/or between 50 to 100% of the approved rate and/or between 10 to 50% of the approved rate. In some embodiments initiating delivery may include a significant increase of a rate of delivery. Increasing a rate of delivery may include increasing a rate to between 120% to 150% and/or between 150 to 200% and/or between 200 to 400% more than 400% the rate previous to the increase. For example the rate may be defined as the rate averaged over 1 minute and/or over 5 minutes and/or over ½ hour.

In some embodiments, transdermal drug administration may be initiated and/or increased in rate and/or interrupted and/or reduced in rate in response to an event. For example, a sensor may sense an event and trigger a change in the administration. In some embodiments, the change may take place automatically. For example, the sensor may sense a medical condition, for example a change in cardiac function and/or breathing and/or temperature and/or a reaction to a drug. A patch control device may change the administration in response to output of the sensor. For example, sensor output may be received by a processor that may send a signal to a driver to change the drug administration. For example, a sensor may sense a reaction to a drug and send a signal to a processor which may respond by sending a command to interrupt and/or reduce drug administration. For example, a sensor may sense a medical condition requiring a treatment and send a signal to a processor which may respond by sending a command to initiate and/or increase drug administration. For example, a control device may engage a Nicotine patch to increase the Nicotine level in the blood just before a subject a wakes of. In some embodiments, automatically administering Nicotine before wake up may help reduce morning craving for a cigarette. For example, the wakeup time may be fixed slightly before an alarm time set on an alarm clock (for example a wake up alarm of a smart phone). Alternatively or additionally, wake up may be determined by a sensor sensing body movements and/or vital signs. In some embodiments, applying the patch and/or administering a drug close to the time when it is needed may increase the effect of the drug without increasing the dosage. In some embodiments, administering the drug close to the time of need may facilitate reduction of dosage and/or reduce the habituation effect of high levels of drug administration and/or reduce the risk for over dose.

In some embodiments, a conventional patch may include a passive delivery mechanism. For example, a convention transdermal patch may include a drug-in-adhesive monolithic patch and/or a drug-in-adhesive multilaminate patch and/or a liquid reservoir patch and/or a polymer matrix patch. The patch optionally may be based on a reservoir system and/or a matrix system with and/or without a rate controlling membrane.

An aspect of some embodiments of the current invention relates to automated engaging and/or disengaging of a transdermal drug patch. In some embodiments, an apparatus may automatically engage and/or disengage a drug patch at a fixed time and/or in response to an event. Alternatively or additionally, the apparatus may engage and/or disengage the patch in response to a command.

In some embodiments, the apparatus moves the patch to one or more of a plurality of operational relationships with the skin of the subject (for example a patient). For example, operational relationships may include the patch and/or an active surface of the patch being in full engagement with the skin (i.e., the entire active surface of patch is in contact with the skin), being in partial engagement with the skin (i.e., only a portion of the active surface of patch is in contact with the skin), and being disengaged from the skin (e.g. the active surface of the patch is not in contact with the skin).

In some embodiments, the assembly uses any commercially available transdermal patch impregnated or otherwise provided with a substance. For example, the system can use an existing approved transdermal patch from an approved patch supplier with the previously unknown feature of controlled time of initiation of delivery, breaks in delivery, changes in rate of delivery and/or cessation of delivery.

In some embodiments, the device may disengage a patch by moving an active surface of the patch and/or a portion thereof away from a skin of the subject. For example the active surface may be moved between 0.1 and 1 mm away from the skin and/or between 1 mm and 5 mm and/or between 5 mm and 2 cm and/or more.

In some embodiments, a patch may be peeled from the skin and/or an edge of a patch maybe peeled from the skin. As used herein, the term/phrase peel means to remove and/or lift a covering (e.g. a patch and/or a substrate) from a surface (for example skin) along a line and/or curve (the line or curve will be referred to as a separation line) progressively. As used herein, the term/phrase peel an edge means to remove and/or lift a covering from a surface along a separation line progressively and wherein there is a path from the separation line to an edge of the covering along a separated portion of the covering. As used herein, the term/phrase peel from an edge means to remove and/or lift a covering from a surface along a separation line and wherein there is a path from the separation line to an edge of the covering along a separated portion of the covering and the separation line progresses away from the edge. For example the separation line may progress away from a peeled edge.

In some embodiments, the patch may be engaged by placing on the skin progressively. For example a separation line may serve as a connecting line and may progress from a connected edge toward a separated edge. Optionally, a roller may roll across a patch to separate it or join it to the skin. For example, the separate line may be the line of contact where the patch is sandwiched between the roller and the skin.

In some embodiments a patch may be peeled and/or an edge of the patch may be peeled and/or the patch may be peeled from an edge thereof from the skin. For example, an edge of the patch may be connected to a control device and/or a puller mechanism. Optionally, the active surface of the patch may be lifted progressively off the skin. In some embodiments a patch may be raised off the skin by expanding a variable thickness mesh interceding between the patch and the skin.

In some embodiments a patch may be stored. Optionally the patch may be stored in a disengaged state, for example with an active surface of the patch distanced from the skin of the subject. For example, a patch may be stored rolled onto a roller and/or in a space in a housing and/or covered by a protective liner.

In some embodiments, the system of the invention may engage a patch by applying it to the skin and/or disengage a patch by peeling the patch from the skin. Engaging and/or disengaging may occur at certain times for certain time durations. For example a patch may be engaged and/or disengaged while the user is asleep or incapacitated. In some embodiments, the rate of drug administration may be increased by increasing the active area of the patch in contact with the skin. In some embodiments, the rate of drug administration may be decreased by decreasing the active area of the patch in contact with the skin. The total amount of substance administered is optionally controlled by independently controlling of the time and rate of delivery.

In some embodiments, a patch may have various zones. Disengaging an active surface may include moving the patch such that the active surface is no longer in contact with the skin and/or moving the patch such that a secondary zone contacts the skin. Optionally the secondary zone will contact the same region and/or a different region than the active surface. In some embodiments, an active surface may be partially engaged. For example engaging the active surface and/or increasing the rate of drug delivery may be achieved by increasing the surface area of contact between the active surface and the skin. For example disengaging the active surface and/or decreasing the rate of drug delivery may be achieved by decreasing the surface area of contact between the active surface and the skin.

In some embodiments, a secondary region may be a passive region (e.g. without a drug). Alternatively a secondary region may include a different dosage and/or a different drug and/or different treatment means than the active region. In some embodiments, a patch and/or a substrate may include multiple regions with different drugs and/or treatments. In some embodiments, different zones may contact the skin sequentially and/or in an arbitrary order (for example determined by a command and/or programming of a controller) and/or simultaneously. Optionally a zone may be engaged reversible and/or stored and/or protected during storage and/or reengaged. Optionally reengaging a zone may include reversing a driver and/or a zone may be reengaged by a cyclic system (for example a continuous belt). In some embodiments, a device will progressively engage more active area of a patch, for example to maintain a steady and/or constant dosage.

In some embodiments a conventional patch may be repeatedly engaged and/or disengaged. For example a patch may be engaged and/or disengaged once and/or between 2 to 3 times and/or between 4 to 6 times and/or more. Alternatively or additionally, a patch may be modified for enhanced reapplication. For example, a patch may use a gel instead of and/or in addition to a conventional adhesive to hold the patch in place. In some embodiments gel may enhance reengaging of the patch. For example, a gel patch may be engaged and/or disengaged between 1 to 3 times and/or between 4 to 6 times and/or between 7 to 10 times or more.

In some embodiments, a control device may exert a force relative to a patch and the skin of the subject. For example, an actuator may be connected to a frame. The actuator optionally moves with respect to the frame. Optionally the actuator is connected to a mobile portion of the patch. In some embodiments the frame is attached to the skin of the subject. Optionally, an immobile portion of the patch may attach the frame to the skin. A force between the frame and the actuator optionally results in a force and/or movement of the patch with respect to the skin. Optionally, a driver may exert the force between the frame and the actuator.

In some embodiments a patch control device includes a frame and a roller. In some embodiments, one portion of the patch, for example a leading edge of a mobile section thereof, may be attached to a roller. For example, a stationary portion of the patch may be attached to a frame of the device. For example, a trailing edge of the mobile portion of the patch may be connected to the immobile portion of the patch.

In some embodiments a length of a device may range for example between 5 to 25 mm and/or between 25 to 60 mm and/or between 60 to 90 mm and/or between 90 to 120 mm and/or between 120 to 200 mm and/or greater than 200 mm. In some embodiments a width of a device may range for example between 10 to 50% and/or between 50 to 75% and/or between 75 to 125% and/or between 125 to 200% and/or between 200 to 400% and/or between 400 to 1000% its length. For example, the ventral surface area and/or skin contact surface area of a device may range between 100 to 130% and/or between 130% to 250% and/or between 250% to 500% the area of a ventral surface of a patch to be controlled. For example the device may control a patch of length between 5 to 25 mm and/or between 25 to 60 mm and/or between 60 to 100 mm and/or between 100 to 200 mm. In some embodiments a width of a patch may range for example between 10 to 50% and/or between 50 to 75% and/or between 75 to 125% and/or between 125 to 200% and/or between 200 to 400% and/or between 400 to 1000% its length. For example a patch may include a 70×70 mm or 50×50 mm or 35×35 mm patch. Exemplary patches include Nicotrol of GSK and/or Nicoretee and/or Nicoderm. For example a patch may be rated at a fixed dose of about 5, 10, or 15 or 22 mg/day over 16-24 hrs. In some embodiments, a controller will initiate the drug delivery for example between 5 minutes to an hour and/or between an hour and 2 hours and/or between 2 hours and 4 hours and/or between 4 hours and 8 hours and/or between 8 hours and 16 hours and/or between 16 hours and 24 hours after attaching the system to the subject. In some embodiments, the device will move a patch from a disengaged state to an engaged state in a time ranging between 1 seconds to 10 seconds and/or between 10 seconds to 30 seconds and/or between 30 seconds and 90 seconds and/or between 90 seconds and 2 minutes and/or between 2 minutes and 1 hour. Alternatively or additionally, a device may slowly engage a patch over a time ranging between an hour to 4 hours and/or 4 hours to 12 hours and/or 12 hours to 24 hours and/or 24 hours to a week. For example slowly engaging a patch may keep a constant rate of delivery over a period. In some embodiments, drug delivery may start immediately up to a full dose. In some embodiments, the device will move a patch from a engaged state to a disengaged state in a time ranging between 1 seconds to 10 seconds and/or between 10 seconds to 30 seconds and/or between 30 seconds and 90 seconds and/or between 90 seconds and 2 minutes and/or between 2 minutes and 1 hour. For example, disengagement may include pulling a patch from the skin. For example, disengagement may take 10 to 60 seconds if using a motor or 1 to 5 seconds using a preloaded spring and/or gas pressure.

In some embodiments, disengaging a patch (for example, pulling a patch from the skin) and/or storing the patch, may happened at any stage during the delivery. In some embodiments the patch may be stored for reuse within an approved time. In some embodiments, the patch may be replaced and/or the device reused. Alternatively or additionally the patch and device may be replace together. For example a patch and/or a device may be replaced after a time ranging between 1 hour to 8 hours and/or 8 hours to 16 hours and/or 16 hours to 1 day and/or 1 day to 2 days and/or 2 days to a week.

In some embodiments, a portion of the patch may be stored in a disengaged state. For example, between 0 to 20% and/or between 20 to 50% and/or between 50 to 80% and/or between 80 to 100% of the patch may be stored. For example, between 0 to 20% and/or between 20 to 50% and/or between 50 to 80% and/or between 80 to 100% of a mobile portion of patch may be stored.

In some embodiment a roller may engage and/or disengage a patch. Optionally the patch may be stored rolled up on the roller in a disengaged state. For example the roller may unroll the patch on to the skin engaging the patch. Optionally, the roller may roll along the patch, pulling up the patch along a separation line, peeling the patch off the skin and/or disengaging the patch and/or rolling up the patch onto the roller. Optionally, the separation is the line of contact where the patch is sandwiched between the roller and the skin. Optionally, a roller may serve one, some, or all of the functions described above. For example, a roller may serve one, some, or all of guiding movement of a separation line between a patch and skin, pulling a patch away from skin and/or a separation line, and/or storing a patch.

In some embodiments a roller may be configured to rotate at a rate that varies according to the diameter of the roll of patch being rolled up or unrolled. For example, the rate of rotation may be controlled to let out and/or take up the patch at the same rate as the linear movement of the roll. For example, for a larger roll the rate of rotation of the roller may be adjusted downward with respect to the linear rate of progress of the roller. For example, the roller without the patch may have a diameter ranging between 2 to 6 mm and/or between 6 to 10 mm and/or between 10 to 15 mm and/or between 15 to 25 mm. Optionally the diameter of the roll (including the roller with the patch rolled around it) may range between 0 to 2 mm and/or between 2 to 4 mm and/or between 4 to 6 mm and/or between 6 to 10 mm or between 10 to 20 mm greater than the diameter of the roller alone. For example, a patch may be rolled around a roller in 1 layer and/or 2 to 4 layers and/or 4 to 10 layers and/or 10 to 20 layers.

In some embodiments, a patch may be mounted on a substrate and/or an adaptor. The substrate is optionally driven by a driver. Optionally, the operation of the driver is controlled by a controller. For example, the controller may control when and for how long the patch is in a particular operational relationship with the skin (e.g., at what time of the day is the patch in full, partial or no contact with the skin and for what duration of time). Alternatively or additionally, the substrate may be arranged to determine a timing or dosage of the medicine. For example, the driver may drive the substrate at a fixed rate and/or active surfaces may be arranged on the substrate such that they are engaged at predetermined times and/or removed at predetermined times. For example, a driver may include a DC motor and/or a stepper motor and/or a linear actuator and/or a rubber band and/or a spring and/or a compressed gas drive. Alternatively or additionally a patch control device may be manually operated.

In some embodiments, the system may be operated based on a real time clock. Alternatively or additionally the system may be operated remotely, for example with a wireless/cellular connection. For example a parent and/or caretaker may use a cellular connector to remotely control drug administration to children or the elderly. For example, a patch may be stored in the assembly in a disengaged state (no substance administration) and then later engaged (that is, moved to an operational position where the substance is delivered) by authorized personnel (e.g., parent or caregiver).

An aspect of some embodiments of the current invention relates to a method for mounting a transdermal drug patch to a control device and/or a substrate and/or an adapter for mounting to the device. In some embodiments a patch may have a stationary portion and/or a mobile portion.

In some embodiments, the mobile portion of the patch may be engaged and/or disengaged to and from the skin by the patch control device. For example, a mobile portion of the patch may include one or more active and/or inactive surfaces and/or zones. Optionally a stationary portion of a patch may include an inactive zone. Alternatively or additionally a stationary portion of the patch may include one or more active surfaces. Optionally, a stationary portion of the patch may be held continuously engaged to the skin. Alternatively or additionally a stationary portion of the patch may be held continuously distanced away from the skin.

In some embodiments a patch may be attached to a substrate and/or an adaptor. For example, an active surface of the patch may be attached to a mobile portion of the adaptor. Optionally, the mobile portion of the adapter may be engaged and/or disengaged to and from the skin by the patch control device. Optionally the adaptor may include a stationary zone. Optionally, part or all of a stationary portion of the adaptor may be held engaged to the skin. Alternatively or additionally part or all of a stationary portion of the adaptor may be held distanced away from the skin.

In some embodiments, a mobile portion of a patch and/or an adaptor may be separable from a stationary portion thereof. For example, a point on the mobile portion may be distanced from a point on the stationary portion by a given distance along the surface of the substrate. When the portions are separated the distance between the points may be increased over the given distance. For example, when the substrate is lying flat on a surface (for example on a flat surface) a point on the mobile portion may be distanced from a point on the stationary portion by a given minimum distance along the surface. When the portions are separated, the minimum distance between the points may be increased over the given distance along the surface between the points when the portions are not separated. Optionally a discontinuity in the patch may intervene between the mobile region and the stationary region. For example the mobile reason may be separated from the stationary region by the discontinuity. For example, the discontinuity may include a cut and/or a cut out. For example the length of the cut and/or cut out may range between 1 to 5 mm and/or between 5 mm to 2 cm and/or between 2 to 5 cm and/or between 5 to 10 cm greater than 10 cm.

In some embodiments the stationary region may fully or partially surround the mobile region. Optionally the stationary region may not be convex. For example there may be two points located in the stationary region such that a line connecting the points along the surface of the substrate passes through the mobile region. For example there may be two points located in the stationary region such that, when the patch is lying flat on a surface a line connecting the points along the surface passes through the mobile region. For example, the minimum distance between a point in the mobile region and a point in the stationary region when separated may range between 1 mm to 5 mm more than the minimum distance between the points along the surface of the substrate when they are not separated and/or between 5 mm to 2 cm more and/or between 2 cm to 5 cm and/or 5 to 12 cm more than the shortest distance between the points along the surface of the substrate when the regions are not separated. For example, the minimum distance between two points when portions of the patch are separated may range between 1 mm to 5 mm more than the minimum distance along a surface onto which the patch is spread when the portions of the patch are not separated and/or between 5 mm to 2 cm more and/or between 2 cm to 5 cm and/or 5 to 12 cm more than the shortest distance between the points along the surface.

In some embodiment a substrate may have an adhesive on two opposite faces. For example there may be adhesive on a ventral side of the substrate for connecting to a skin of a subject and/or there may be adhesive on a dorsal side of the substrate for connection to a control device In some embodiments a discontinuity may intercede between a point on the mobile portion and a point on a stationary portion such that when the patch is laid on a surface, the distant along the surface between the points without crossing the discontinuity is greater than the distance along the surface between the two points along the surface crossing the discontinuity by between 1 mm to 5 mm and/or between 5 mm to 10 mm and/or between 10 to 50 and/or between 50 to 100 mm. A discontinuity may include for example a cut and/or a score and/or a scratch and/or a fold and/or a slit.

In some embodiments an alignment device is supplied to facilitate alignment of a patch and/or an adaptor and/or a patch control device. Alignment may be adjusted, for example, in the lateral and/or longitudinal position and/or angular alignment. For example, achieving accurate longitudinal position may facilitate dosage control when an active surface is only partially engaged. The exact position of a patch on a device and/or on a substrate and/or on an adapter may be monitored. A patch may be optionally attached to a substrate, for example by adhesive, ultrasonic welding, heat etc. For example an alignment device may guide movement of a patch and/or patch controller device as the patch is being mounted of the device. The alignment device may optionally have a contoured surface that holds a part of a patch extended and/or recessed to match a contact service of a control device.

In some embodiments a device may be sized between 70×70 mm to 100×100 mm. Optionally the device is adapted for a large dermal patch. For example the device may control a patch having dimensions up to 70×70 mm. Alternatively the device may control a smaller patch for example 50×50 mm or 35×35 mm and/or of various shapes for example circular shape with diameter range 20 mm-70 mm. Optionally for smaller patches, for example of dimensions between 50×50 mm to 35×35 mm and/or smaller (e.g. for lower doses between 3-10 mg) a device may be smaller, for example between 70×70 mm to 60×60 mm and/or smaller.

In some embodiments a control device may use a force to peel a patch from skin. For example a driver may exert a force on an actuator and/or a puller to puller. For example the force may turn a roller and/or move an actuator. For example, the force may range for example between 0.5 and 1 g per mm of peeling line. For example for a 70×70 mm patch the total force may range between 350 to 700 g. Alternatively or additionally the force may range between 0.1 and 0.5 g per mm peel line and/or between 1 g/mm to 3 g/mm. The force on the patch is optionally balanced by a counter force on the skin of the subject. For example, the driver may be supported on a frame of the device which is optionally attached to and/or supported by the skin of the subject.

An aspect of some embodiments of the current invention relates to protecting a patch while it is being stored in a control device. For example a liner may be supplied to separate between an active surface of the patch and a storage surface. For example, when the patch is rolled up during storage, the liner may separate between a ventral surface of one layer of the patch and a dorsal surface of the previous layer of the patch. Alternatively or additionally a liner may be part of a device. Optionally, the linear may be made of a non-stick and/or non reactive substance. Optionally, the liner may be flexible and/or impermeable.

In some embodiments, a non-reactive material of a layer, coating, surface and/or liner may be compliant against United States Food and Drug Administration (FDA) Code of Federal Regulations (CFR) 21 (for example subsection 175.300 of section 175 and/or subsection 177.1550) and/or European Council (EC) directives and/or regulations for example (EC) 2023/2006 and/or (EC) 1935/2004 and/or (EC) 1272/2008. Optionally the coating is non-oxidizing. Optionally, the material may be dense and/or nonporous for example to prevent growth of mold and/or bacteria. For example the material may produce little or no residual when exposed to water and/or heptanes and/or alcohol (for example 8%) for between 1 to 24 and/or 24 to 150 hours at temperature between −20 to 50 degrees C. and/or between 50 to 100 degrees C. and/or between 100 to 200 degrees C. at normal and/or high pressure. For example residuals may be less than 150 parts per million (ppm) and/or less than 50 ppm and/or less than 2 ppm. For example, a non-reactive material may include Polyethylene and/or paper coated with polyethylene.

In some embodiments, a non-active surface of a patch and/or adapter and/or a ventral surface thereof and/or a ventral surface of a control device and/or a frame of a control device may be attached to skin using nonwoven tape for example 3M 1776. For example, a non-active surface of a patch and/or adapter for example a dorsal surface thereof may be attached to a control device by single and/or double sided adhesive, for example 3M 1522. In some embodiments, a substrate (for example a patch and/or an adaptor) may be configured for connection to a control device. Optionally, a surface and/or an edge of a mobile portion of the substrate may be configured for attachment to the device and/or an actuator thereof. Optionally, a surface and/or an edge of a stationary portion of the substrate may be configured for attachment to the device. For example, a part of a dorsal face of the patch may be connected to the control device. Alternatively or additionally an edge of the patch may be connected to the control device. For example, the attachment may be by means of an adhesive and/or a magnet and/or a clip and/or a hook and/or a slit.

In some embodiments, the mobile portion of the substrate will be configured to attach to an actuator and/or mobile portion of the device and/or be engageable and/or disengageable to the skin of a subject. Optionally the stationary portion of the substrate will be configured to attach to an immobile portion of the device and/or a frame of the device and/or be stationary with respect to the skin of a subject (for example remain engaged and/or disengaged as long as the device is attached).

Some embodiments of the system of the invention may be advantageous in "chronotherapy", in which drug delivery is timed in accordance with a body rhythm, for example a circadian rhythm and/or a rhythm of a disease. In some embodiments, chronotherapy, may increase therapeutic efficacy and/or reduce side effects in comparison to constant delivery. Optionally, dose control may be programmed to deliver redefined doses that coincide with peak disease symptoms. For example, this may be useful when symptoms peak at night while asleep or immediately upon waking.

Circadian rhythms may be described as physical, mental and behavioral changes that follow a roughly 24-hour cycle and/or respond to light and darkness in an organism's environment. Circadian rhythms may is some cases influence sleep-wake cycles, hormone release, body temperature and other important bodily functions. They have been linked to various sleep disorders, such as insomnia. Abnormal circadian rhythms have also been associated with obesity, diabetes, depression, bipolar disorder, seasonal affective disorders, asthma attacks, coronary infarction, angina pectoris, stroke and ventricular tachycardia, among others.

In some embodiments, a control system will not interfere with the active portion and/or action of a drug patch. For example, the device may not interfere with the chemical composition and/or physical properties of some, any or all of the patch reservoir and/or the adhesive and/or the release liner. Optionally changes will occur in aspects of the active portion of the patch due to exposure or protection from contact with skin. For example by removing the active surface from the skin of a subject and/or protecting the active surface, chemicals that would have diffused out of the patch may remain and/or build up and/or change concentration. In some embodiments, the dosage control system does not compromise the active envelope and/or stack of the patch either with energy, chemical and/or physical means. In some embodiments, the dosage control system does not add any intervening substance between the active surface of the patch and the skin of a subject.

In some embodiments a dosage control system may work with a conventional drug patch. For example the drug patch may have a predetermined delivery behavior. Optionally the predetermined delivery behavior may depend on characteristics of the subject and/or his skin. Optionally the active surface of the patch will be substantially uniform over 70% and/or 90% of its surface. For example the patch may not include control regions and/or programmable components and/or a sensor.

In some embodiments, the present invention may be used to facilitate transdermal drug administration of any drug including for example Clonidine, Diclofenac Epolamine, Estradiol, Levonorgestrel, Norethindrone Acetate, Norelgestromin, Ethinyl Estradiol, Fentanyl, Lidocaine, Tetracaine, Methylphenidate, Nitroglycerin, Amlexanox, Oxybutynin, Rifastigmine, Scopolamine, Selegiline, Testosterone, Nicotine, Methyl Salicylate, Menthol, Epinephrine, Rotigotine and/or any combination thereof.

In some embodiments, the present invention may be used to facilitate drug administration with an existing transdermal system, for example Catapres TTS, Flector, Vivelle, Climara, Vivelle-Dot, Alora, Menostar, Estraderm, Climara Pro, Combipatch, Ortho Evra, Duragesic, Lidocaine, Synera, Daytrana, Nitro-Dur, Minitran, Oradisc A, Oxytrol, Exelon Patch, Transderm-Scop, Emsam, Androderm, Nicoderm, Habitrol, Prostep, Salonpas.

Some embodiments of a system according to the current invention may be used to transdermally deliver an active drug (for example propranolol, nifedipine, verapamil, enalapril, isosorbide 5-mononitrate and digoxin, an anti-asthmatic (e.g. theophylline and terbutaline), an anticancer drug, a psychotropic drug, an analgesic, a local anesthetics and/or an antibiotic).

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Delayed Engagement of an Active Surface of a Medicine Patch

Referring now to the drawings, FIG. 1 is a flow chart illustrating a method of delayed engagement of an active surface of a drug patch in accordance with some embodiments of the present invention. In some embodiments, a device is supplied 102 with a drug patch stored 104 in the device. Optionally the device is placed 104 on a user's skin. The patched is then engaged 108 to the user's skin after a delay 106. For example the patch may be engaged 108 by the device according to a preprogrammed time and/or in response to a command and/or in response to an event. When the patch is engaged 108 to the skin of the subject, it optionally treats 107 a condition for example by releasing a drug and/or preparing the skin and/or other treatment. For example that patch may treat the epidermis to improve the drug delivery. Optionally at the end of treatment 107 the device and/or patch may be removed 110 from the subject. Alternatively or additionally the device may disengage the patch and/or engage more active area of the patch (for example as described herein in further embodiments). Alternatively or additionally, the system may be designed to release a measured dose and/or remain active for a limited time and/or cease and/or switch without external intervention.

In some embodiments, a device may be supplied preloaded with a patch from a supplier (for example a drug producer and/or a manufacturer). Optionally the patch may be supplied in a stored state and/or ready to use. For example a user may receive a ready device and/or may place the device on his skin and/or activate the device. Alternatively or additionally, a device may need to be primed before use. For example, a protective liner may be exposed. For example, before placement 104 the liner may be removed by a user. Optionally before placement 104 of the device on a subject, the patch may be moved to a storage position. For example the patch may move to the storage position automatically upon opening a storage container (for example a blister) and/or in response to another step in priming of the device (for example in response removing a protective liner) and/or by a command.

In some embodiments, a patch may be supplied separate from the engagement device. For example, a patch may be included in package with the device and/or supplied entirely separately from the device. Optionally the patch may be packaged in a protective package.

In some embodiments, a patch may be designed for manual placement on the skin without the engagement device, for example a conventional patch. Optionally, an interface may be supplied to connect the patch to the device. Alternatively or additionally, the patch may be connected directly to the device. Alternatively or additionally, a patch may be designed and/or packaged for use with the device. Optionally, the user may remove the patch from a protective wrapper and/or load the patch to the device. Alternatively or additionally, a patch may be an integral part of a cartridge and/or device. For example, the cartridge may be disposable and/or single use while the controller and/or driver may be reused. Alternatively or additionally, the entire device may be disposed of for example with a used patch.

In some embodiments, the device may engage 108 the patch to the subject (for example by putting an active portion of the patch in contact with the skin of the subject). Optionally, engagement 108 may occur after a time delay 106. For example, time delay 106 may be preprogrammed. Alternatively or additionally, engagement 108 may be in response to a command. Alternatively or additionally, engagement 108 may be in response to an event. For example, a sensor may detect a medical condition requiring treatment and the device may respond by engaging 108 the patch. Alternatively or additionally engagement 108 may be in response to compound trigger (for example a sensor may alert a medical professional who may transmit a command to engage 108 the patch and/or a patch may be engaged in response to a certain sensor output only at certain times and/or under certain conditions [for example the patch may be engaged only when a cumulative dosage in a determined time period is with a specific range]).

In some embodiments a patch engaging device may include a logical controller, for example a processor. Optionally the processor will give commands to engage 108 the patch according to preprogrammed instructions and/or received data and/or received commands. Alternatively or additionally a device may progressively meter out a patch having one or more active surfaces. When an active surface is engaged 108 it may perform a treatment 107 for a predetermined period and/or until it is disengaged for example by being removed 110. Optionally, the device may perform the disengagement of the patch (for example as described in various embodiments herein).

In some embodiments, a delayed patch engaging system may be useful for convenience and/or safety. For example, when a subject is to receive a drug at night, a device may engage a patch at a predetermined time without needing to depend on the subject waking up and remembering the drug. In some embodiments, the machine may engage the patch without disturbing the subject's sleep. Alternatively or additionally, the device may be used to engage a patch to a subject who has limited ability of self administration. For example a patch may be engaged to a physically disabled subject and/or a mentally limited and/or senile subject without requiring the presence of a caretaker, for example at an inconvenient time. Alternatively or additionally, a device may be used by a veterinarian to engage a patch to an animal at a prescribed time without needing the veterinarian to be present. Alternatively or additionally, the device may be used to apply a dose to subject under monitoring whenever and/or wherever an acute condition occurs. Alternatively or additionally, a delayed engagement device may be used to maintain a determined dosage. For example as a patch is depleted, the device may progressively engage more of the patch, maintaining a constant dosage and/or the speed of engaging may be controlled to maintain a desired dosage regime (for example through a preprogrammed engaging regime and/or speeding or slowing engagement in response to a sensor). Alternatively or additionally, the device may be used to increase the level of compliance in environments where compliance is a critical and/or problematic (for example treatment of mental patients and/or chemotherapy and/or drug testing). For example use of a delayed patch engagement device may reduce the requirements of subject supervision and/or associated subject time in a hospital and/or clinic. Alternatively or additionally the device may be used for non-medicinal drugs and treatments. For example, a device may engage a patch with a drug against motion sickness to a sleeping subject a few hours before an early morning flight and/or a device may engage a patch including a stimulant a to a subject shortly before he needs to wake up.

Automatic Disengaging of Medicine Patch

Figure 2:
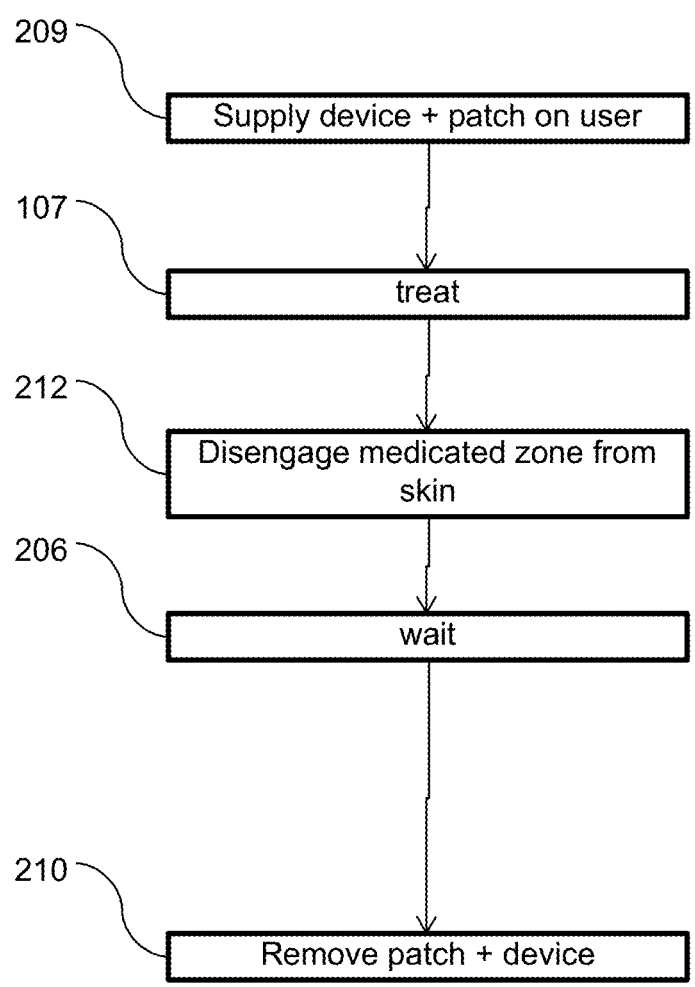
FIG. 2 is a flow chart illustrating a method of disengaging an active surface of a medicine patch in accordance with some embodiments of the present invention.

FIG. 2 is a flow chart illustrating a method of disengaging of a medicine patch in accordance with some embodiments of the present invention. In some embodiments, a device may be used to disengage 212 a drug patch from a subject. For example, a disengagement device may be supplied 209 on a user being treated 107 with a drug patch. Optionally when the treatment should be stopped, the device will disengage 212 the patch from the skin of the subject. Once the patch has been disengaged 212 the device and/or patch may be removed 210 at a convenient time.

In some embodiments, a user may place a device on a subject in an engaged state. The device may leave the patch on during a treatment 107 and then remove the patch. Alternatively or additionally, a machine may be used to perform delayed engagement of a device (for example as described in the previous embodiments) and then to perform disengagement 212. Optionally the user may load the drug and/or prime the device and/or place the device onto the subject. Alternatively or additionally a user may receive a device preloaded and/or preprimed.

In some embodiments, a device may disengage 212 a patch according to a command and/or in response to a condition (for example in response to a sensor signal) and/or at a preprogrammed time. Optionally, a disengagement time may be programmed into a controller of the device, for example a processor. Alternatively or additionally, the device may progressively remove a patch having active surfaces located at predetermined locations along the patch thereby being removed at a predetermined time. The programming is optionally done by a manufacturer and/or by a user. In some embodiments after disengagement 212 of a patch, the patch and/or the device may be removed 210 and/or disposed of. Optionally, removal of the device may be immediate. Alternatively or additionally, removal may be after a time delay 206. Alternatively or additionally disengagement 212 of the patch may be reversible. For example, the device may store the disengaged patch and/or engage the patch after storage (for example as described in various embodiments herein).

In some embodiments a patch disengagement device may be used to reduce subject supervision and/or shorten subject time in a hospital or clinic. For example, a subject who would otherwise be required to remain in a clinic to make sure a patch is properly disengaged, may be administered a patch with a device and sent home. For example a patch disengagement device may be used to prevent accidental overdose due to neglecting to remove a patch. For example, a device may remove a patch at a fixed time before an overdose would occur and/or a device may have a sensor that detects initial signs of an overdose and removes that patch before the overdose. Alternatively or additionally, a patch removal device may be under control of a subject and/or may be used to monitor the use of a medicine patch (for example dosage, timing and/or compliance). Alternatively or additionally a patch removal device may be used to remove a patch at an inconvenient time (for example to remove a sleeping drug patch after a subject has gone to sleep and/or to remove a patch from a subject early in the morning without requiring a subject to get up and/or a caretaker to come).

Controlling of Dosage of a Medicine Patch

Figure 3:
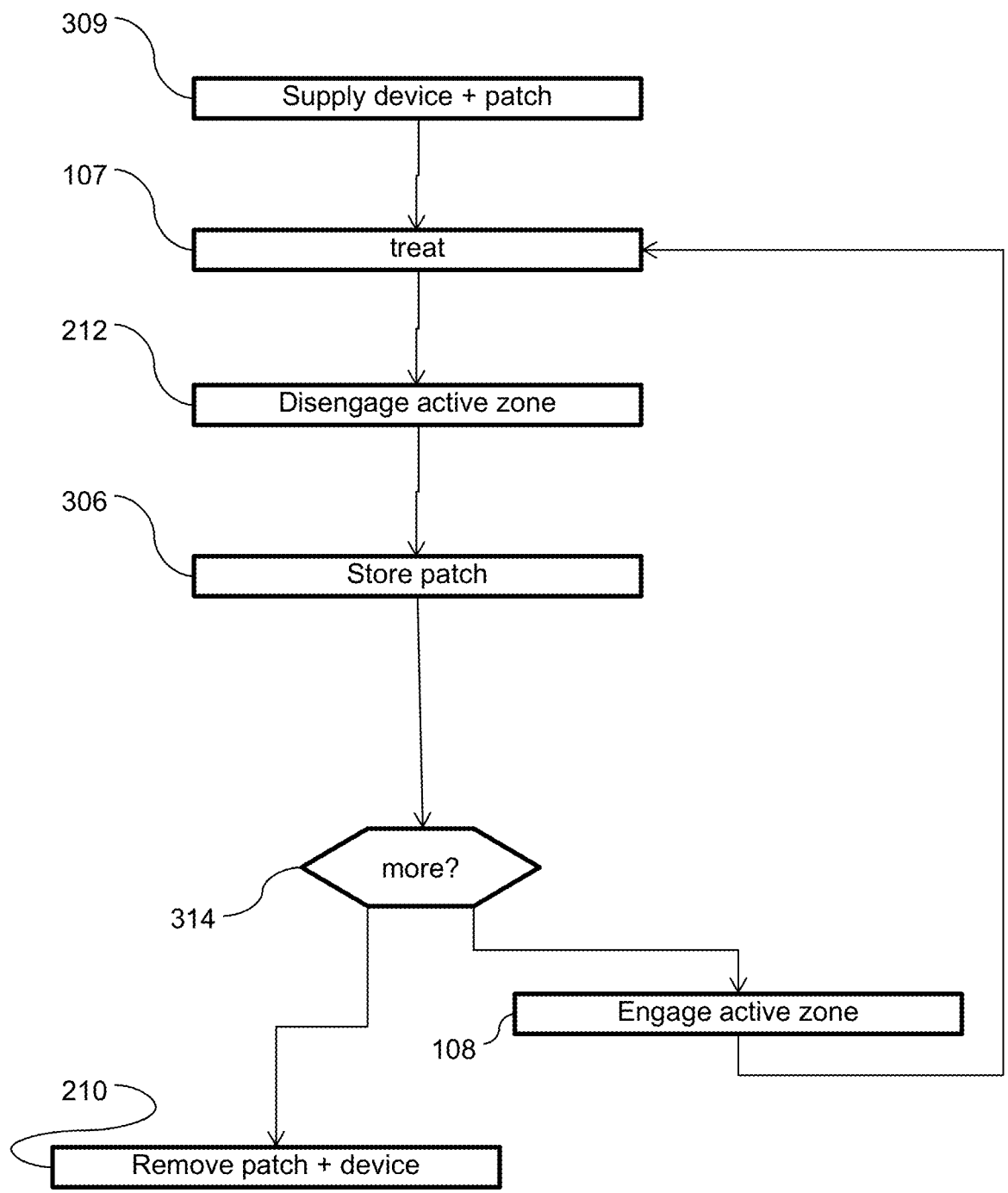
FIG. 3 is a flow chart illustrating a method of reversibly engaging and disengaging an active surface of a medicine patch in accordance with some embodiments of the present invention.

FIG. 3 is a flow chart illustrating a method of reversibly engaging and disengaging of a medicine patch in accordance with some embodiments of the present invention. In some embodiments, a device may reversibly and/or repeatedly engage and/or disengage a medicine patch. For example, a patch may have an active surface for treatment of a subject. The device may repeatedly disengage 212 the active surface from the subject and/or engage 108 the active surface. Optionally, while the active surface is disengaged, it is stored for re-engaging 108. Optionally, before and/or during storage, the patch may be protected for example by placing a liner over an active area of the patch while it is being stored 306. Alternatively or additionally, the patch is stored rolled about itself and/or rolled around a liner or an inflatable mesh. Optionally a patch may be disengaged by blocking contact between the active surface of the patch and the skin.

In some embodiments a patch and or device may be supplied 309 to a subject. Optionally the device may be preloaded. Alternatively or additionally the device may require loading. Optionally the device may be preprimed. Alternatively or additionally the device may require priming. In some embodiments the device will be supplied 309 in an engaged state. For example, treatment 107 may immediately start when the device is placed on the skin of the subject. Alternatively or additionally, the device may be supplied 309 in a disengaged state. For example, treatment 107 and/or engagement 108 of the patch may start after a delay.

In some embodiments, after a period of treatment 107, a patch may be disengaged 212 and/or stored 306. During and/or prior to storage 306, the patch may be protected, for example from contamination and/or depletion. After disengagement, a decision may be made whether to administer more 314 treatment 107. The decision to administer more 314 treatment 107 may optionally be preprogrammed. For example, a processor in the device may be programmed to continue treatment 107 according to a time schedule and/or dependent on a sensor input and/or based on commands communicated to the processor. Alternatively or additionally, the patch may be formed to perform a particular treatment regime. For example, active and/or inactive surfaces may be distributed along the patch such that the device progressively engages and/or disengages various zones at different times. For example, the device may progressively engage and/or disengage parts of the patch. Optionally, according to the configuration of the patch active and/or inactive surfaces may be engaged and/or disengaged.

In some embodiments a reversible patch engaging/disengaging device may be used to maintain a dosage regime and/or medicine concentration over an extended period. For example, maintaining a dosage may compensate for the dosage rate reduction resulting from aging and/or use of the patch, for example a change of drug concentration in the patch due to depletion. For example a control device may be used to set a pharma kinetic level (PK) in the blood. For example fresh patch may be applied and/or a patch may be applied over fresh of skin. For example, fresh application may stabilize the total transfer in spite of degradation in the skin and/or patch.

Device for Controlling Engagement of a Medicine Patch

Figure 4:
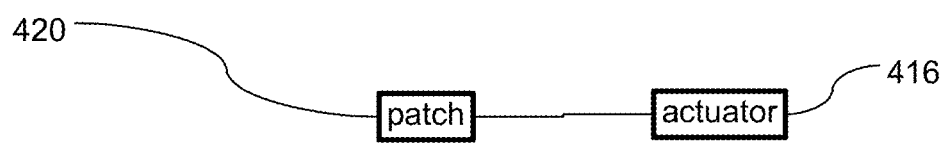
FIG. 4 is a block diagram illustrating a device for controlling engagement of a drug patch in accordance with an embodiment of the current invention.

FIG. 4 is a block diagram illustrating a device for controlling engagement of a drug patch in accordance with an embodiment of the current invention. In some embodiments, a patch controlling device may include an actuator 416. For example actuator 416 may initiate, increase, decrease and/or interrupt administration of a drug from a patch 420. Optionally the patch 420 includes a conventional fixed dose drug patch. Alternatively or additionally a patch may be a custom patch. For example, custom patch may include an active area of a conventional patch, for example approved for use for a fixed dosage mounted on a custom substrate and/or custom periphery.

In some embodiments an actuator may be mobile with respect to a frame and/or a subject contact surface of the device. Optionally, actuator 416 may include a roller. For example a roller may roll a patch onto and/or off of a subject. Alternatively or additionally an actuator 416 may include a substrate (for example a flexible belt and/or a flexible strip and/or a ductile actuator [for example that changes shape to engage and/or disengage a portion of a patch for example substrates 2258 and/or 2458 of FIGS. 22 and 24 respectively].

In some embodiment patch 420 may include a single active region and/or multiple active regions. Optionally, different active regions may have the same drug formulation. Alternatively or additionally different active regions may include different drugs and/or formulations.

Figure 5A:
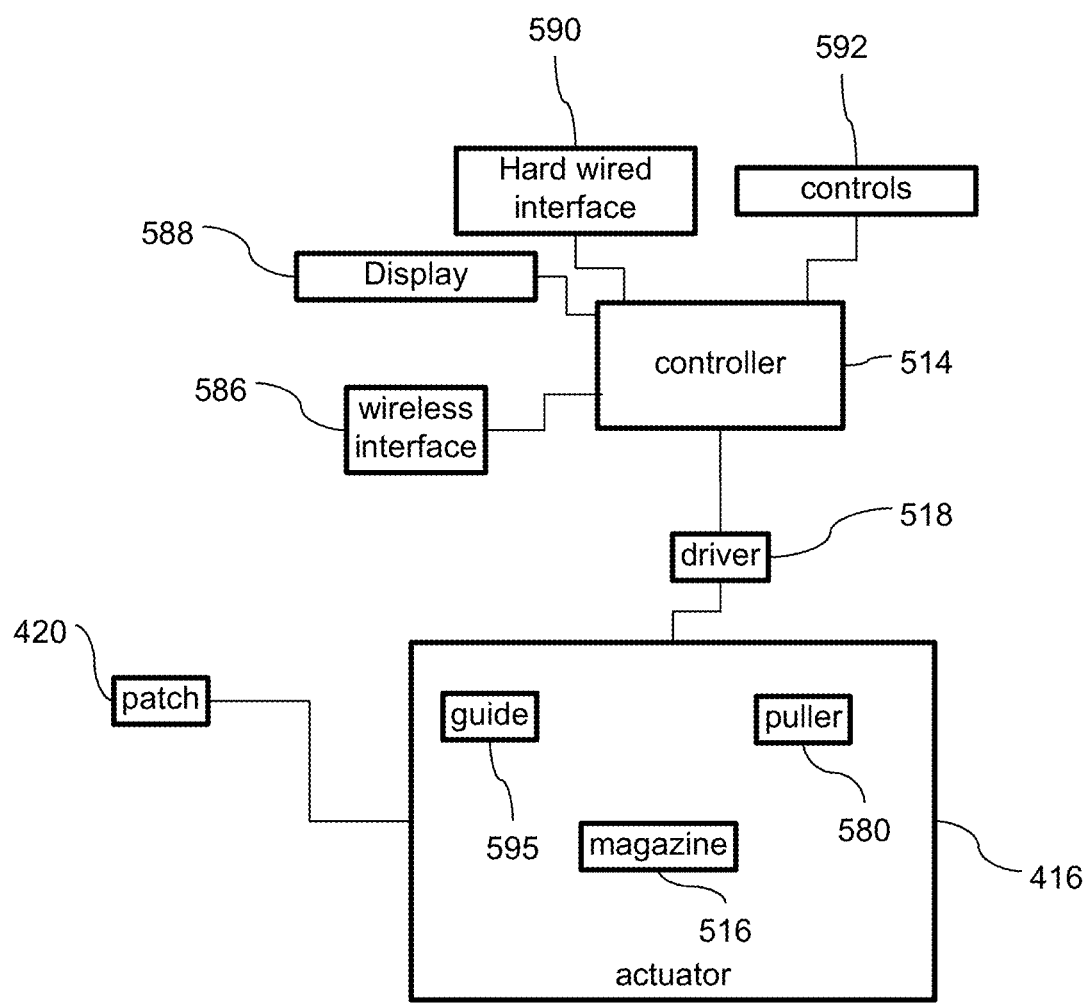
FIGS. 5A, 5B are block diagrams illustrating further optional features of a device for controlling engagement of a drug patch in accordance with some embodiments of the current invention.

FIG. 5A is a block diagram illustrating further optional features of a device for controlling engagement of a drug patch in accordance with an embodiment of the current invention. In some embodiments, a patch controlling device includes a controller 514. For example controller 514 may be programmable. Optionally controller 514 controls a drive 518 which powers an actuator 416 to switch patch 420 between operation states (for example fully engaged, fully disengaged and/or partially engaged). Optionally actuator 416 may include one or more mechanical sub elements. For example mechanical elements may manipulate patch 420. For example a guide 595 may direct a separation line between a patch and skin of a subject. Optionally a puller 580 may pull a portion of a patch 420. For example puller may pull a patch away from skin of a user and/or put tension on patch 420 keeping it connected to guide 595. Optionally, a patch control device may include a repository 516 for storing a patch.

In some embodiments, a guide may include a roller that rolls along and/or directs a separation line where a patch is separated and/or united with the skin of the subject. Alternatively or additionally a guide may include a sliding object and/or a wiper and/or flattening element and/or a straight edge that directs the separation line.

In some embodiments, a repository 516 may include a roller that stores a patch, for example by rolling it up. Alternatively or additionally a repository 516 may include a region inside a housing and/or a substrate that holds a patch stored away from the skin of the subject.

Figure 21A:
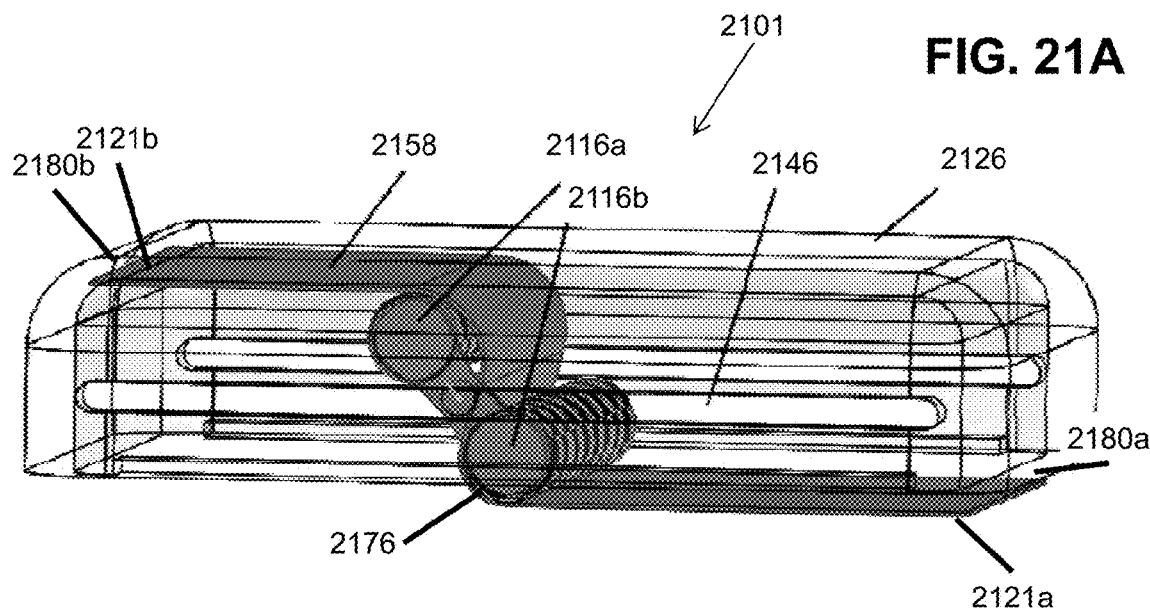
Figure 21B:
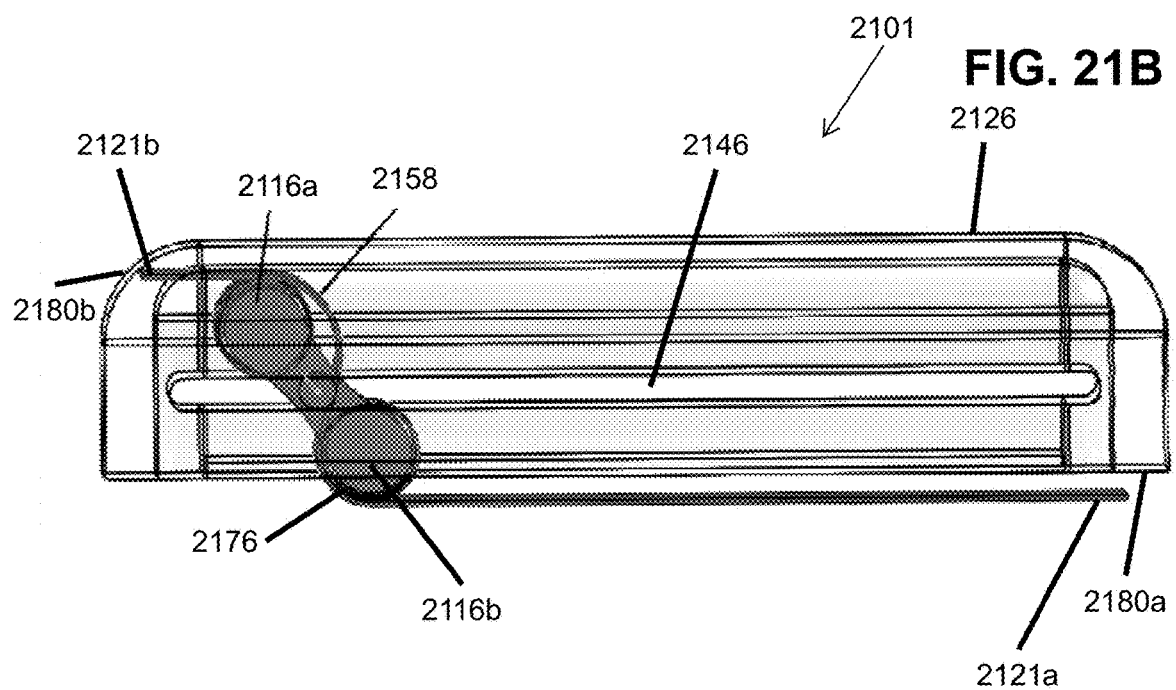

In some embodiments, a puller may include a roller that keeps tension on a patch, for example as illustrated by puller 2116a of FIGS. 21A-21C. Alternatively or additionally a puller may include an elastic substance and/or a spring and/or a connection to a housing that keeps tension on a patch. Optionally, a puller alone and/or in combination with a guide may pull and/or peel a patch. Optionally a patch may be pulled and/or peeled a peeling angle for example between 0 to 10 degrees from the horizontal and/or between 10 to 45 degrees and/or between 45 to 80 degrees and/or between 80 to 100 degrees and/of between 100 to 135 degrees between 135 to 170 degrees and/or between 170 degrees to 180 degrees where is 0 degrees is pulling the separation line directly towards a separated edge, 90 degrees is pulling the patch directly away from the skin and 180 degrees is pulling the patch directly toward a zone where the patch is adhered to the skin.

In some embodiment a single component may pull and/or guide a separation line and/or store a portion of the patch. For example when roller 816a of FIG. 8A optionally disengages patch 820, roller 816a optionally pulls up on the free end of the patch and/or roller 816a optionally stores patch 820 by wrapping it around roller 816a and/or guides separation line 876a.

In some embodiments, a user interface is provided, for example including a wireless interface 586. For example a subject may use a personal computing device (for example a smart phone) to communicate with controller 514 over a wireless interface. For example, a cell phone may output status information of the control device and/or a user may use the cell phone as an input device to control and/or program the patch control device. Optionally a patch control device may include a dedicated display 588. For example display 588 may include a status indicator, for example a LED that shines green when working properly and/or red on a malfunction. Alternatively or additionally display 588 may include a LCD display giving alpha-numeric messages. In some embodiments a patch control device may include a hard wired port 590, for example a charger port and/or a hard wired communication port and/or a combination port for example an USB port. Alternatively or additionally a patch control device may include local controls 592 for example a button and/or a switch. For example, local controls may include an on/off switch and/or a toggle switch to increase and/or decrease a dosage.

Figure 5B:
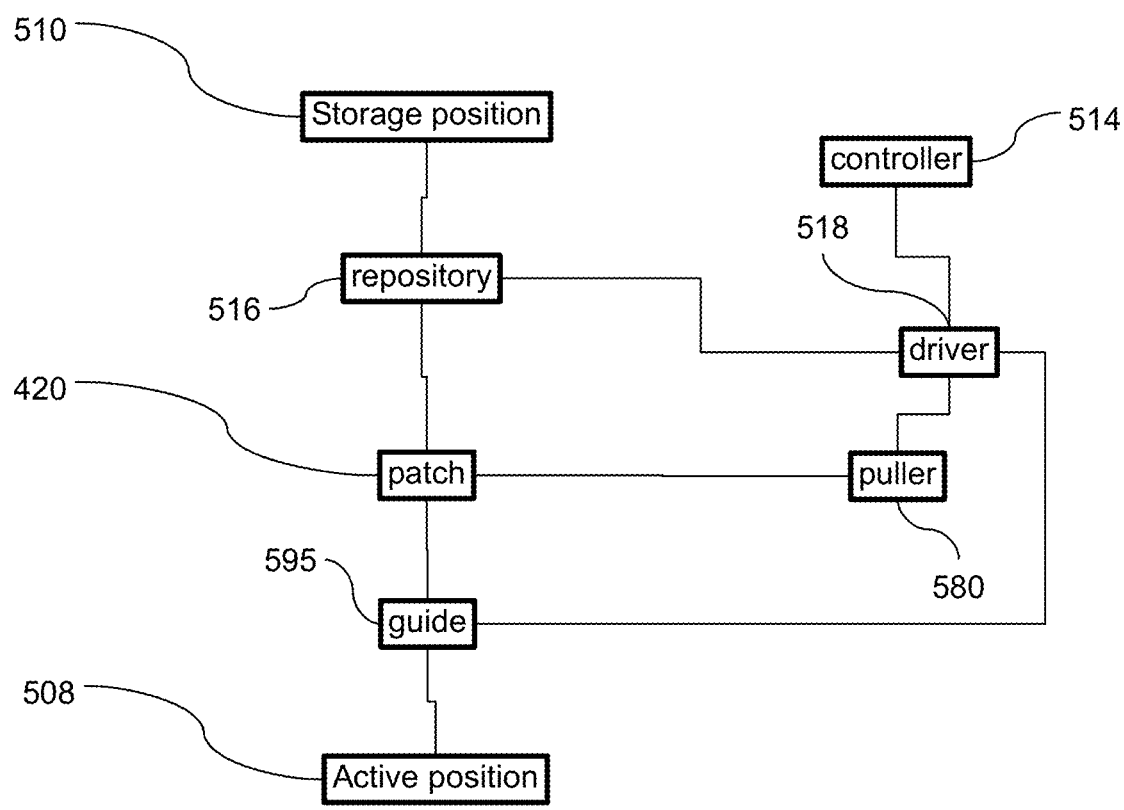

FIG. 5B is a block diagram illustrating further optional features of a device for controlling engagement of a drug patch in accordance with an embodiment of the current invention. In some embodiments, a patch controlling device initiates and/or increases a rate of deliver by engaging an active surface of a patch and/or a portion thereof. In some embodiments, a patch controlling device may interrupt and/or reduce a rate of deliver by disengaging an active surface of a patch and/or a portion thereof. An actuator is optionally driven by driver 518. Optionally driver 518 is controlled by a controller 514.

In some embodiment, an actuator includes a repository 516 and/or a guide 595 for example to engage a patch by moving an active surface from a storage position 510 to an active position 508 and/or a puller 580. In some embodiments, a puller 580 disengages patch 420 by moving the active surface from the active position 508 to the storage position. In some embodiments, an actuator may be configured to activate a patch only without deactivating the patch. Alternatively or alternatively an actuator may be configured to deactivate a pre-activated patch. Alternatively or additionally, in some embodiments an actuator may be configured to activate and deactivate patch 420.

In some embodiments, controller 514 may include a processor and/or a communication interface and/or a memory. Optionally controller 514 may receive input from a local and/or remote user and/or a sensor.

FIG. 6 is a block diagram illustrating further optional features of a device for controlling engagement of a drug patch in accordance with an embodiment of the current invention. In some embodiments an actuator may include a roller 616. For example in the stored position, patch 420 may be rolled up onto roller 616. Optionally a protector 622 to protect a patch in the storage position (e.g. rolled up 610 on a roller). For example, a protector may include a liner separating between layers of patch 420 rolled up on roller 616.

In some embodiments, an adapter, for example interface 624 may connect between patch 420 and the patch controlling device. For example, interface 624 may include a substrate connecting to patch 420. Alternatively or additionally a portion of interface 624 may be configured to connect to roller 616 and/or a frame 626 of the patch control device. For example, a mobile portion of the interface may be connected to the roller and/or a stationary portion of interface 624 may be connected to frame 626.

In some embodiments, driver 518 may reposition and/or rotate roller 616 to move patch 420 from the rolled up 610 stored state to and engaged 608 state contacting a skin 611 of a subject. Optionally, driver 518 may reposition and/or rotate roller 616 to disengage patch from skin 611 and/or roll the patch to the rolled up 610 storage position.

In some embodiments, a patch dosage regulator may be responsive to an event and/or a condition of the subject and/or a sensor output. For example, a sensor 698 may monitor a condition of a subject. Optionally, sensor output may be sent to controller 514. Alternatively or additionally, sensor output may be sent to an external decision maker (e.g. a processor and/or a person) who may send a message to controller 514. Based on the sensor output controller 514 may engage and/or disengage a drug patch and/or increase and/or decrease a dosage. For example sensor 698 may measure one or more of a blood flow, posture, heart rate, a blood oxygen content, breathing rate, temperature.

Loading a Patch to a Control Device

Figure 7:
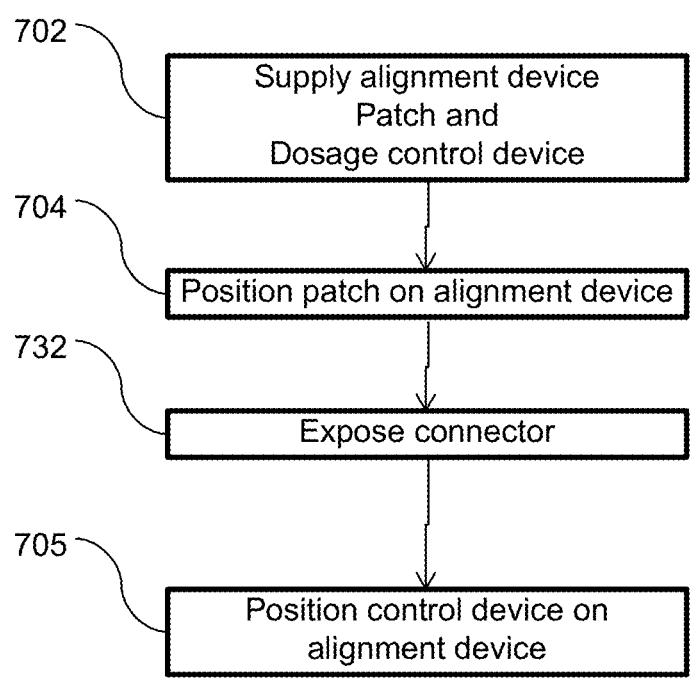
FIG. 7 is a flow chart illustration of a method of loading a patch to a dosage control device in accordance with an embodiment of the present invention

FIG. 7 is a flow chart illustration of a method of loading a patch to a dosage control device in accordance with an embodiment of the present invention. In some embodiments, an alignment device and a patch and a control device are supplied 702 such that positioning 704 the patch and positioning 705 the control device onto the alignment device loads the patch to the control device.

Figure 14:
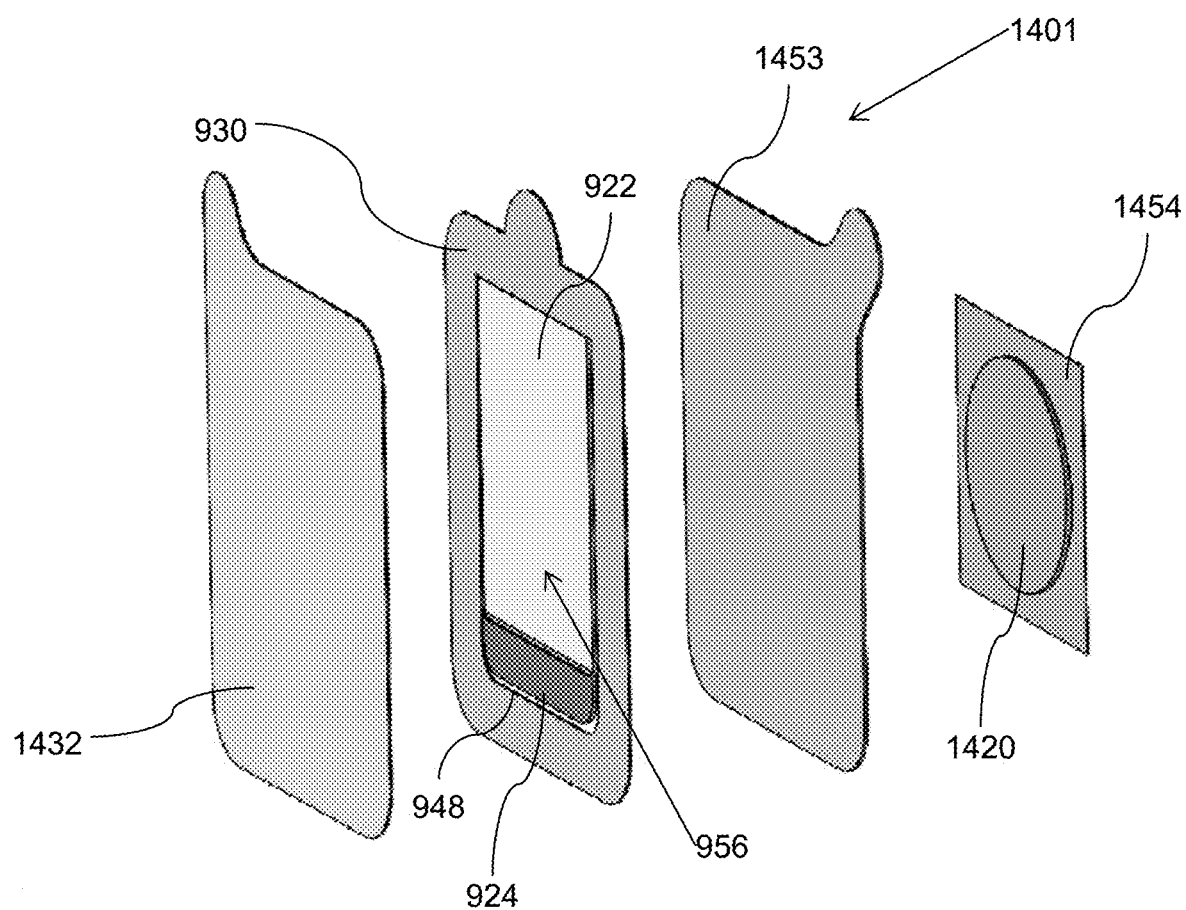
FIG. 14 is a schematic illustration of an adapter for connecting a patch to a patch control device in accordance with an embodiment of the current invention.

In some embodiments, a patch may be preloaded into an alignment device. Alternatively or additionally a user may place the patch onto the device. For example a user may place the ventral face of patch 920 onto base 939 of device 940. Optionally a user may remove a liner from the patch to expose 732 a connector (For examples removing dorsal liners 1232 from patch 920 and/or liner 1432 of from adapter 1401, for example as illustrated in FIG. 14, exposes 732 connector 924).

Patch Roller

Figure 8A:
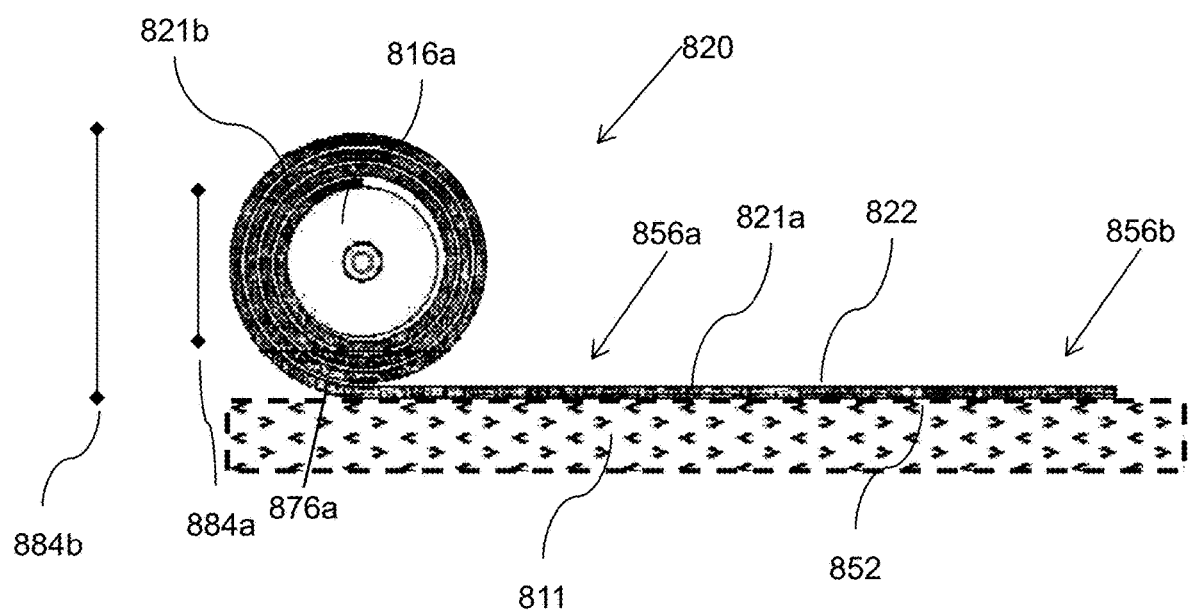
FIGS. 8A-8C are perspective side views of engaging and/or disengaging portions of a patch and/or storing disengaged portions of the patch in accordance with some embodiments of the present invention.

FIG. 8A is a perspective side view of a roller in which optionally guides a separation line. A roller optionally also pulls a patch and/or stores a patch in accordance with an embodiment of the present invention. In some embodiments, patch 820 is stored by rolled up onto a roller 816a. Optionally, roller 816a engages a portion 821a of patch 820 by unrolling portion 821a of the patch along a separation line 876a onto a skin 811 of a subject. For example, in the view of FIG. 8A, roller 816a rolls leftward to engage and/or unrolls patch 820 onto skin 811. Optionally, roller 816a disengages the patch for example by pulling and/or peeling the leading edge of the patch from the skin. For example, in the view of FIG. 8A, roller 816a roller rightward to roll up and/or disengage patch 820 from skin 811.

In some embodiments, the diameter of a rolled up patch 820 may increase as more patch 820 is rolled up. For example, before the patch starts being rolled up, the total diameter may be roller diameter 884a. As the patch is rolled up, the roll diameter 884b may increase. For example, the roller diameter 884a may start at 8 mm and roll may grow for example to a roll diameter 884b of about 20 mm as the patch is loaded onto roller 816a.

In some embodiments, patch 820 includes an active zone 856a and/or an inactive zone 856b. For example, inactive zone 856b may have an active surface on a ventral face thereof and/or may be on the trailing edge of patch 820. Optionally, when patch 820 is fully rolled up onto roller 816a, only a trailing section including inactive zone 856b is in contact with skin 811 and/or active zone 856a is not in contact with the skin. Optionally, when active zone 856a is not in contact with the skin, no treatment occurs. Alternatively or additionally, different zones of a patch may include different drugs for different treatments. For example, zone 856a may include a first drug that is applied to skin 811 from the beginning of a treatment and zone 856b may have a different drug which is applied to the skin later in the treatment.

In some embodiments, patch 820 includes a skin contact surface 852 on a ventral side thereof. Optionally, a dorsal side of the patch is covered by a protector 822. For example, protector 822 may include a liner. Optionally protector 822 includes a chemically inert and/or clean and/or sterile and/or non-stick surface. Optionally, during storage, for example on a rolled up portion 821b of patch 820, protector 822 covers skin contact surface 852 of active zone 856a of patch 820. For example, roller 816a may peel and/or place patch 820 from and/or to the skin on a separation line 876a. Optionally, separation line 876a is the line of contact. For example at separation line 876a, patch 820 is sandwiched between roller 816a and skin 811.

Figure 8B:
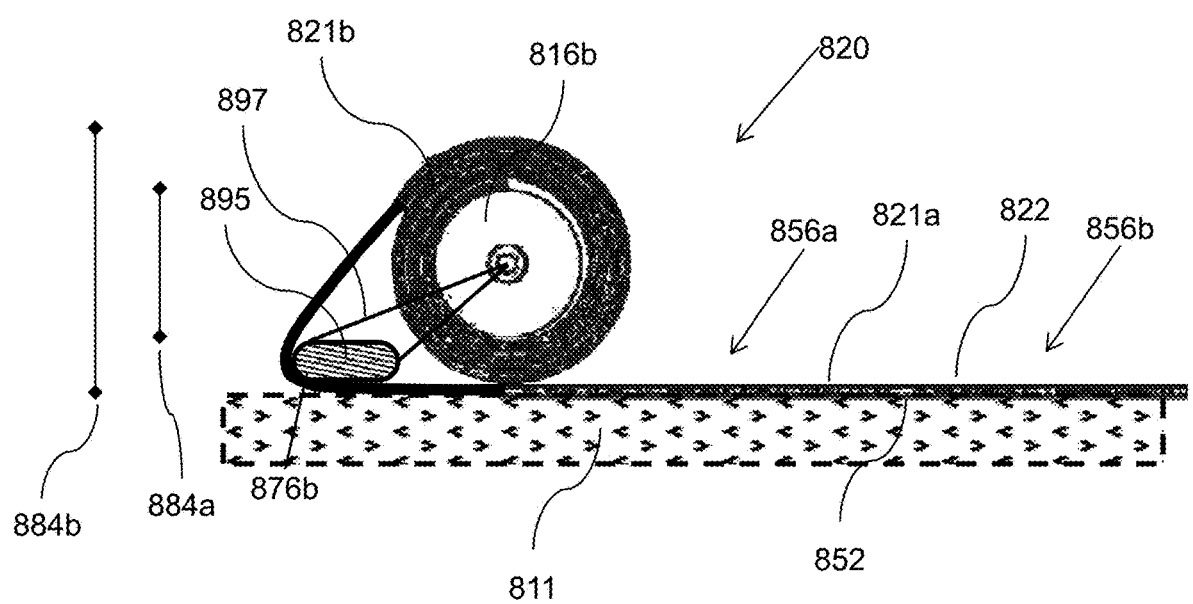

FIG. 8B is a perspective side view of a patch control system having a roller 816b which optionally keeps tension on the patch and/or stores the patch and a separate guide 895 which optionally guides a separation line 876b in accordance with an embodiment of the current invention. In some embodiments, guide 895 is supported on supports 897.

Figure 8C:
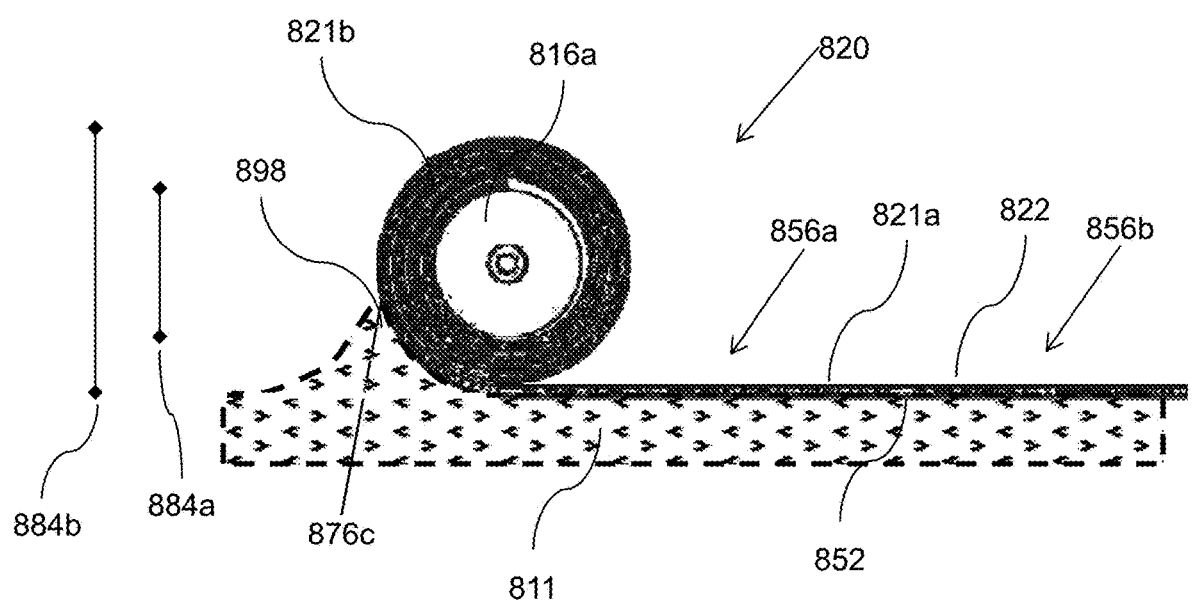

FIG. 8C is a perspective side view of a roller 816a which optionally guides a separation line 876c, pulls a patch 820 and/or stores patch 820 in accordance with an embodiment of the present invention. In some embodiments, patch 820 will deform skin 811, for example by pulling skin 811 into a mound 898 while disengaging patch 820. In some embodiments, the deformation of skin 811 may affect the peeling angle of patch 820. For example by having a smaller guide the effect of mounding of the skin on the angle of peeling may be greater. For example the angle of peeling may be decreased by more mounding of the skin (for example due to a sticker adhesive) and/or the angle of peeling may be decreased by using a larger guide (for example a roller with a larger diameter). The stickiness of the patch, size of the guide and/or direction of pulling may be adjusted for example to reduce discomfort when peeling a patch.

Exemplary Stationary Reversible Patch Roller System

Figure 9A:
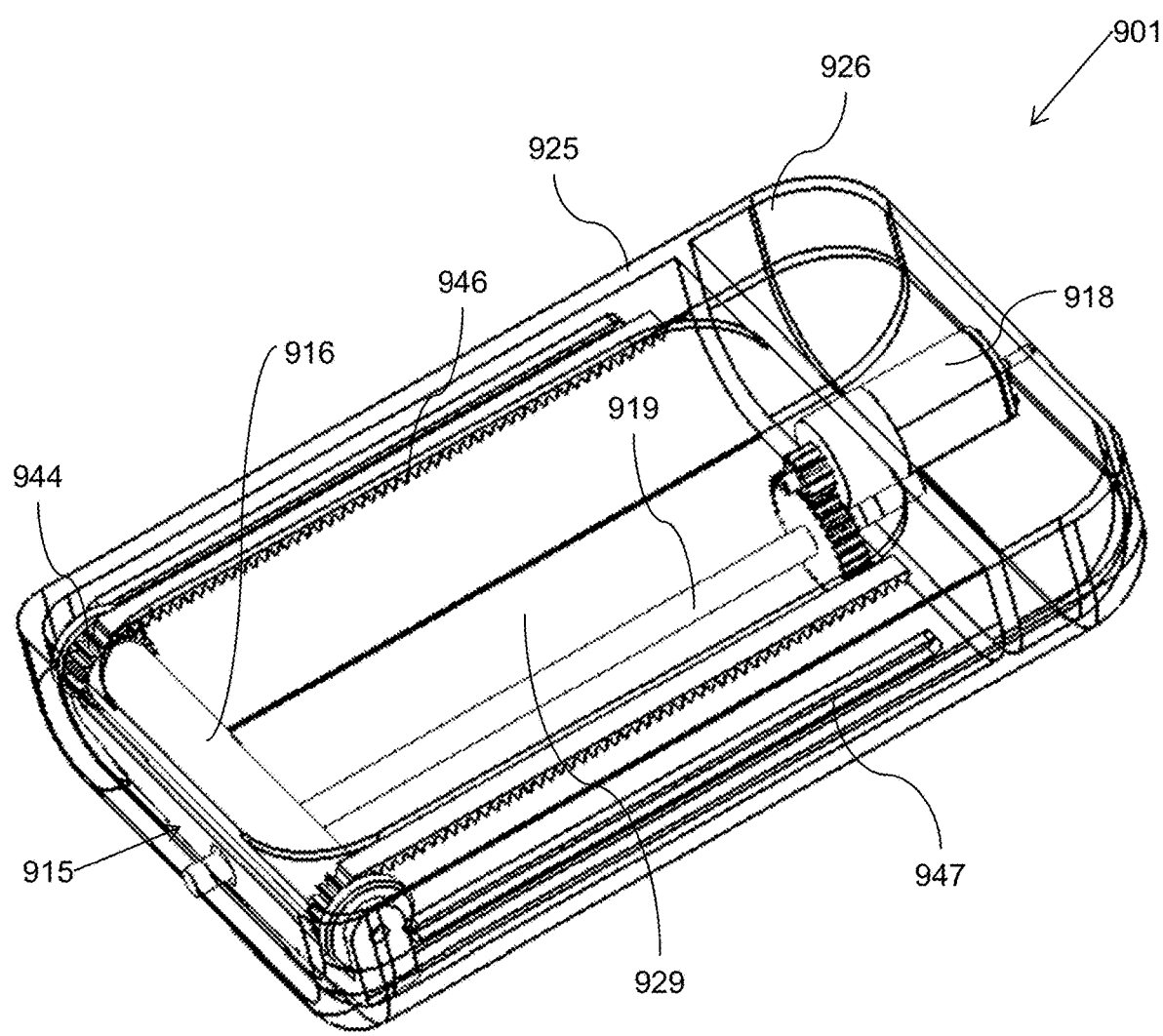
FIG. 9A is a perspective view of a ventral side of a patch control device with a roller in accordance with an embodiment of the present invention.

FIG. 9A is a perspective view of a ventral side of an exemplary patch control device 901 in accordance with an embodiment of the present invention. Optionally device 901 reversibly engages and/or disengages portions of a patch. Optionally device 901 stores disengaged portions of the patch. In some embodiments, device 901 includes a roller 916. Optionally roller 916 rolls backwards and/or forward inside a frame 926. For example, when roller 916 rolls in one direction it rolls up and/or disengages a portion of a patch. For example, when roller 916 rolls in an opposite direction it unrolls and/or engages a portion of the patch. Optionally, a stored portion may be protected by a liner and/or stored on a roller 916.

In some embodiments, frame 926 includes a shell surrounding roller 916. Optionally frame 926 includes a contact surface 925 on a base of the ventral side of frame 926. Optionally contact surface 925 surrounds an opening 929. For example, contact surface 925 fully surrounds opening 929. Alternatively or additionally a contact surface may only partially surround opening 929. For example, when the device 901 is placed onto a subject, contact surface 925 lies against the skin of the subject. Optionally when a patch is in an engaged state, an active surface of the patch is exposed to and/or contacts the skin of a subject through opening 929. Optionally in a disengaged state, the active surface may be rolled up on roller 916 and does not contact the skin of the user.

In some embodiments, frame 926 includes one or more tracks. For example, frame 926 includes a sliding guide track 947 and/or a friction track 946. Optionally a driver 918 (for example including a DC motor) drives a transmission 919 to pull or push a roller assembly 915 longitudinally along guide track 947. For example transmission 919 may include a threaded shaft which is engaged to a thread in assembly 915. For example rotating transmission 919 in one direction pulls assembly 915 longitudinally along track 947 towards driver 918. For example rotating transmission 919 in an opposite direction pushes assembly 915 longitudinally along track 947 away from driver 918.

In some embodiments, as assembly 915 moves longitudinally along guide track 947, roller 916 rotates to roll up and/or unroll a patch. Optionally as assembly 915 moves in a first direction roller 916 rolls up and/or disengages a patch. Optionally as assembly 915 moves in an opposite direction roller 916 unrolls and/or engages the patch. For example, as assembly 915 moves longitudinally, a friction contact surface 944 of roller 916 rolls along friction track 946, causing roller 916 to rotate. For example, friction track 946 may include teeth that engage to teeth of friction contact surface 944 which optionally includes a gear.

In some embodiments a synchronizer may synchronize the rate of engaging of patch 920 with the rate of movement roller 916. For example the teeth of track 946 may be differentially spaced. For example the spacing of the teeth may be configured to synchronize rolling of roller 916 with its linear movement. Alternatively or additionally a controller may separately control the linear and rotational movements (for example with separate drivers).

Figure 9B:
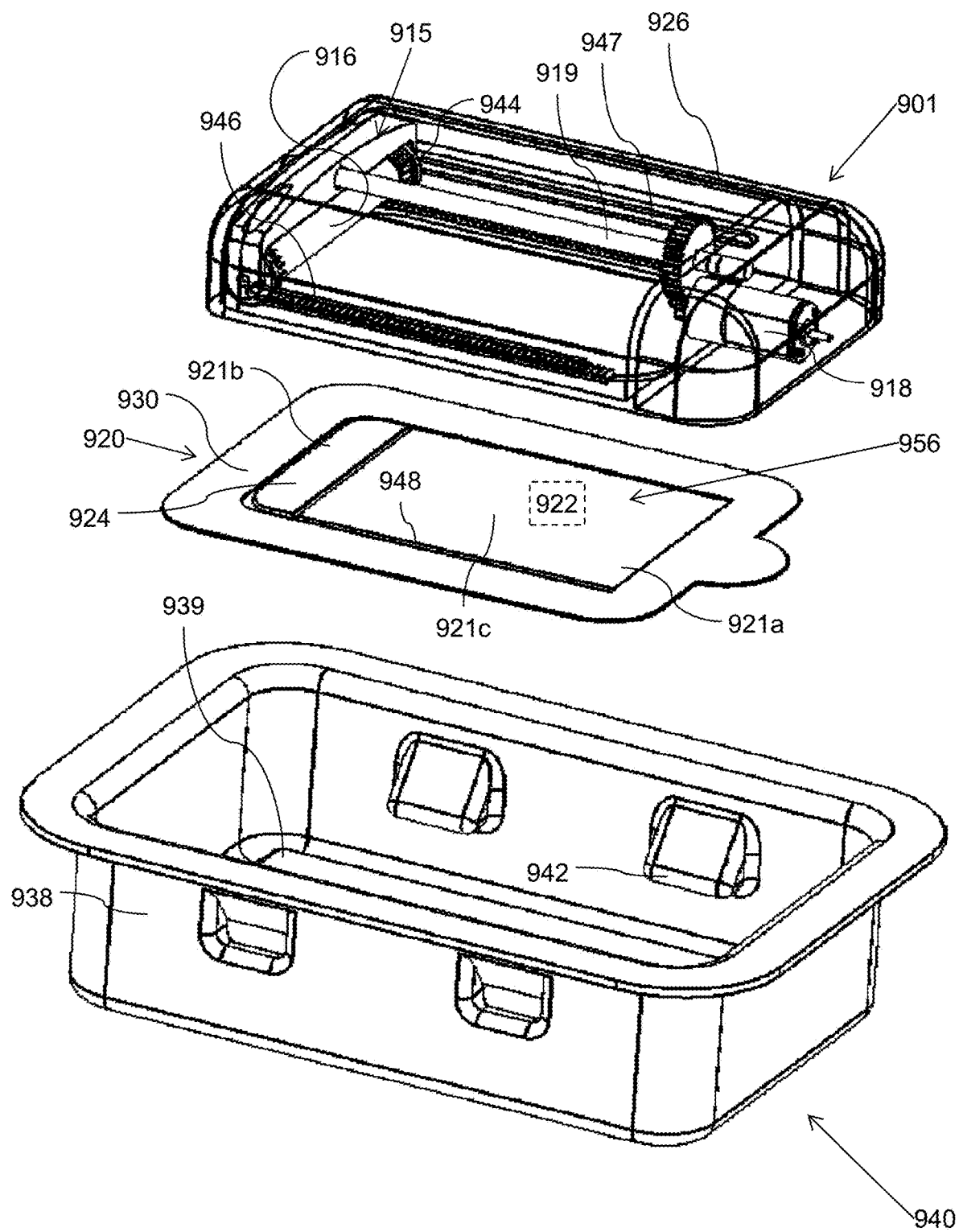
FIG. 9B is a perspective view of a dorsal side of a patch control system with a roller in accordance with an embodiment of the present invention.

FIG. 9B is a perspective view of a dorsal side of a patch control system in accordance with an embodiment of the present invention. Optionally, a patch control system reversibly engages and/or disengages portions of a patch. Optionally, a patch control system may stores disengaged portions of the patch and/or protects stored portions, for example by a liner. For example the portions are stored on a roller. In some embodiments, a patch control system may include a patch control device 901 and/or an optionally custom patch 920 and/or an alignment device 940.

In some embodiments, patch 920 includes a stationary portion 930. Optionally, stationary portion 930 may include adhesive of both sides. For example adhesive on the dorsal side may adhere stationary portion 930 to contact surface 925 of frame 926. For example, adhesive on the ventral side of stationary portion 930 may adhere to stationary portion 930 and/or contact surface 925 of frame 926 to the skin of a subject. For example, when device 901 is positioned on a subject, stationary portion 930 may be immobile and/or sandwiched between contact area 925 of frame 926 and the skin of the subject. In some embodiments, stationary portion 930 surrounds a disengageable portion 956 of the patch (the disengageable portion 956 optionally includes a leading portion 921b, a trailing portion 921a and/or a mid portion 921c.

In some embodiments, connections between patch 920 and device 901 are made by a single simple movement. For example, device 901 has all of its connections to patch 920 exposed on one side (e.g. the ventral side of device 901 connects to the dorsal side of patch 920). For example, a contact zone of roller 916 which contacts adhesive 924 of the leading mobile end of mobile portion 956 and/or a contact surface 925 of device 901 which connects stationary portion 930 of patch are all exposed on a ventral face of device 901. For example by pushing device 901 downward onto the dorsal surface of patch 901 the patch is loaded to device 901. Optionally all of the connection surface lie on a place such that device 901 connects to patch 920 while patch 920 is lying flat on a surface. Alternatively or additionally an alignment device 940 has a base with contours that position patch 920 properly to connect to each part of device 901. For example, the contact zone of roller 916 may be recessed with respect to contact surface 925. Optionally the base of alignment device 940 holds the free leading portion 921b extended upward to contact the contact roller 916 when device 901 is lowered into place onto alignment device 940. Optionally, after connection, a mobile engageable portion 956 may be wound to roller 916 (e.g. into a disengaged state) before attaching device 901 to a subject. Alternatively or additionally, device 901 may be attached to a subject in an engaged state.

In some embodiments, stationary portion 930 may partially surround engageable portion 956. For example, stationary portion 930 may just extend from a trailing portion 921a of engageable portion 956 of patch 920. Alternatively or additionally a patch may be entirely wound onto a roller without a frame contact area.

In some embodiments, a leading portion 921b and/or a mid portion 921c of engageable portion 956 is optionally separated from frame contact area by a discontinuity, for example a cut out 948. For example, cut out 948 permits leading portion 921b and or central portion 921c to roll up onto roller 916 while stationary portion 930 remains stationary with respect to the skin of the subject, for example on or close to the skin of the subject. Alternatively or additionally, cut out 948 permits leading portion 921b and or central portion 921c to roll up onto roller 916 while stationary portion 930 remains stationary with respect to frame 926, for example sandwiched between contact surface 925 of frame 926 and/or the skin of the subject.

In some embodiments, patch 920 may be sold as a whole conventional patch without a discontinuity. For example the discontinuity is optionally cut into the patch after production and/or sale. Optionally, a device and/or die may be supplied to cut a discontinuity. For example, the cut out device may be a separate device, and/or may be including in packaging of a patch and/or of a dosage control device. For example alignment device 940 may include a die and/or blade to cut the discontinuity. For example a convention patch may be modified by cutting a discontinuity. Optionally the discontinuity will be in a non-active area. For example cutting a discontinuity into a patch may not compromise an active area and/or a drug reservoir and/or a release membrane.

In some embodiments, leading portion 921b of disengageable portion 956 of patch 920 includes adhesive 924 on its dorsal side. Adhesive 924 optionally connects leading portion 921b to roller 916. Alternatively or additionally, roller 916 may be coated with adhesive. Alternatively or additionally, roller 916 and/or leading portion 921b may include a magnet and/or a clip and/or a hook and/or a slit to for example for connecting the free portion of the patch to the roller.

In some embodiments, a protector may protect an active zone and/or a skin contact surface of a patch during storage. For example, a flexible backing including for example a liner 922 covers mid section 921c of stationary portion 930. When patch 920 is stored (for example by rolling up onto roller 916 such that engageable portion 956 is wound around roller 916) the skin contact surface of engageable portion 956 is optionally covered by liner 922. Optionally liner 922 is made of a chemically inert and/or non-stick and/or non-reactive substance that will protect the drug in engageable portion 956. Optionally liner 922 is made of a non-stick substance that will protect the adhesive on the skin contact area of engageable portion 956 of patch 920. For example liner 922 may be made of a non-reactive coating over a substrate. For example a non-reactive coating may include Polyethylene and/or the substrate may include a metal foil (e.g. aluminum) with a thickness between 0.05 and 0.2 mm. Alternatively or additionally a substrate may include paper and/or plastic.

In some embodiments, a patch control system may include an alignment device 940. For example alignment device 940 may include a cavity of a blister package for patch 920 and/or device 901. For example, device 901 and/or patch 920 may be packed inside of device 940 and sealed with a backing for shipping and distribution. Device 940 optionally includes interference elements 942. For example interference elements may be used to snap device 901 into device 940. For example elements 942 may hold the ventral face of device 901 firmly against base 939 of device 940. Optionally device 940 may be used to mount patch 920 onto device 901. Alternatively or additionally, alignment may be facilitated with printed signs, pins, indentations and/or protrusions for the patch and/or device etc. Alternatively or additionally, device 901 may be preloaded with patch 920. Alternatively or additionally, patch 920 may be mounted to device 901 without an alignment device. Alternatively or additionally, device 901 may be used with a standard patch and an interface (for example patch 1420 and/or adapter 1401 as illustrated in FIG. 14). Alternatively or additionally other options for patch geometry may be used with device 901.

In some embodiments, positioning the patch and the control device onto the alignment device will connect the patch to the control device. For example, once patch 920 is lying on base 939 with connector 924 exposed, device 901 is placed onto alignment device 940 with contact surface 925 facing towards the exposed connector 924 on patch 920. Optionally device 901 is pushed past interference elements 942 which snap down on device 901 securely pushing contact surface 925 against stationary portion 930 and/or pushing roller 916 against connector 924. Optionally alignment device 940 is shaped such that patch 920 and/or device 901 are pushed into proper alignment when they are positioned on device 940. For example, a cavity of device 940 may have beveled walls 938 leading to a tight fitting compartment such that putting a patch and/or control device into the cavity pushes them into mutual alignment.

Figure 10:
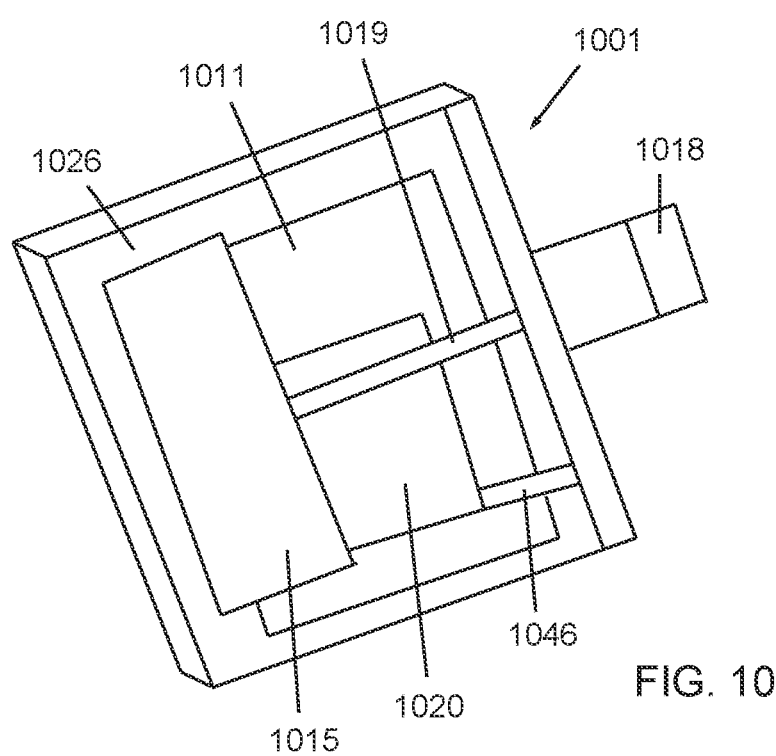
FIG. 10 is a photograph of an exemplary patch control device 1001 in use in accordance with an embodiment of the current invention.

FIG. 10 is a photograph of an exemplary patch control device 1001 in use in accordance with an embodiment of the current invention. A patch 1020 is optionally loaded into device 1001. Patch 1020 and device 1001 are then optionally placed against the skin 1011 of a subject. For example, during placement, patch 1020 may be in an engaged state. For example, medicine delivery may begin immediately when patch 1020 and control device 1001 are placed on skin 1011. Optionally a roller assembly 1015 is pulled by a transmission 1019 toward a driver 1018 to reversibly disengage patch 1020 from skin 1011. Optionally, as roller assembly moves towards driver 1018, a roller rolls along a track 1046 rolling up patch 1020. In some embodiments, roller assembly 1015 is pushed by transmission 1019 away from a driver 1018 to reversibly engage patch 1020 to skin 1011. Optionally, as roller assembly 1015 moves away from driver 1018, the roller 1026 rolls along a track 1046 unrolling patch 1020.

In some embodiments, patch control device 1001 may include a controller for example to control driver 918 and/or engagement and/or disengagement of the patch. Alternatively or additionally device 1001 may include a sensor. For example, patch control device 901 may respond to signals from the sensor to engage and/or disengage a patch fully and/or partially. Optionally the sensor output may be sent to a controller of the device.

Exemplary Patch

Figure 11A:
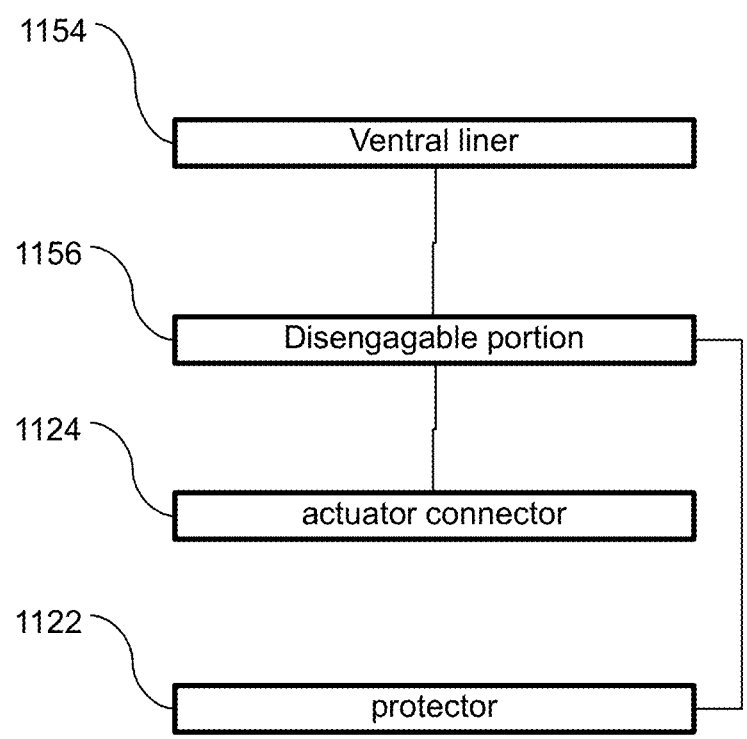
FIG. 11A is a block diagram illustration of a patch in accordance with some embodiments of the current invention.

FIG. 11A is a block diagram illustration of a simple patch in accordance with some embodiments of the current invention. Optionally, a patch may include a disengageable portion 1156. Optionally, the entire patch may be disengageable from the subject. In some embodiments, the patch includes an active surface. For example the active surface may be on a ventral face of the patch. Optionally the disengageable portion includes a connector 1124 for connecting to an actuator of a control device. The patch optionally includes a protector 1122. For example protector 1122 may protect the active surface during storage by a patch control device. Optionally the patch includes a ventral liner 1154. For example, ventral liner 1154 may protect an active region of the patch before use. For example, the ventral liner may be removed by a user prior to use of the patch. Optionally a patch may include a dorsal liner. For example connector 1124 may include an adhesive surface which is optionally protected by a dorsal liner.

In some embodiments an active surface of a patch may include a drug (for example a medicine patch). Alternatively or additionally the active surface may include an adhesive (for example a medicine patch and/or an interface for a medicine patch).

In some embodiments, connector 1124 may be on a leading edge of the patch and/or on a dorsal face of the patch for example on a dorsal face of a leading portion of the patch.

Figure 11B:
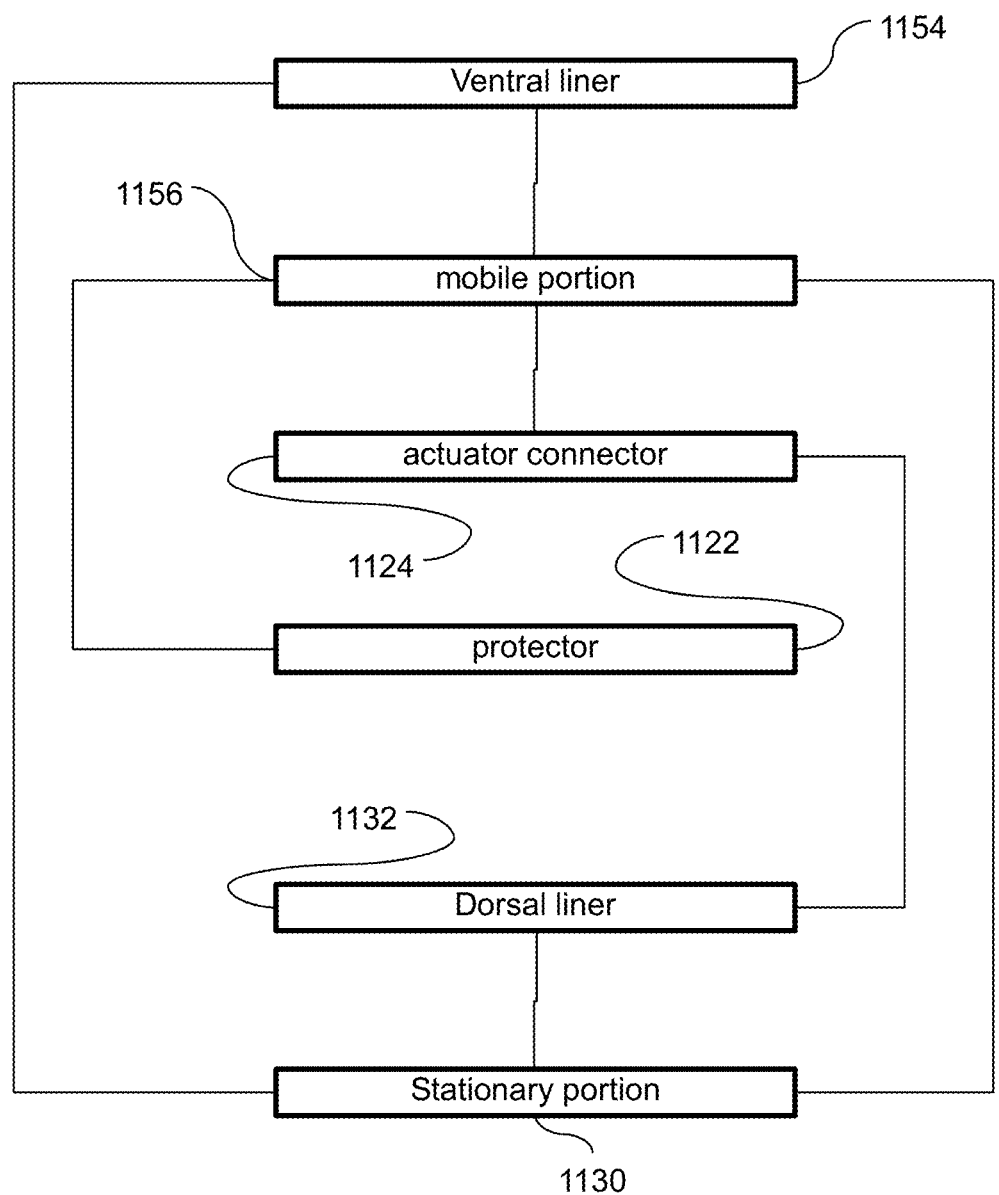
FIG. 11B is a block diagram illustration of a two part patch in accordance with some embodiments of the current invention.

FIG. 11B is a block diagram illustration of a two part patch in accordance with some embodiments of the current invention. In some embodiments, a patch may include a stationary portion 1130 and/or a disengageable portion 1156. For example the disengageable portion 1156 is configured to be connected by a connector 1124 to an actuator of a patch control device. Optionally stationary portion 1130 is configured to be connected to a stationary portion (for example a frame) of the patch control device. Optionally the stationary portion may include an adhesive on two sides and/or be connected to a dorsal liner 1132 and/or a ventral liner 1154. Dorsal liner 1154 optionally protects actuator connector 1124 of the disengageable portion 1156 of the patch.

Figure 12:
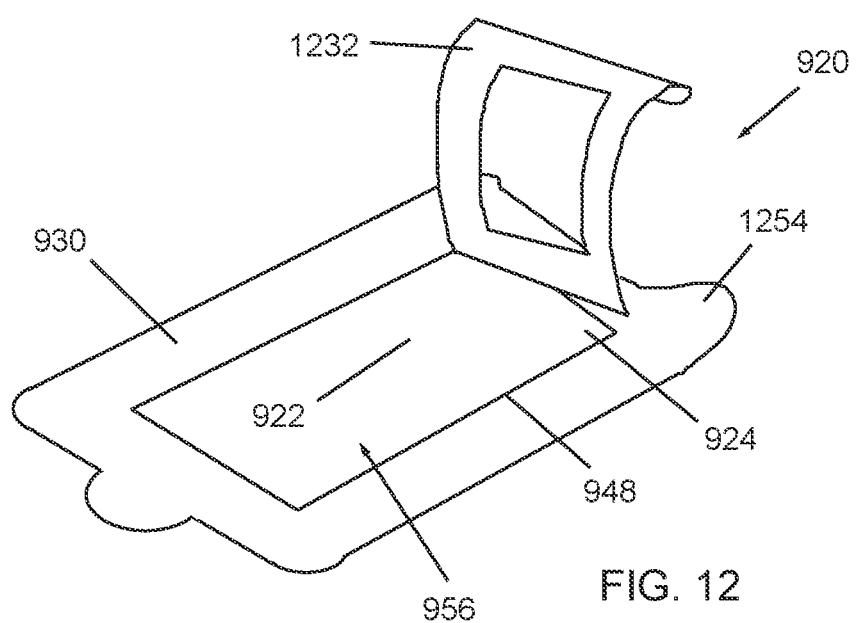
FIG. 12 is a perspective illustration of a dorsal side of a patch in accordance with an embodiment of the present invention.

FIG. 12 is a perspective illustration of a dorsal side of patch 920 in accordance with an embodiment of the present invention. A dorsal liner 1232 is illustrated partially removed from patch 920. Patch 920 is supplied to a user with, dorsal liner covering an adhesive dorsal surface of stationary portion 930 and/or an adhesive connector 924 for connecting a leading portion of disengageable portion 956 of patch 920 to an actuator of a patch control device. Optionally liner 1232 does not cover protector 922. Alternatively or additional, a dorsal liner may cover a protector for example as illustrated in FIG. 14 where a dorsal liner 1432 covers an entire dorsal face including a protector 922 of a interface patch 1401. In some embodiments, a ventral liner 1453 covers a ventral face of a patch. For example ventral liner 1453 may be peeled off before the patch is placed on the skin of a subject.

Figure 13:
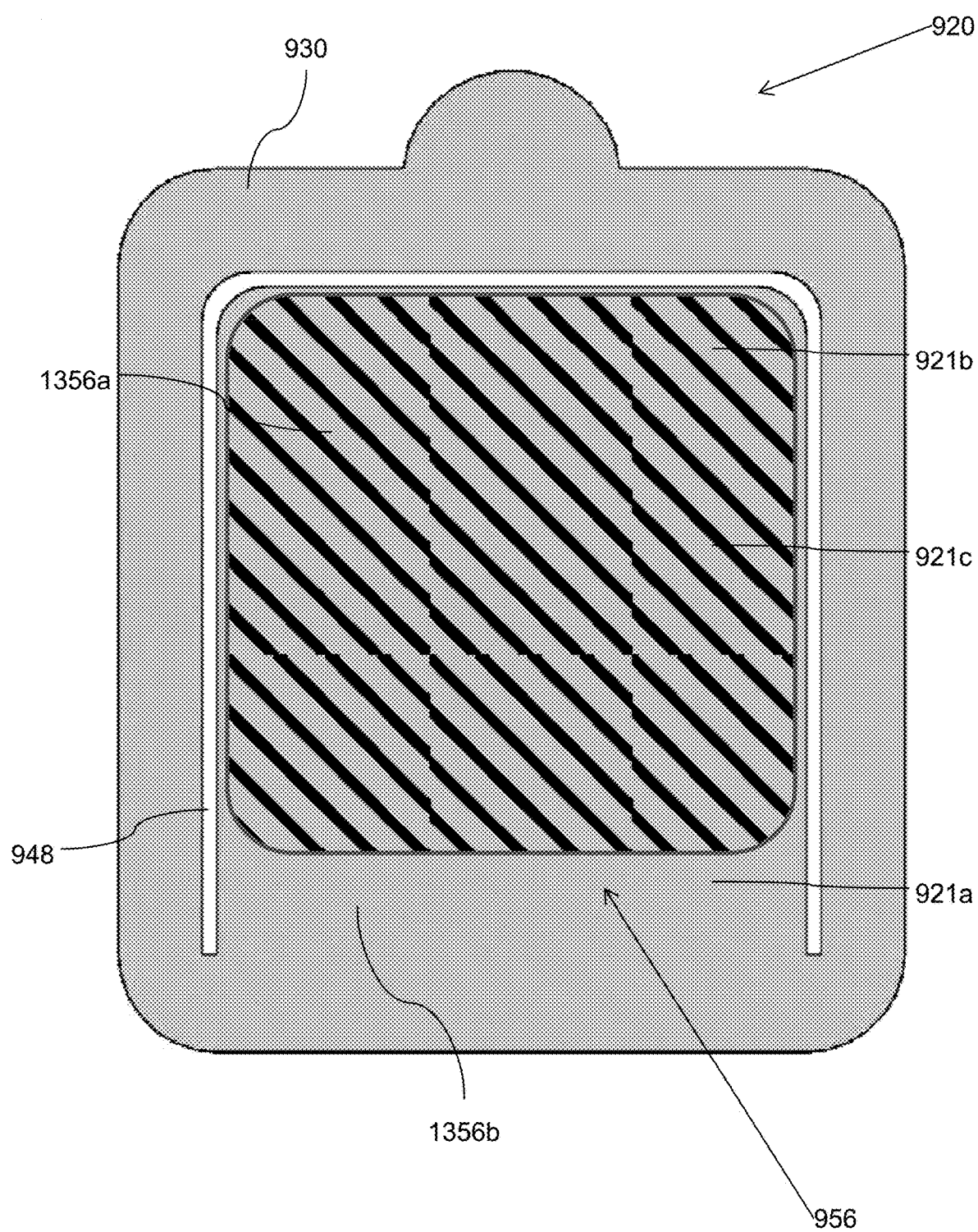
FIG. 13 is a perspective illustration of a ventral side of a patch in accordance with an embodiment of the present invention.

FIG. 13 is a ventral view of a patch in accordance with an embodiment of the current invention. In some embodiments a ventral face of patch 920 includes an active surface 1356a on a disengageable portion 956. For example active surface 1356a may include a drug that is absorbed by the skin of a subject when zone 1356a contacts the skin. Optionally a patch control device (for example device 901) controls the magnitude of the surface area of zone 1356a exposed to the skin and/or the rate of absorption of the drug to the subject. For example, disengaging part of zone 1356a reduces the dosage and/or rate of application of the drug. For example, engaging part of zone 1356a increases the dosage and/or rate of application of the drug.

In some embodiment trailing portion 921a of portion 956 may be included in an inactive surface 1356b. For example, misalignment of a device and/or a patch and/or irregularities of the surface of the skin may cause uncertainty in the state of engagement and/or disengagement of the trailing portion 921a and/or the outermost layer of the rolled up patch. Including portion 921a in inactive portion 1356b may decrease the uncertainty of dosage and/or avoid a danger that medicine will continue to be absorbed when patch 920 is supposed to be fully disengaged.

Exemplary Interface for Patch

FIG. 14 is a schematic illustration of an interface for connecting a patch to a patch control device in accordance with an embodiment of the current invention. In some embodiments, an interface may be used to facilitate loading a patch to a patch control device. Optionally an interface, for example, adapter 1401 may be used to facilitate loading a conventional medicine patch (for example patch 1420) to a control device, for example device 901. For example, a dorsal side of adapter 1401 may be configured for loading to device 901 and/or a ventral side of the patch may be configured for attaching to a convention patch.

In some embodiment, a ventral side of adapter 1401 may include a connector 924 and/or a protector 922. Optionally the ventral face of adapter 1401 is covered by a liner 1453 prior to use. Optionally adapter 1401 includes a stationary portion 930 which surrounds and/or partially surround and/or is partially attached to a disengageable portion 956. For example a cut out 948 may separate between some parts of the stationary portion 930 and disengageable portion 956.

In some embodiments, the ventral face of disengageable portion 956 of adapter 1401 includes a substrate and/or an adhesive. Optionally the dorsal face of patch 1420 is adhered to the ventral face of disengageable portion 956 of adapter 1401. The patch 1420 becomes the active region of disengageable portion 956. For example by engaging and/or disengaging the ventral side of portion 956 to the skin of a subject, patch 1420 is engaged and/or disengaged. The combined patch 1420 and adapter 1401 are optionally loaded to device 901 according to the method described in FIG. 7. In some embodiments, a skin contact area and/or an active face and/or ventral face and/or an active surface of patch 1420 will be protected by a liner 1454 prior to use.

In some embodiments, the adhesive area on the ventral said of the adapter 1401 will be larger than the dorsal side of patch 1420. Optionally the adhesive on the ventral side of patch 1401 may be formulated to stick fast to the dorsal face of patch 1420 and/or to be biocompatible and/or to be easily removed from skin. Alternatively or additionally, patch 1420 may be attached to adapter 1401 (for example to the ventral face of portion 956) by ultrasonic welding and/or heat and/or by means of a vacuum. For example, the ventral face of portion 956 may be a substrate that can include attached to patch 1420.

In some embodiments, an adapter and/or an alignment device will be shaped and sized for a particular patch. For example, an area of adhesive on a ventral side of the adapter may fit the patch. For example the adhesive area may be within 1 mm of the dimensions of the dorsal face of the patch and/or within between 1 and 5 mm and/or between 5 and 20 mm. Optionally an alignment device may facilitate fitting the convention patch to the adaptor and/or the patch control device and/or fitting the adaptor to the patch control device. Optionally, attaching patch 1420 to adapter 1401 and/or device 901 does not change an active surface of and/or drug administration property of patch 1420.

Alternative Stationary Reversible Patch Roller System

Figure 15A:
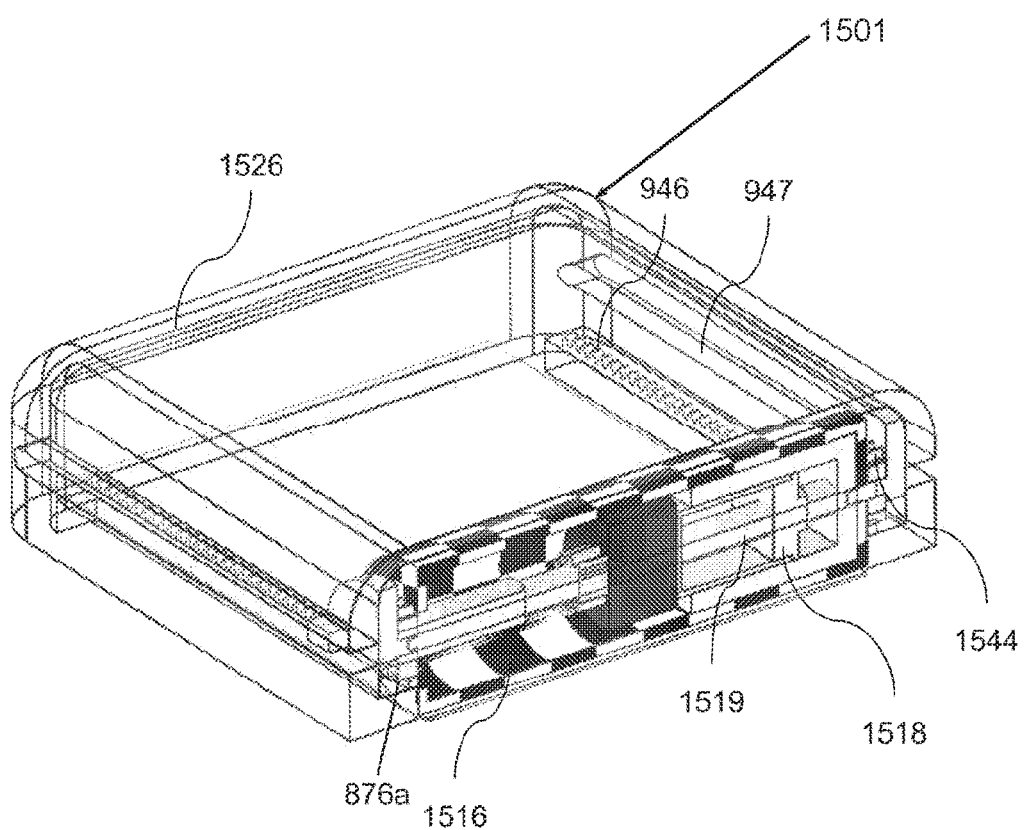
FIGS. 15A-15C are perspective views a roller patch control device in accordance with an embodiment of the present invention.
Figure 15B:
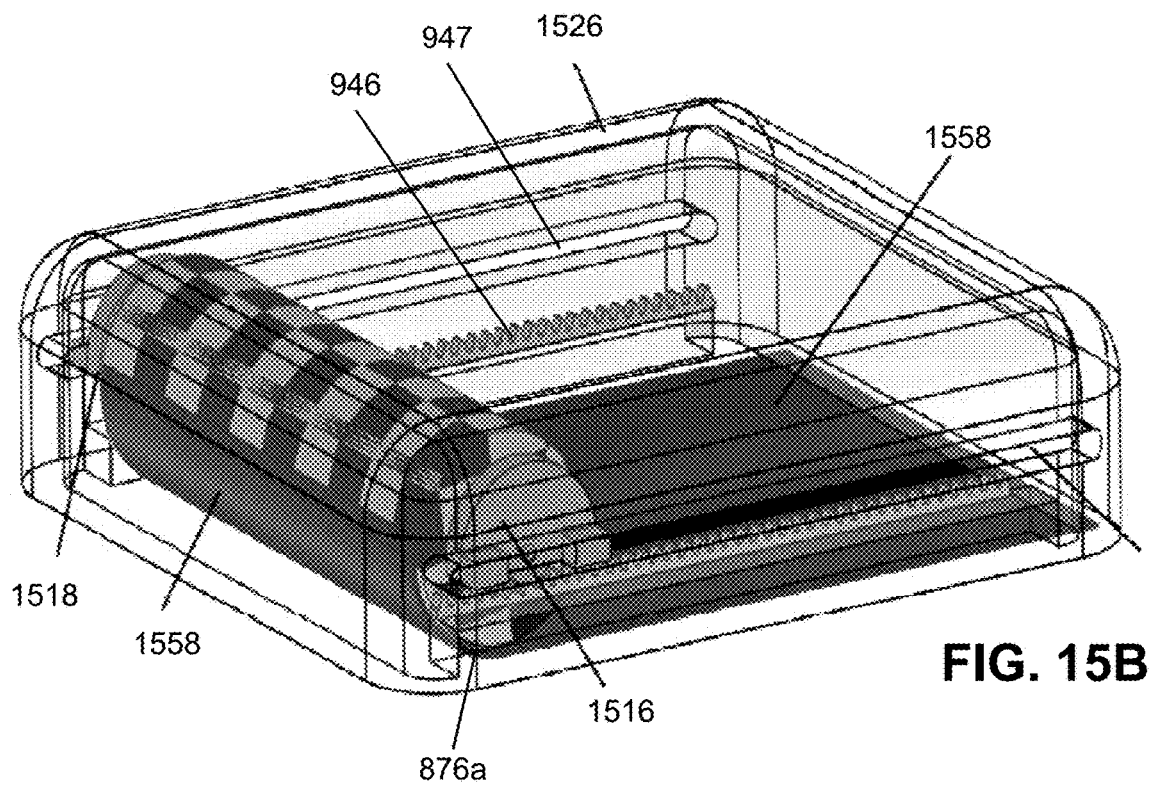
Figure 15C:
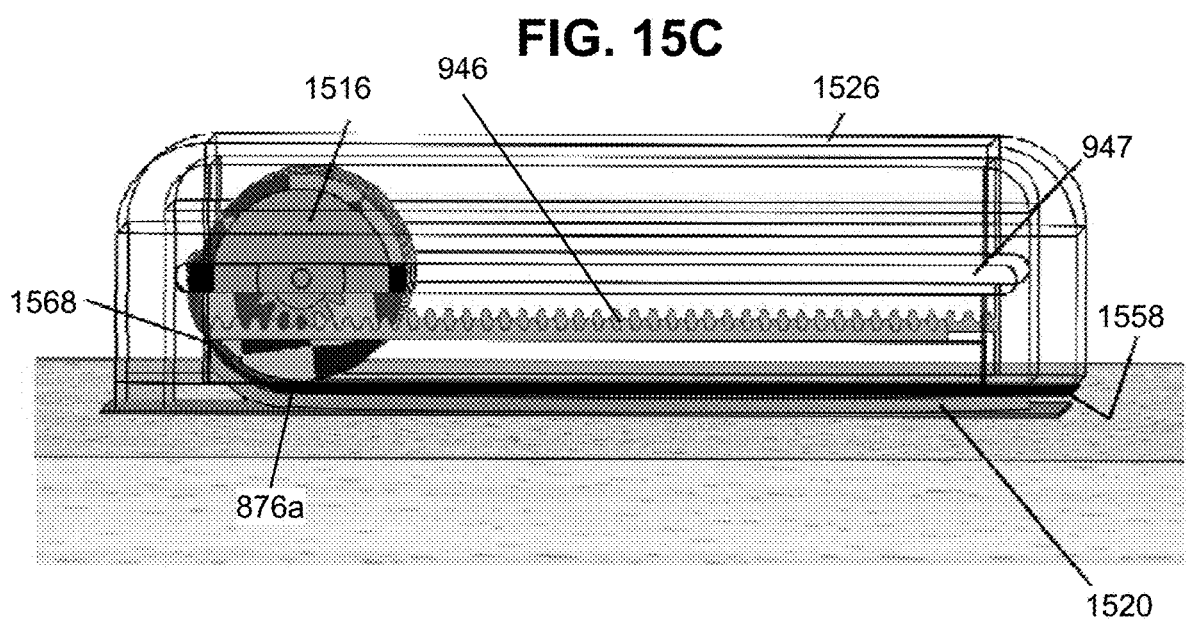

FIGS. 15A-15C are perspective views of a direct drive patch control device in accordance with an embodiment of the present invention. The control device optionally reversibly engages and/or disengages portions of a patch. Optionally disengaged portions are stored on a roller.

In some embodiments, a patch control device 1501 includes a roller 1516 that rotates and slides along a track 947 inside a frame 1526 to engage and/or disengage a medicine patch. Optionally in the disengaged state the patch is stored wound around roller 916.

In some embodiments, roller 1516 is driven by direct drive driver 1518. Driver 1518 optionally rotates a transmission 1519 which rotates roller 1516 and friction wheels 1544. Friction wheels 1544 roll along track while roller 1516 rotates rolling up and/or rolling out the patch. In some embodiments, device 1501 is loaded uses the same patch and/or is loaded as described above with respect to device 901.

In some embodiments, roller 1516 may rotate and/or move linearly along track 947. For example, propulsion may be provided by a friction wheel 1544 (e.g. a gear) rolling along a friction track 946 (e.g., a toothed track) formed in housing 1526. Driver 1518 optionally turns roller 1516. For example driver 1518 may be located inside the roller 1516. This configuration may save space over an external driver.

Optionally, the rotating speed of roller 1516 is adapted to synchronize the speed of the surface of the substrate to the linear rate of uptake and/or release of the patch. For example as the diameter of the roll grows (e.g. with increasing numbers of layers of substrate and/or patch over roller 1516) the rotation rate may be reduced with respect to the rate of linear movement of roller 1516. Optionally a synchronizer may synchronize the rate of engaging of uptake or output of substrate 1558 with the rate of movement roller 1516 and/or separation line 876a. For example distance between teeth in the track 946 may be adjusted synchronize linear motion and rotation of roller 1516. For example in FIG. 15B, where the diameter of the roll increases as roller 1516 moves rightward, the distance between the teeth in track 946 may get larger as one moves down the track from left to right and/or the ratio of rotation to linear movement is reduced as roller

1516 moves from left to right. In some embodiments, synchronizing with the roller linear and rotational velocity may to facilitate deployment of the patch with reduced wrinkle or skin pinching and/or hair pulling. Alternatively or additionally a controller may separately control the linear and rotational movements (for example with separate drivers).

FIG. 15C illustrate an optional way of mounting a standard drug patch 1520 onto roller 1516. A substrate 1558 (for example an adhesive foil without the substance on the patch) is optionally connected to the roller 1516 and/or extends out from the roller 1516 over the bottom of housing 1526. In order to connect the patch 1520 to the roller, housing 1526 is optionally placed onto patch 1520, whereupon the patch 1520 sticks to substrate 1558. For example, roller 1516 may peel and/or place substrate 1558 to from and/or to the skin on a separation line 876*a*.

In some embodiments, once patch 1520 is attached to substrate 1558, a liner may be removed from the active face (e.g. the bottom face in FIG. 15C) of the patch 1520. The exposed patch 1520 and/or device 1501 are then placed on the skin in an engaged state. Alternatively or additionally, before placing device 1501 on the skin, driver 1518 may turn the roller 1516 to cause patch 1520 and/or substrate 1558 to wrap and/or roll around the roller 1518 into a disengaged and/or stored state. In some embodiments, a protective element (e.g. to protect a patch during storage) is a part of the control device. For example the back of substrate 1558 optionally serves as a liner and/or protective layer on the patch 1520 (e.g. the active surface thereof) during storage. Optionally, device 1501 is placed onto a subject in the disengaged state. Alternatively, instead of using driver 1518 to wind up patch 1520, housing 1526 may be moved across a surface (e.g., assembly table) to cause roller 1516 to turn and move in track 947. Optionally, a tongue 1568 is provided near the roller 1516 just before patch 1520 begins to wrap around the roller 1516. For example, tongue 1568 may catch and lift off any liner that was mounted on patch 1520, so that patch 1520 rolls up on roller 1516 without the liner.

In some embodiments a roller (for example roller 916 and/or roller 1516) may be driven by a pulley and/or a linear actuator and/or a spring drive.

A Rotating Device with a Continuous Track Substrate

Reference is now made to FIGS. 16A-16E, which illustrate a transdermal delivery device 1601, constructed and operative in accordance with a non-limiting embodiment of the present invention.

In some embodiments, transdermal delivery device 1601 includes a substrate 1658 is driven by a driver 1518. Optionally, substrate 1658 includes an active surface 1620 including a substance adapted for transdermal delivery. For example, active surface 1620 may include commercially available transdermal patch impregnated or otherwise provided with a substance (e.g., drug). In some embodiments, active surface 1620 includes a patch mounted on a substrate 1658, for example with and adhesive. Alternatively or additionally, active surface 1620 may be an intrinsic part of substrate 1658.

Figure 16A:
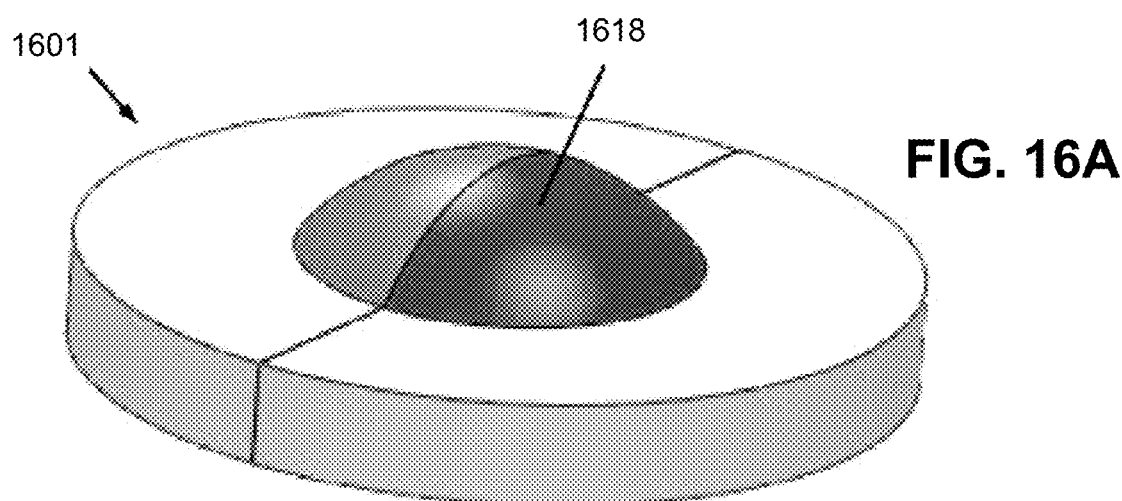
FIGS. 16A-16E illustrate a transdermal delivery assembly, having a curved continuous belt substrate in accordance with a non-limiting embodiment of the present invention.
Figure 16B:
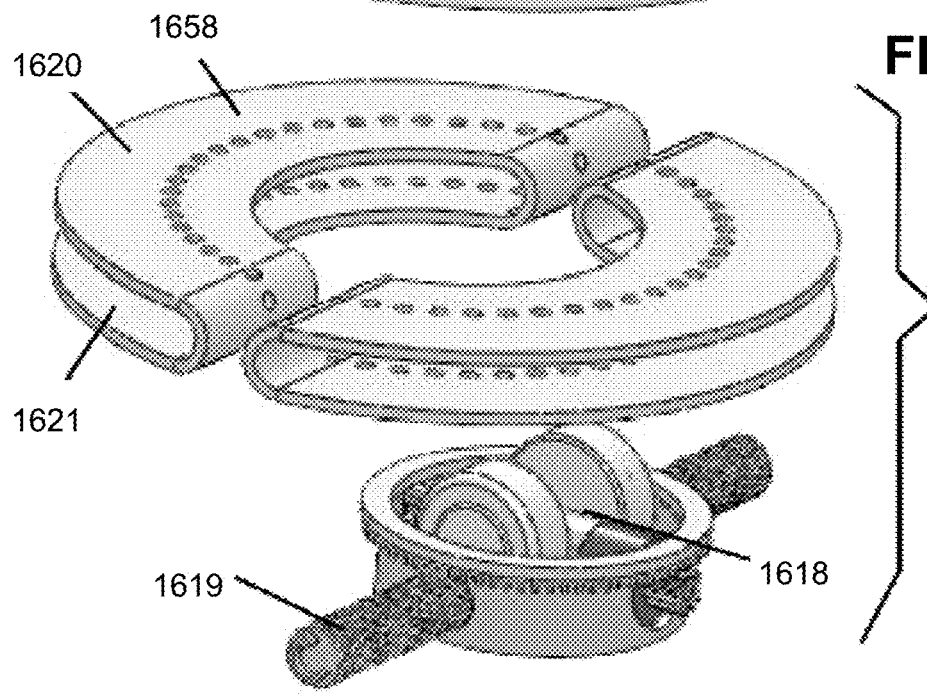
Figure 16C:
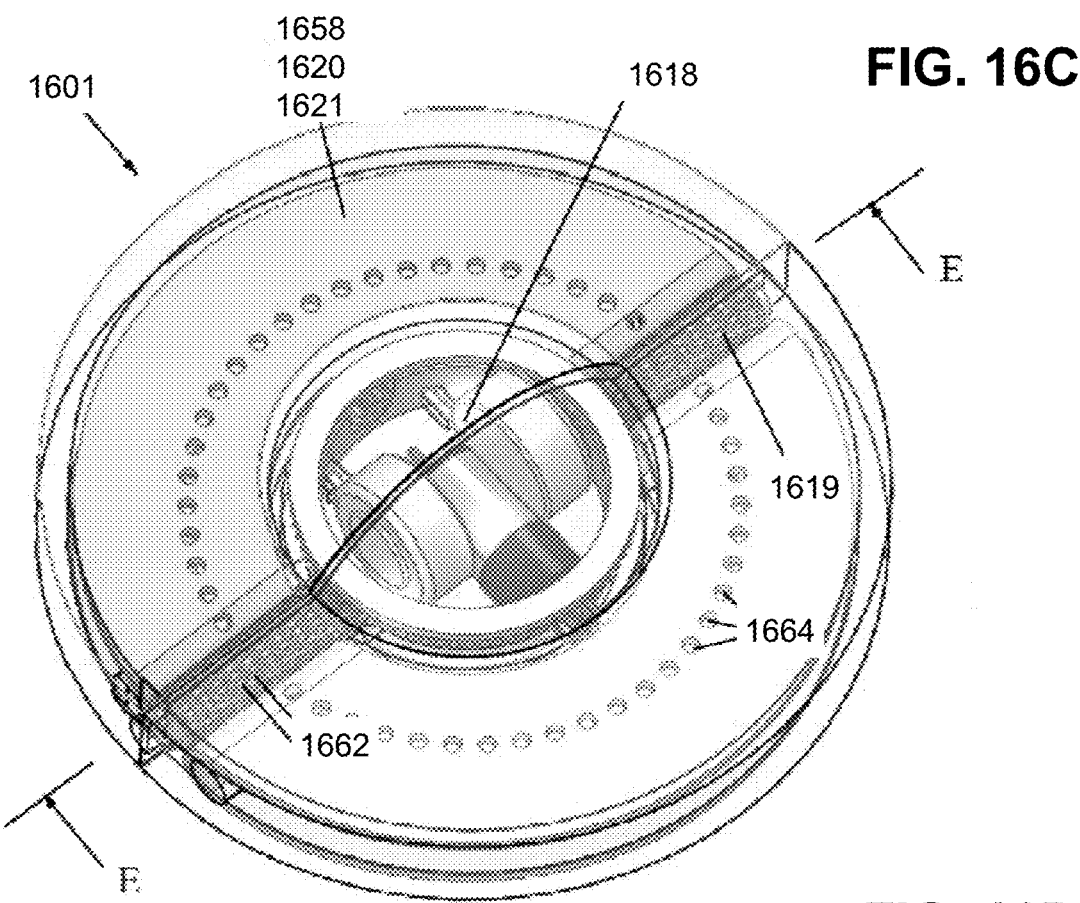
Figure 16D:
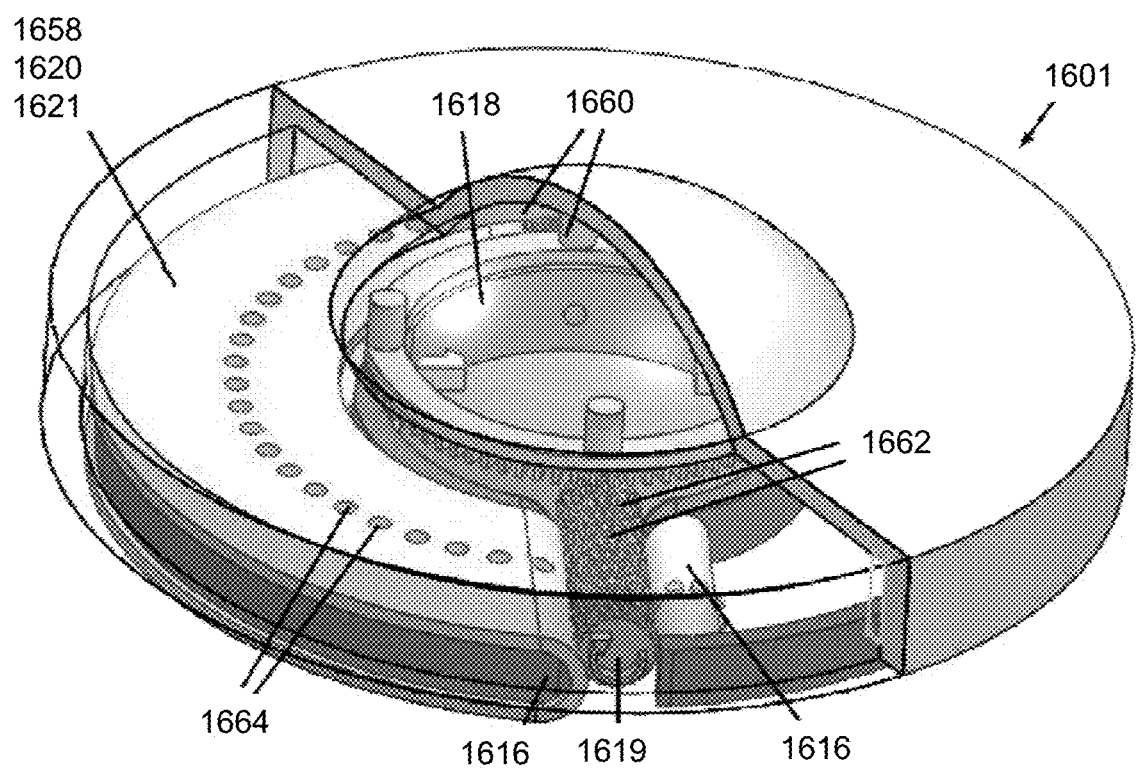
Figure 16E:
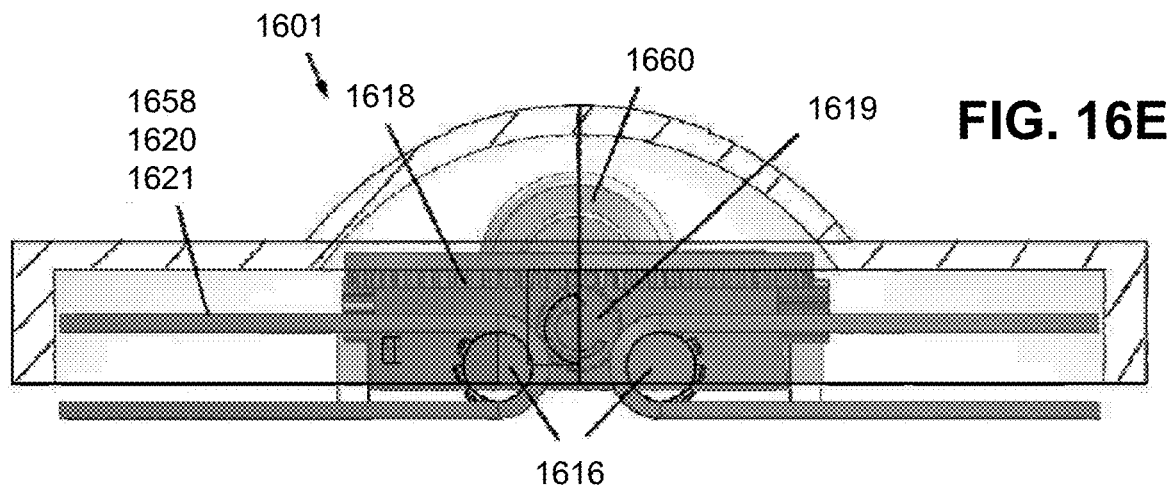

In some embodiments, driver 1618 moves active surface 1620 to one or more of a plurality of operational relationships with the skin of the subject, including active surface 1620 being in fully engaged with the skin (i.e., the entire active area of the active surface 1620 is in contact with the skin), being in partially engaged with the skin (i.e., only a portion of the active surface 1620 is in contact with the skin), and not being in engaged with the skin. In one embodiment, the operation of driver 1618 is controlled by a controller 1660 (FIG. 16D). For example, controller 1660 governs activation, deactivation and/or the speed of driver 1618. Optionally, by controlling driving 1618, controller 1660 controls when and for how long active surface 1620 is in a particular operational relationship with the skin (e.g., at what time of the day is active surface 1620 in full, partial or no contact with the skin and/or for what duration of time).

In some embodiments, transdermal delivery device 1601 may be provided by a manufacturer as a hermetically sealed assembly. Optionally active surface 1620 may be exposed inside the sealed assembly without a linear. Alternatively or additionally, active surface 1620 may have a backing that. For example a backing may protect active surface 1620 from the outer environment. Alternatively or additionally, active surface 1620 may have a liner. For example, the liner may be removed prior to loading substrate 1658 into device 1601. In some embodiments, for example where active surface is includes a discrete patch, a liner may be removed from the patch and the patch may then be mounted onto substrate 1658 and/or the patch may be mounted onto substrate 1658 and then the liner removed. One optional way of removing such a liner is described herein below with reference to FIGS. 21A-21C. Optionally, active surface 1620 may include a permeation enhancer for enhancing delivery of the substance through the stratum corneum.

In some embodiments, driver 1618 and/or controller 1660 may control and/or vary the amount of pressure applied to active surface 1620 against the skin. For example, increasing the pressure between active surface 1620 and the skin may increase the rate of substance delivery per unit time. In some embodiments, driver 1618 and/or controller 1660 may stabilize and/or control the transfer rate of the substance from active surface 1620 by causing the active surface 1620 to contact fresh areas on the skin. In some embodiments, contacting fresh skin may compensate for degradation of the substance concentration and/or absorption in older or previous areas on the skin.

In some embodiments, substrate 1658 is a continuous belt rotatably mounted on a roller 1616. For example, as illustrated in FIG. 1D, driver 1618 may be a motor with a transmission (e.g. output shaft) 1619 that meshes with the movable element (e.g., roller) 1616 or directly with substrate 1658. For example, movable element 1616 may include a gear and output shaft 1619 may be complimentary shaped (e.g., having worm threads) to mesh with and turn movable element 1616. Alternatively, output shaft 1619 may be linked to movable element 1616 via a friction drive.

In some embodiments, output shaft 1619 may be linked to movable element 1616 via a male-female connection. For example, output shaft 1619 may be provided with pins or teeth 1662 (male part) that engage holes 1664 (female part) formed in substrate 1658. Teeth 1662 and holes 1664 are also referred to as drive interface elements. Optionally, as driver 1618 turns output shaft 1619, substrate 1658 is caused to turn about rollers 1616.

In some embodiments, substrate 1658 includes an active surface, for example active surface 1620 and a secondary zone 1621. Secondary zone 1621 may be drug free zone in substrate 1658. Alternatively or additionally secondary zone 1621 may include a second drug and/or be configured for a therapeutic process. For example, zone 1621 may include a stratum corneum resurfacing element (for example for "skin activation" or "skin resurfacing"). Optionally, the stratum corneum resurfacing element may include an adhesive surface operative to attach to and peel a portion of stratum corneum. Alternatively or additionally, the stratum corneum resurfacing element may include a chemical (e.g., glycolic acid or salicylic acid) operative to peel a portion of stratum corneum. Alternatively or additionally to any combination of the above, the stratum corneum resurfacing element may include a micro-needle array.

In some embodiments, as substrate 1558 rolls onto the skin, active surface 1620 sometimes fully contacts the skin (at which time secondary zone 1621 may not contact the skin at all, but alternatively can be configured to partially or fully contact the skin, too), sometimes partially contacts the skin (at which time secondary zone 1621 may partially contact the skin, but alternatively can be configured for no contact or full contact) and sometimes does not contact the skin at all (at which time the secondary zone 1621 may fully contact the skin (but alternatively can be configured for no contact or partial contact).

In some embodiments, active surface 1620 and secondary zone 1621 move synchronously with each other. For example, in the illustrated embodiment, active surface 1620 and secondary zone 1621 form are arranged longitudinally on a continuous belt. Optionally two such belts (mirror images of each other) are arranged to roll on two rollers 1616. The substrates 1658 are optionally configured to form two halves of a round, compact device 1601. In some embodiments, the substrates 1658 are located peripherally outwards of driver 1618. For example, one driver 1618 is operative to drive more than one substrate 1658.

In some embodiments, controller 1660 (FIG. 1D) may be provided internally in (or externally to) device 1601. Optionally, controller 1660 controls operation of driver 1618. Optional controller 1660 may be preprogrammed to activate driver 1618 continuously, incrementally or a combination thereof in accordance with a treatment plan. In some embodiments, battery (not shown) may be used to energize driver 1618.

In some embodiments, substrate 1658 can be also driven manually by rotating the cover of the device 1601 which may be connected to the drive mechanism (e.g., gear, friction, male-female drive).

In one embodiment, roller 1616 has a perimeter larger than the size (rolling length) of substrate 1658. For example, in this manner, the moving and rolling speeds of the device may be synchronized.

In some embodiments, other methods may be implemented in the invention for moving an active surface with a driver to change the amount of active area engaged with the skin. For example, in some embodiments, a patch is mounted on a substrate but not on a roller. Optionally the driver is operative to grasp and/or move the substrate. For example the substrate may be arranged to be lifted off the skin by the driver, such as being moved perpendicularly off the skin. For instance the driver may lift the substrate away from the skin may be by gradually peeling at an angle and/or lifting the patch off the skin, and then afterwards reattaching the patch to the skin, either at the same place or a different place. The driver may, for example, include pincers or slender jaws and the like for grasping the substrate and patch. The driver can move the patch linearly and/or rotationally.

Figure 17:
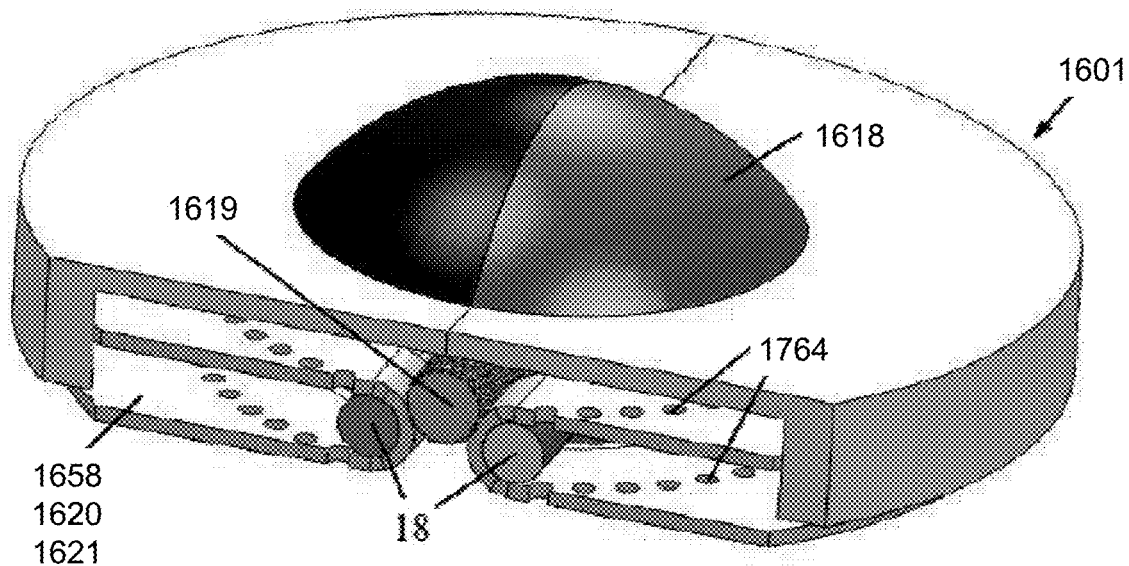
FIG. 17 illustrates an optional set of drive interface elements in accordance with an embodiment of the present invention.

Reference is now made to FIG. 17, which illustrates an optional set of drive interface elements in accordance with an embodiment of the present invention. For example, elements enhance torque to move substrate 1658. For example, the additional set of drive interface elements may include another set of holes 1764 that receive torque from driver 1618 and/or move substrate 1658 as in a tracked-wheel mechanism.

Figure 18A:
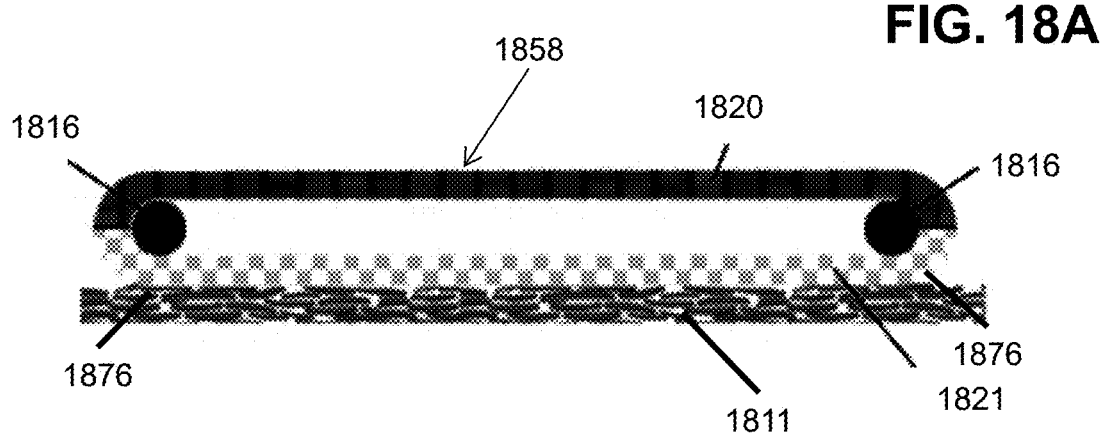
FIGS. 18A-18C illustrate progressive movement of a continuous belt substrate in accordance with an embodiment of that current invention.
Figure 18B:
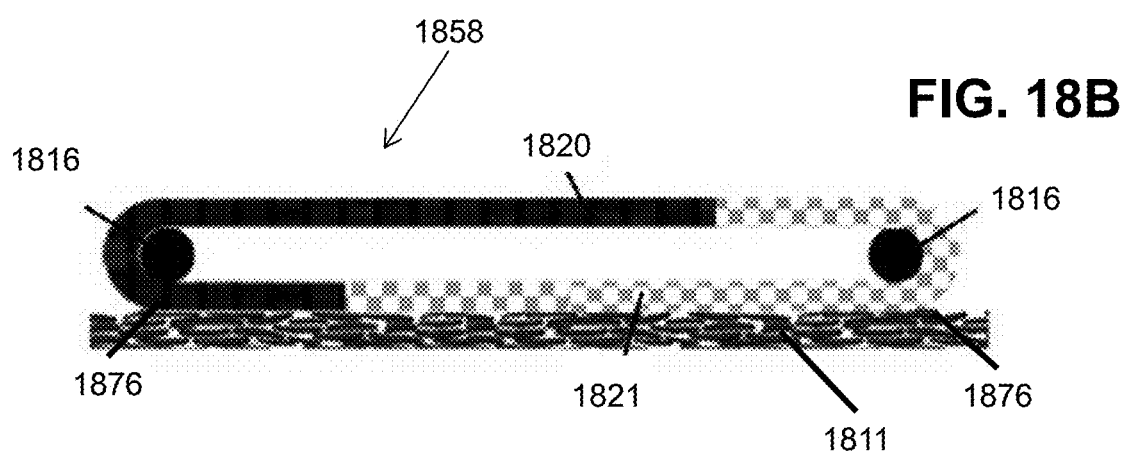
Figure 18C:
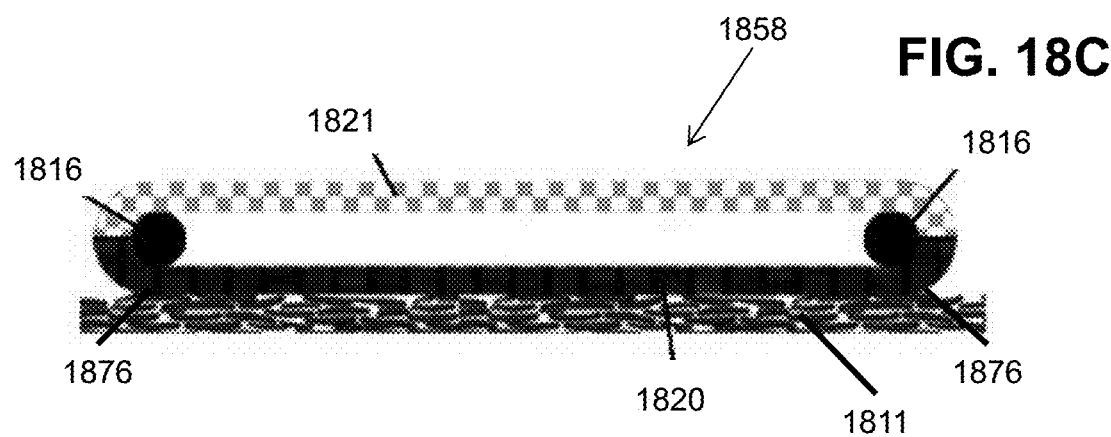

Reference is now made to FIGS. 18A-18C, which illustrate progressive movement of a continuous belt substrate 1858 including an active surface 1820 and a secondary zone 1821 in accordance with an embodiment of that current invention. Optionally a device may include a single straight continuous track substrate 1858 that rolls along the skin of a subject. Alternatively or additionally, rollers 1816 are optionally contained by a stationary housing. For example, moving substrate 1858 may engage new portions of the substrate to single area of skin. Optionally active surface 1820 is impregnated with a drug not present in secondary zone 1821. Optionally the portion of the belt positioned away from the skin (e.g. above the roller in the exemplary illustration) is disengaged from the skin. Optionally the portion of the belt positioned against skin (e.g. below the roller in the exemplary illustration) is engaged to the skin. An active surface in the disengaged position is optionally stored for later engagement by further rolling to the engaged position. For example, a disengaged portion (e.g. above the rollers) may be covered by the housing of the device (for example as illustrated by zone 1620 in FIGS. 16A-16B.

In some embodiments moving substrate 1858 may change a rate of drug administration to a subject. For example, in FIG. 18A, active surface 1820 with the substance is above rollers 1816 and secondary zone 1821 is below rollers 1816, as a result active surface 1820 is optionally distanced from and/or fully disengaged from skin 1811 of a subject and/or the drug is not being administered to the subject. In the example of FIG. 3B, substrate 1858 has turned so that active surface 1820 is partially turned below rollers 1816 and secondary zone 1821 is partially above rollers 1816, as a result a portion of active surface 1820 is engaged to and/or in contact with skin 1811 of a subject and/or the drug is administered to the subject at a reduced rate. In FIG. 18C, the substrate 1858 has turned so that active surface 1820 is now below rollers 1816 and secondary zone 1821 is now above rollers 1816, as a result a active surface 1820 is fully engaged to and/or in contact with skin 1811 of a subject and/or the drug is administered to the subject at a full rate. Optionally, a second roller may be supplied whose belt includes a protective liner that contacts substrate 1858 in the stored position. For example, in the case of continuous belt substrate 1858, rollers 1816 may simultaneously peel and/or place substrate 1858 from and to the skin on separation lines 1876.

Figure 19:
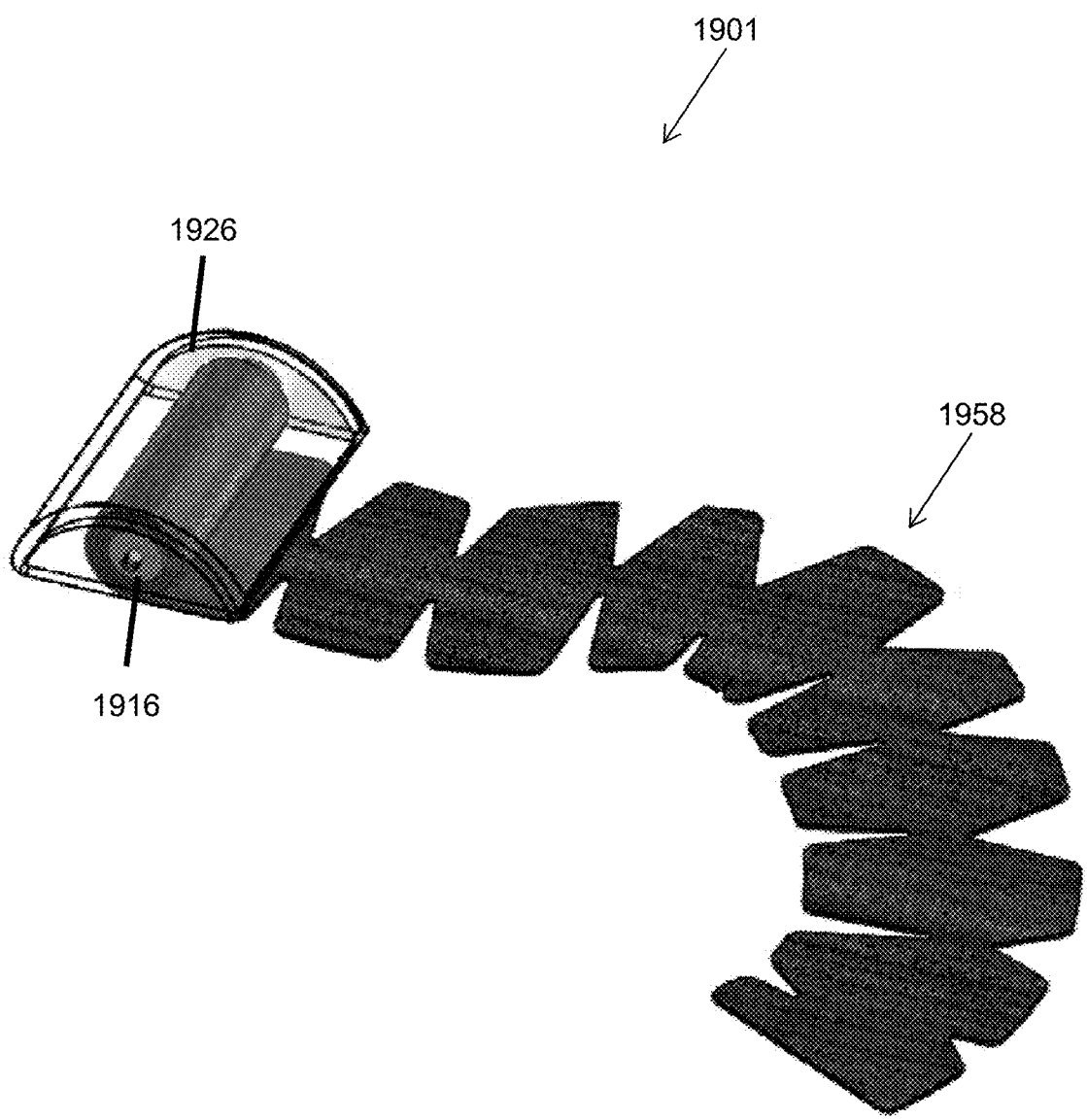
FIG. 19 illustrates a patch engagement device according to an embodiment of the current invention.

FIG. 19 illustrates a roller patch engagement device 1901 for applying a patch according to an embodiment of the current invention. In some embodiments, a substrate 1958 is optionally stored in a frame 1926 on a roller 1916. For example, as frame 1926 rolls across the skin of a subject, it engages a further portion of substrate 1958. Optionally, device 1901 is driven by a driver.

In some embodiments, substrate 1958 may have active and/or inactive surfaces. For example, the underlying substrate 1958 may be inactive, but medicine patches of one or more kinds may be connected (for example by adhesive) to substrate 1958 in one or more locations. As the substrate is rolled into engagement, the various active surfaces are engaged. Alternatively or additionally, substrate 1958 may be a homogenous patch. For example, device 1901 may constantly roll out new substrate for example to keep a steady dose of the drug over a long time.

In some embodiments, rotation of roller 1916 is driven by a driver. Optionally the driver may drive roller 1916 at a constant rate. For example the dose schedule of the medicine may be determined by the distribution of active surfaces along substrate 1958. Alternatively or additionally, a driver may be controlled by a controller that may be programmed to engage a new section of substrate 1958 at specific times and/or dependent upon events. Alternatively or additionally, device 1901 may be manually operated by pushing along the skin.

In some embodiments, a substrate (for example substrate 1958) may be slotted or otherwise shaped so that device 1901 can engage the substrate along the skin while moving along a curved path and/or a straight path.

Figure 20A:
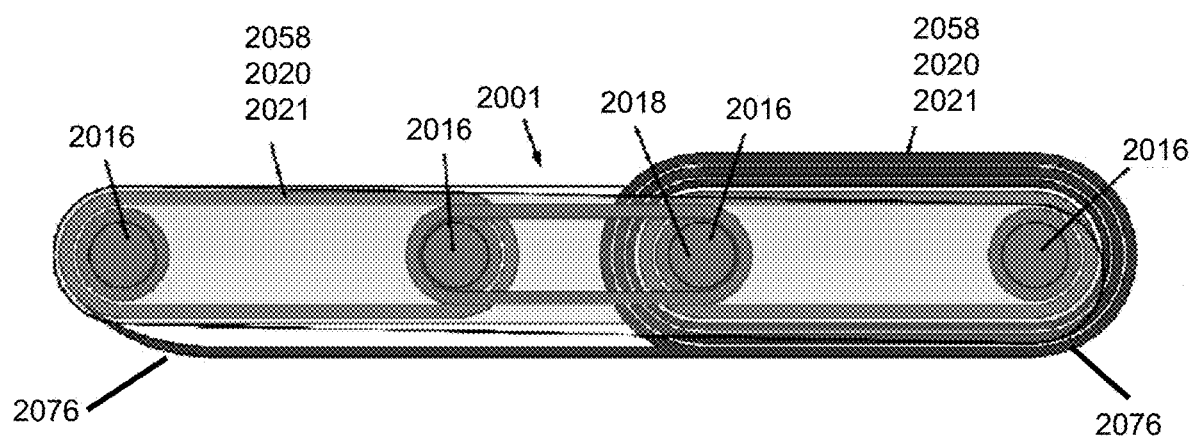
FIGS. 20A-20B illustrate a transdermal delivery belt assembly constructed and operative in accordance an embodiment of the present invention.
Figure 20B:
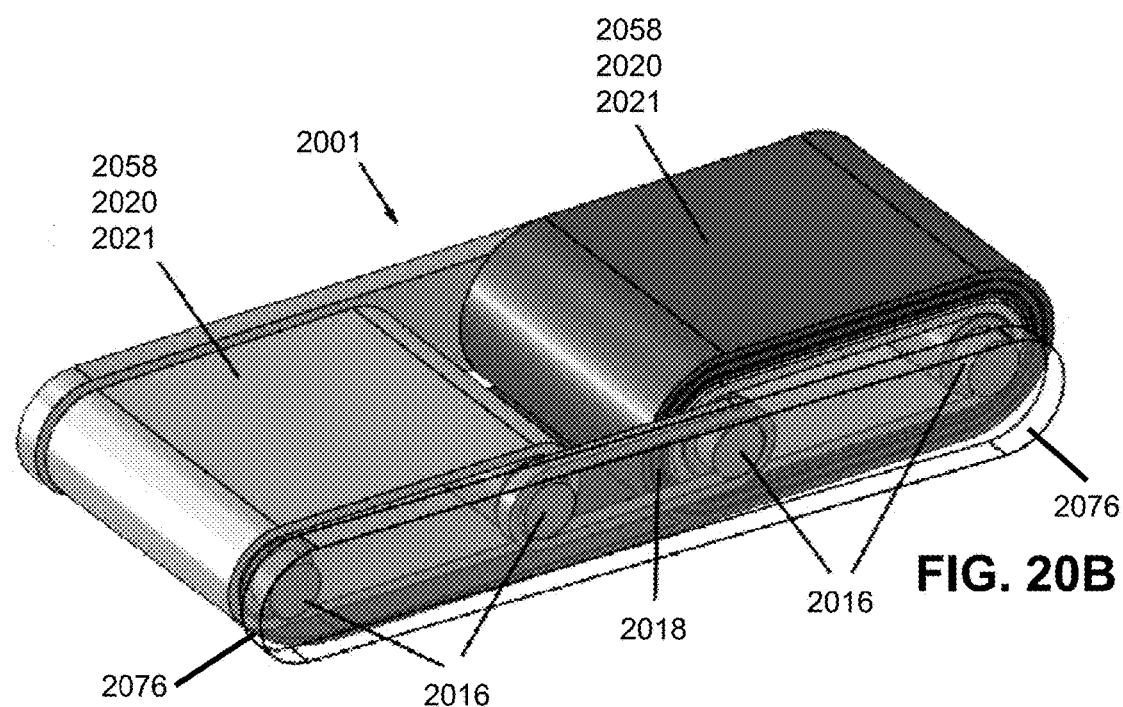

Reference is now made to FIGS. 20A and 20B, which illustrate a transdermal delivery assembly 2001, constructed and operative in accordance with another non-limiting embodiment of the present invention. In some embodiments, a belt substrate 2058 is wound around two sets of rollers 2016. Substrate 2058 optionally includes one or more zones. For example an active surface 2020 and a secondary zones 2021 (e.g., a stratum corneum resurfacing elements). Optionally, a driver 2018 turns rollers 2016 for driving substrate 2058. One of rollers 2016 is optionally the output shaft of driver 2018. For example, driver 2018 may drive rollers 2016 and/or substrate 2058 directly. For example, rollers 2016 may simultaneously peel and/or place substrate 2058 from and to the skin on separation lines 2076.

Reference is now made to FIGS. 21A-21B, which illustrate a patch engaging device 2101 which peels and lifts a patch to a disengaged position in accordance with an embodiment of the current invention. In some embodiments substrate 2158 is arranged on rollers 2116*a* and 2116*b*. Optionally, rollers 2116*a* and 2116*b* are disposed in a housing 2126. For example, rollers 2116*a* and 2116*b* may rotate and move linearly along a track 2146. As rollers 2116*a* and 2116*b* move along the skin of a subject in one direction, they optionally disengage the substrate 2158 by peeling substrate 2158 off the skin. As rollers 2116*a* and 2116*b* move along the skin of a subject in another direction, they optionally engage the substrate 2158 by placing substrate 2158 onto the skin.

In some embodiments, rollers 2116*a* and 2116*b* rotate and/or move along track 2146 to engage and/or disengage substrate 2158 while housing 2126 remains stationary. For example, housing 2126 may be attached to a subject (e.g. with an adhesive). Optionally movement may be driven by a driver and/or controlled by a controller. Alternatively or additionally housing 2126 and rollers 2116*a* and 2116*b* may be moved along the subject.

In some embodiments, tension from a puller (for example connection 2180*b* to frame 2126 and upper roller 2116*a* is converted by a direction converting element (for example lower roller 2116*b* and/or for example guide 895 of FIG. 8A) to peel a patch off of skin. For example, guide 895 may include a bumper and/or an arm and/or flat support and/or a rounded support and/or a smooth support.

In some embodiments, a first portion 2121*a* of substrate 2158 is held stationary (for example at location 2180*a* on the base of the frame) on and/or near the skin surface of the subject while second portion 2121*b* is held (for example at location 2180*b* on frame) distanced from the skin of the recipient. For example, portion 2121*a* near the skin may be between 1 to 5 mm from the skin and/or between 1 to 0.1 mm of the skin and/or less than 0.1 mm from the skin and/or in contact with the skin. For example, portion 2121*b* is held stationary distanced from the skin. For example portion 2121*b* may be between 1 to 5 mm from the skin and/or between 0.1 to 1 mm of the skin and/or more than 5 mm from the skin. For example portion 2121*b* may be between 10 to 1000 times as far from the skin as portion 2121*a* and/or between 2 to 10 times as far and/or more than 1000 times as far. Optionally the length of the strip of substrate 2158 between portions 2121*a* and 2121*b* is longer than the distance between points 2180*a* and 2180*b*. For example the extra length of the strip may leave slack from wrapping the strip in an S shaped curve around rollers 1916.

In some embodiments, substrate 2158 wraps around a pair of rollers 2116*a* and 2116*b* in an S-curve. In some embodiments this arrangement saves on space and/or maintains synchronization of the patch and roller motion.

In some embodiments, substrate 2158 wraps around two rollers 2116*a* and 2116*b* (for example as illustrated in FIG. 21A-21C). Alternatively or additionally, substrate 2158 wraps around more than two rollers 2116*c*, 2116*d*, and 2116*e* (for example in device 2102 as illustrated in FIG. 21D). Optionally, some of rollers 2116*c*, 2116*d*, and 2116*e* may include a gear 2170. An optional gear train 2171 meshes between gear 2170 and an optional gear rack 2172. In some embodiments, this arrangement provides precise control and synchronization of the patch and roller motion and/or increases torque and/or speed.

In some embodiments, multiple rollers 2116*a*-2116*e* facilitates storing substrate 2158 disengaged and spread out distanced from the skin. In some cases this may avoid a potential problem. For example, in some cases where a patch is stored on rolled around a roller, as the patch is laid out on the skin of the subject, the patch unrolls from the roller and sticks to the skin of the subject. As the patch is peeled off the skin, it starts to wrap around the roller. Depending on the diameter of the roller and adhesive properties of the patch (among other factors), if only one roller is used, the patch may stick to itself as it wraps around the roller. This self sticking may make it difficult to unwrap the patch in order to redeploy the patch, engaging it with the skin. An alternative solution may include use of large diameter rollers. Another alternative solution is to place a liner (for example substrate 1558 as illustrated in FIG. 15C and/or protector 922 as illustrated in FIG. 14) on the dorsal face of the patch and/or between layers of the patch as it wraps around the roller. Some embodiments with multiple rollers 2116*a*-2116*e* solve this problem by ensuring the patch does not wrap onto itself and/or stick to itself during storage. In some embodiments, multiple rollers may be configured to avoid significantly increasing the size of the device. Optionally, an additional roller or rollers may cause the patch to travel a longer distance when getting peeled off and take the place of a single, large-diameter roller. For example, rollers 2116*b* and 2116*e* may peel and/or place substrate 2158 from and/or to the skin on a separation line 2176.

Figure 22A:
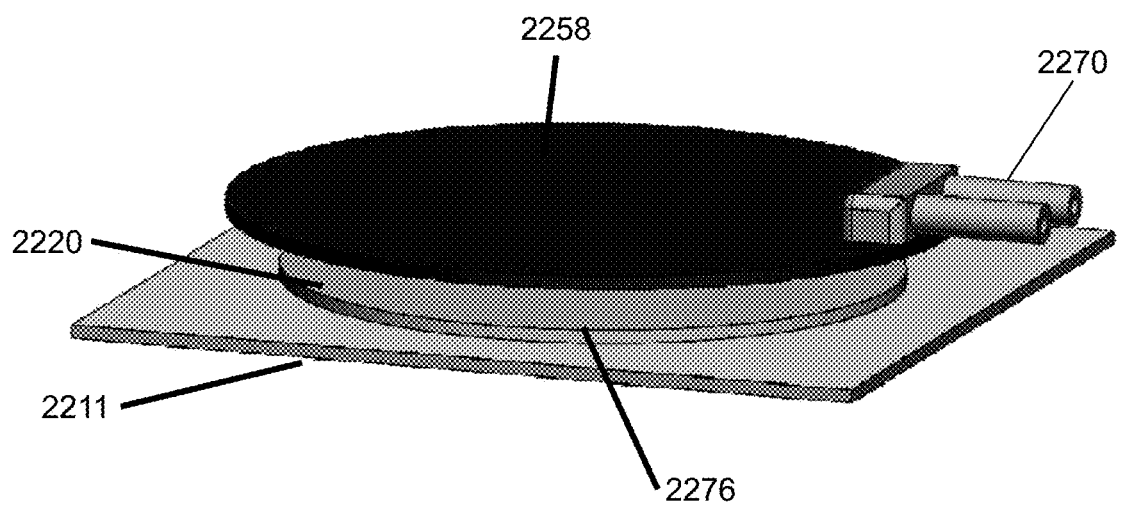
FIGS. 22A-22B illustrate a patch control device with a ductile substrate in accordance with an embodiment of the current invention.
Figure 22B:
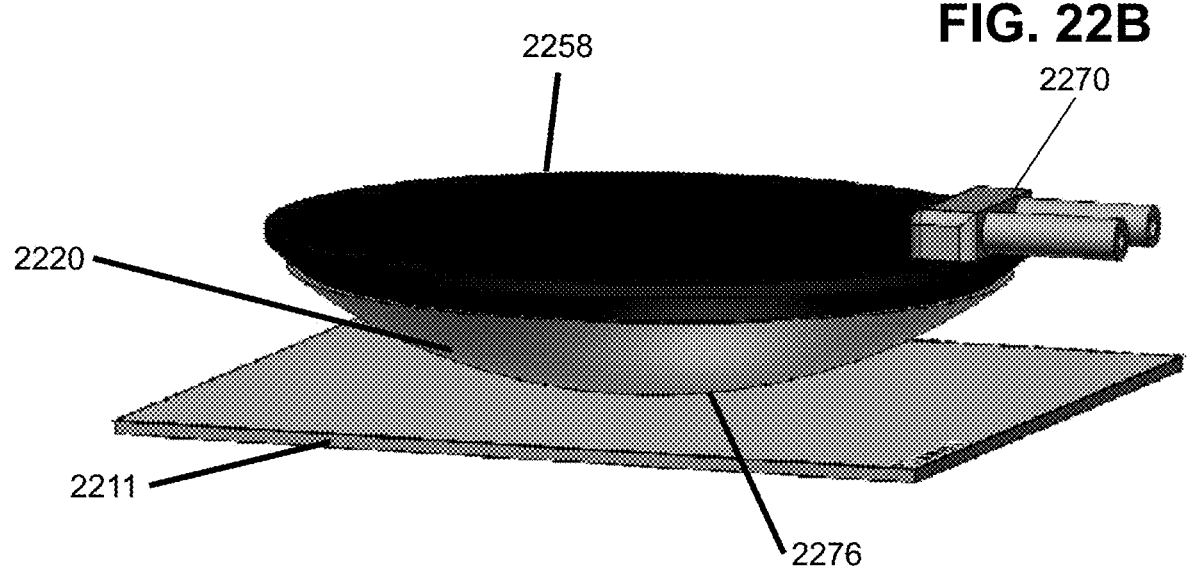

FIGS. 22A-22B illustrate a patch control device that peels the edges of a patch with a shape changing substrate in accordance with an embodiment of the current invention. In some embodiments, bending substrate 2258 has a flattened state which engages a patch 2220 with skin 2211 of a subject for example as illustrated in FIG. 22A. Substrate 2258 optionally has a bent configuration which lifts an edge of patch 2220 off of skin 2211 in a disengaged state, for example as illustrated in FIG. 22B.

In some embodiments, substrate 2258 includes the surface of a balloon. For example a driver of the device may include a pump which pumps fluid (for example air) through an opening 2270 to inflate the balloon into the disengaged state and/or deflate the balloon into an engaged state. Alternatively or additionally other shape changing substrate for example as nitinol, a joint may be used in place of a balloon. Optionally substrate 2258 is attached to the dorsal face of patch 2220. Alternatively or additionally substrate 2258 may be attached to the edges thereof. For example, substrate 2258 may peel and/or place patch 2220 from and/or to the skin on a curved separation line 2276.

Figure 23A:
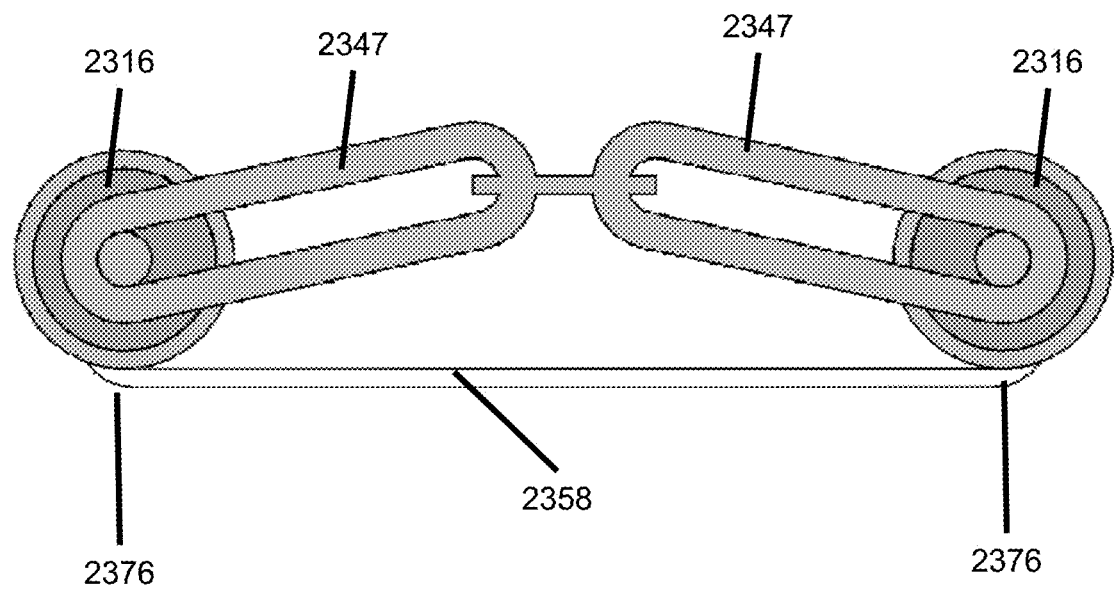
FIGS. 23A-23B illustrate a patch control device in accordance with an embodiment of the present invention.
Figure 23B:
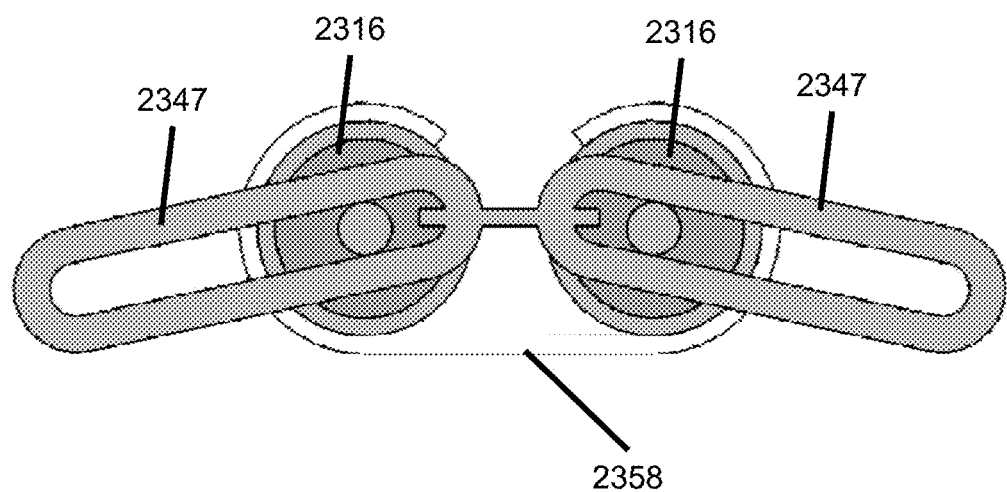

FIGS. 23A-23B illustrate a patch control device with a roller on an angled track that lifts and rolls a patch in accordance with an embodiment of the present invention. In some embodiments, as a roller 2316 rolls up a substrate 2358, roller 2316 and substrate 2358 are lifted on track 2347 away from skin. In some embodiment multiple rollers 2316 may be mounted on multiple tracks 2347. For example rollers 2316 may act in a synchronized fashion for engaging of substrate 2458 fully from skin (for example as illustrated in FIG. 23A) and/or fully engaging substrate 2358 (for example as illustrated in FIG. 23B). Alternatively or additionally one roller 2316 may function to partially disengage and/or engage substrate 2358. For example, rollers 2316 may peel and/or place substrate 2358 from the skin on dual separation lines 2376.

Figure 24:
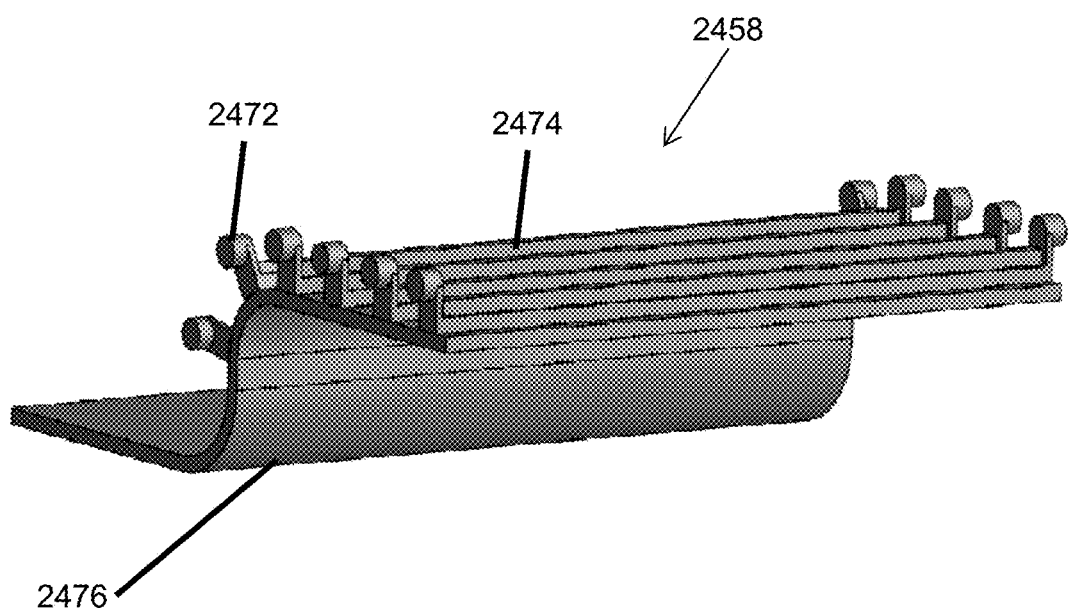
FIG. 24 illustrates a ductile substrate in accordance with an embodiment of the current invention.

FIG. 24 illustrates a ductile substrate accordance with an embodiment of the current invention. In some embodiments, a substrate 2458 may be hung hangers 2472 and/or supports 2474 from a dorsal side thereof. Optionally an active surface (e.g. a patch) may be located on a ventral face of substrate 2458. Optionally hangers 2472 may be moved dorsally and ventrally to disengage and/or engage the active surface. For example, the movement of hangers 2472 may be in a wave motion to peel the substrate 2458 from the skin along a separation line 2476. In some embodiments placing hangers 2472 and/or moving parts on the dorsal side of a substrate may protect hair of subject from being trapped in the moving parts.

Figure 25A:
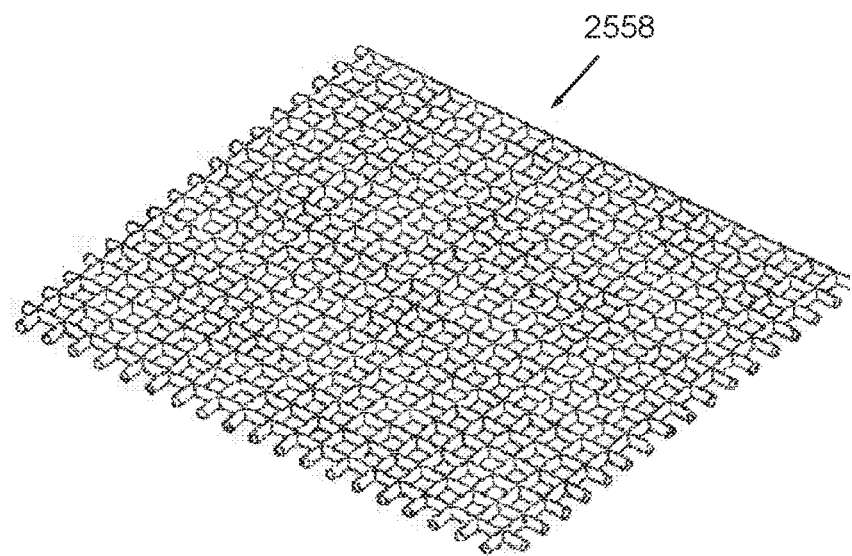
FIGS. 25A-25B illustrate an expandable substrate in accordance with an embodiment of the current invention.
Figure 25B:
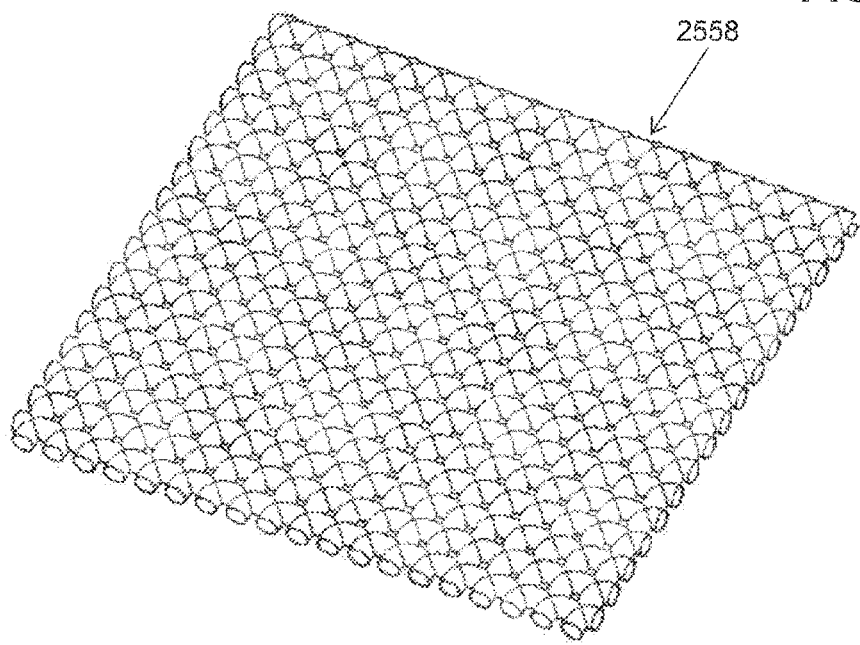

FIGS. 25A-25B illustrate an expandable patch control substrate that is placed between a patch and skin. In some embodiments, expanding a substrate 2558 between a patch and skin (for example as illustrated in FIG. 25B) may disengage the patch. In some embodiments, contracting a substrate 2558 between a patch and skin (for example as illustrated in FIG. 25B) may engage the patch. Optionally substrate 2558 may include an inflatable mesh.

It is expected that during the life of a patent maturing from this application many relevant technologies will be developed and the scope of the terms for example patch is intended to include all such new technologies a priori.

As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A drug patch device comprising:
a roller rotationally mounted in a housing and linearly movable along a track in said housing, wherein said roller comprises a drug patch interface member capable of engaging and disengaging a drug patch via an open face formed in said housing and rotation of said roller rolls up or unrolls said drug patch onto or off said roller, and further comprising a tongue near said roller operative to catch and remove a liner from the drug patch.

2. The drug patch device according to claim 1, further comprising a drug patch wound on said roller.

3. The drug patch device according to claim 2, wherein said drug patch comprises a skin interface layer and a protective liner, wherein said protective liner contacts said roller.

4. The drug patch device according to claim 1, wherein said drug patch interface member comprises a portion of a shaft of said roller.

5. The drug patch device according to claim 1, wherein said drug patch interface member comprises a substrate coupled to said roller.

6. The drug patch device according to claim 5, wherein said substrate comprises an adhesive foil.

7. The drug patch device according to claim 1, wherein said track comprises a plurality of drive teeth that engage said roller.

8. The drug patch device according to claim 7, wherein a distance between said teeth changes as said roller moves along said track.

9. The drug patch device according to claim 1, wherein said roller is coupled to a direct drive driver.

10. The drug patch device according to claim 1, wherein said roller is coupled to a driver via a transmission.

11. The drug patch device according to claim 1, wherein said roller is coupled to a driver located inside said roller.

12. The drug patch device according to claim 1, wherein said tongue is positioned near said roller just before drug patch begins to wrap around said roller.

13. A method of manipulating a drug patch comprising:
using said drug patch device of claim 1 to engage or disengage a drug patch via said open face, wherein rotation of said roller rolls up or unrolls said drug patch onto or off said roller.

14. The method according to claim 13, comprising placing said open face of said housing over said drug patch and at least partially winding said drug patch around said roller.

15. The method according to claim 14, comprising synchronizing rotation of said roller with a rate of uptake of said drug patch onto said roller.

16. The method according to claim 13, comprising storing said drug patch at least partially wound around said roller.

17. The method according to claim 13, comprising placing said open face of said housing on skin and unrolling at least a portion of said drug patch from said roller onto said skin.

18. The drug patch device according to claim 1, further comprising catching and removing a liner mounted on said drug patch so that said drug patch rolls onto said roller without the liner.

* * * * *